US012691168B2

(12) United States Patent
He et al.

(10) Patent No.: US 12,691,168 B2
(45) Date of Patent: Jul. 28, 2026

(54) VACCINE FOR PREVENTING AND TREATING MERKEL CELL CARCINOMA

(71) Applicant: ADVACCINE (SUZHOU) BIOPHARMACEUTICALS CO. LTD, Suzhou (CN)

(72) Inventors: Yue He, Suzhou (CN); Gan Zhao, Suzhou (CN); Lunan Zhang, Suzhou (CN); Xin Cheng, Suzhou (CN); Qingling Yu, Suzhou (CN)

(73) Assignee: ADVACCINE (SUZHOU) BIOPHARMACEUTICALS CO. LTD., Suzhou (CN)

( * ) Notice: Subject to any disclaimer, the term of this patent is extended or adjusted under 35 U.S.C. 154(b) by 576 days.

(21) Appl. No.: 18/253,034

(22) PCT Filed: Oct. 29, 2021

(86) PCT No.: PCT/CN2021/127386
§ 371 (c)(1),
(2) Date: May 15, 2023

(87) PCT Pub. No.: WO2022/100459
PCT Pub. Date: May 19, 2022

(65) Prior Publication Data
US 2023/0414742 A1 Dec. 28, 2023

(30) Foreign Application Priority Data

Nov. 16, 2020 (CN) .......................... 202011276594.0

(51) Int. Cl.
| | |
|---|---|
| *A61K 39/00* | (2006.01) |
| *A61K 39/12* | (2006.01) |
| *A61K 39/39* | (2006.01) |
| *A61P 31/20* | (2006.01) |
| *A61P 35/00* | (2006.01) |
| *C07K 14/005* | (2006.01) |

(52) U.S. Cl.
CPC .............. *A61K 39/12* (2013.01); *A61K 39/39* (2013.01); *A61P 31/20* (2018.01); *A61P 35/00* (2018.01); *C07K 14/005* (2013.01); *A61K 2039/53* (2013.01); *A61K 2039/55505* (2013.01); *A61K 2039/55511* (2013.01); *A61K*

*2039/55561* (2013.01); *A61K 2039/55572* (2013.01); *A61K 2039/876* (2018.08); *C12N 2710/22022* (2013.01); *C12N 2710/22034* (2013.01)

(58) Field of Classification Search
CPC ...... A61K 2039/53; A61K 2039/55561; A61K 2039/55572; A61K 39/12; A61P 31/20
See application file for complete search history.

(56) References Cited

U.S. PATENT DOCUMENTS

2006/0045881 A1 3/2006 Molldrem

FOREIGN PATENT DOCUMENTS

| | | |
|---|---|---|
| CN | 1346366 A | 4/2002 |
| CN | 101166546 A | 4/2008 |
| CN | 103826653 A | 5/2014 |
| CN | 109922830 A | 6/2019 |
| CN | 110462031 A | 11/2019 |
| CN | 111918666 A | 11/2020 |
| CN | 113278634 A | 8/2021 |
| WO | WO2018049165 * | 3/2018 |

OTHER PUBLICATIONS

Tabachnick-Cherny et al., "Polyomavirus-driven Merkel cell carcinoma: Prospects for therapeutic vaccine development", Molecular Carcinogenesis, pub. Jul. 2020, 59:807-821.*
Molecular Carcinogenesis, pub. Jul. 2020, 59:807-821. (Year: 2020).*
[No Author Listed], GenBank Accession No. FN178624.1: Synthetic construct for Merkel cell polyomavirus major capsid protein VP1 gene. Apr. 1, 2009. 2 pages.

* cited by examiner

*Primary Examiner* — Barry A Chestnut
(74) *Attorney, Agent, or Firm* — Mintz, Levin, Cohn, Ferris, Glovsky and Popeo, P.C.

(57) ABSTRACT

The present invention provides a novel vaccine for preventing and treating Merkel cell carcinoma. The present invention constructs a therapeutic vaccine based on a Merkel cell polyomavirus capsid protein VP1 by taking the Merkel cell polyomavirus capsid protein VP1 as an antigen, in combination with a TLR agonist. The present invention effectively solves the problem of prevention and treatment of the Merkel cell carcinoma and has great application value and application prospects.

20 Claims, 16 Drawing Sheets

Specification includes a Sequence Listing.

FIG. 15

```
                              SEQUENCE LISTING

<160> NUMBER OF SEQ ID NOS: 20

<210> SEQ ID NO 1
<211> LENGTH: 1272
<212> TYPE: DNA
<213> ORGANISM: Artificial Sequence
<220> FEATURE:
<223> OTHER INFORMATION: Synthetic

<400> SEQUENCE: 1
atggccccaa agaggaaggc cagctccacc tgcaagacac ccaagcgcca gtgtatcccc      60
aagcctggct gctgtcctaa cgtggccagc gtgccaaagc tgctggtgaa gggaggagtg     120
gaggtgctgt ccgtggtgac cggcgaggac tctatcacac agatcgagct gtatctgaac     180
ccacggatgg gcgtgaatag cccagatctg cccaccacat ccaattggta cacctataca     240
tacgacctgc agcccaaggg ctctagccct gatcagccaa tcaaggagaa cctgcccgcc     300
tactccgtgg ccagagtgtc tctgcctatg ctgaatgagg acatcacctg cgatacactg     360
cagatgtggg aggccatctc tgtgaagacc gaggtggtgg gcatctcctc tctgatcaac     420
gtgcactatt gggacatgaa gagggtgcac gattacggag caggaatccc cgtgagcgga     480
gtgaattatc acatgttcgc catcggagga gagccactgg acctgcaggg actggtgctg     540
gattatcaga ccgagtaccc aaagaccaca aacggcggcc ccatcaccat cgagacagtg     600
ctgggcagga agatgacacc taagaaccag ggcctggacc cacaggccaa ggccaagctg     660
gacaaggatg gcaattaccc tatcgaagtg tggtgtccag atcccagcaa gaacgagaat     720
tcccgctact atggctctat ccagaccggc agccagaccc cacagtgct gcagttctcc      780 aacacactga ccacagtgct gctggacgag aatggagtgg gacctctgtg caagggcgac     840
ggactgttta tctcctgtgc cgatatcgtg ggcttcctgt ttaagacctc tggcaagatg     900
gcactgcacg gactgccaag gtatttcaac gtgacactgc ggaagagatg ggtgaagaat     960
ccttacccag tggtgaacct gatcaatagc ctgtttcca acctgatgcc caaggtgagc     1020
ggccagccta tggagggcaa ggacaatcag gtggaggagg tgcggatcta tgagggatcc     1080
gagcagctgc aggcgaccc tgatatcgtg agattcctga taagtttgg ccaggagaag     1140 accgtgtacc caaagccttc tgtggcacca gcagcagtga catttcagag caatcagcag     1200
gataagggca aggcaccact gaagggacca cagaaggcat ctcagaagga gagccagacc     1260
caggagctgt ga                                                       1272
```

```
<210> SEQ ID NO 2
<211> LENGTH: 1272
<212> TYPE: DNA
<213> ORGANISM: Artificial Sequence
<220> FEATURE:
<223> OTHER INFORMATION: Synthetic

<400> SEQUENCE: 2 atggcccta agcggaaagc cagtagcact tgcaagacac ccaagaggca gtgcattcct      60
aagcccggtt gctgccccaa cgtggcctca gtgcctaagc tgctggtgaa gggcggcgtg     120
gaagtcctgt ccgtggtgac tggcgaagac agcatcacac agattgagct gtacctgaat     180
cctcggatgg gcgtgaacag cccagacctg cctacaacat ctaactggta tacctataca     240
tacgatctgc agccaaaggg cagctccccc gaccagccaa tcaaggagaa tctccctgcc     300
tactccgtgg ccagggtgtc cctgccaatg ctgaacgaag acatcacctg cgacaccctc     360
cagatgtggg aggctatcag tgtcaagaca gaggtggtgg gcatctcctc tctgatcaac     420
gtgcactact gggatatgaa gcgtgtgcac gactacggcg ccggcattcc tgtgagcggc     480
gtgaactatc atatgttcgc catcggcggc gagccactgg acctgcaggg actggtgctc     540
gactaccaga ccgagtaccc taagacaaca aacggcggcc caattactat cgagaccgtg     600
ctggggagaa aaatgacccc taagaaccag ggcctcgacc cccaggccaa ggccaagctc     660
gacaaggacg gaaattaccc tatcgaggtg tggtgccccg accccagcaa gaacgagaac     720
agcaggtatt acggctctat ccagactggc tcacagacac caacagtgct gcagttcagc     780
aacacactga ccacagtgct gctggacgag aacggcgtgg accccctgtg caagggcgat     840
gggctgttca tcagttgtgc tgacattgtg ggcttcctgt tcaagaccag cggaaagatg     900
gccctgcacg gactgccacg ctacttcaac gtgaccctgc gcaaacggtg ggtgaagaac     960
ccttacccag tggtgaacct gattaactcc ctgttcagca acctcatgcc taaggtgagc    1020
ggacagccta tggaaggcaa agacaatcag gtggaggagg tgaggatcta cgagggctct    1080
gagcagctgc aggagaccc cgatatcgtg cgtttcctgg ataagttcgg ccaggagaag    1140
accgtgtacc ccaaacctag cgtggctcca gccgcagtga ccttccagtc taaccagcag    1200
gacaagggca ggccccccct taagggccct cagaaggcca gccagaagga aagccagacc    1260
caggagctgt ga                                                       1272

<210> SEQ ID NO 3
<211> LENGTH: 1296
<212> TYPE: DNA
<213> ORGANISM: Artificial Sequence
<220> FEATURE:
<223> OTHER INFORMATION: Synthetic

<400> SEQUENCE: 3
atggcaccga aacgtaaagc gagtagtacc tgcaaaaccc cgaaacgtca gtgtattccg      60
aaaccgggtt gttgtccgaa cgttgcaagc gttccgaaac tgctggttaa aggcggcgtt     120
gaagttctga gcgtagttac cggcgaagat agcatcaccc agatcgaact gtacctgaac     180
ccgcgtatgg gcgttaatag tccggatctg ccgaccacca gtaattggta tacctacacc     240
tatgatctgc agccgaaagg tagtagtccg gatcagccga tcaaagaaaa cctgccggca     300
tattctgttg cacgcgtttc tctgccgatg ctgaacgaag atatcacctg cgataccctg     360
cagatgtggg aagcaatcag cgtcaaaacc gaagtcgtcg gtattagcag cctgatcaac     420
```

```
gtccactact gggatatgaa acgcgtccac gattatggcg caggtattcc ggtttctggc        480
gtcaactacc acatgtttgc aattggcggc gaaccgctgg atctgcaagg cctggttctg        540
gattaccaga ccgaataccc gaaaaccacc aacggcggtc cgattaccat tgaaaccgtt        600
ctgggccgca aaatgacccc gaaaaatcag ggtctggatc cgcaagcaaa agcgaaactg        660
gacaaagacg gcaactaccc gatcgaagtt tggtgtccgg atccgagcaa aaacgagaac        720
agccgttatt acggcagcat tcaaaccggt agtcaaaccc cgaccgttct gcagtttagt        780
aacaccctga ccaccgttct gctggacgaa aacggtgttg gtccgctgtg taaaggcgac        840 ggcctgtttta ttagctgcgc ggatattgtc ggcttcctgt tcaaaacctc cggcaaaatg        900
gcactgcacg gtctgccgcg ttattttaac gttaccctgc gcaaacgctg ggttaaaaac        960
ccgtatccgg tcgttaacct gattaacagc ctgttctcca acctgatgcc gaaagtttcc       1020
ggtcaaccga tggaaggcaa agataaccag gtcgaagaag tccgtattta cgaaggcagc       1080
gaacaactgc cgggcgatcc ggatattgta cgtttcctgg acaaattcgg gcaggagaaa       1140
accgtttatc cgaaaccgtc agttgcaccg gcagcagtta cctttcagag caatcagcag       1200
gacaaaggta aagcaccgct gaaaggtccg cagaaagcaa gccagaaaga aagccagacc       1260
caggaactgc tcgagcacca ccaccaccac cactga                                 1296
```

```
<210> SEQ ID NO 4
<211> LENGTH: 1272
<212> TYPE: DNA
<213> ORGANISM: Artificial Sequence
<220> FEATURE:
<223> OTHER INFORMATION: Synthetic

<400> SEQUENCE: 4
```

```
atggcaccga acgtaaagc gagtagtacc tgcaaaaccc cgaaacgtca gtgtattccg         60
aaaccgggtt gttgtccgaa cgttgcaagc gttccgaaac tgctggttaa aggcggcgtt        120
gaagttctga gcgtagttac cggcgaagat agcatcaccc agatcgaact gtacctgaac        180
ccgcgtatgg gcgttaatag tccggatctg ccgaccacca gtaattggta tacctacacc        240
tatgatctgc agccgaaagg tagtagtccg gatcagccga tcaaagaaaa cctgccggca        300
tattctgttg cacgcgtttc tctgccgatg ctgaacgaag atatcacctg cgataccctg        360
cagatgtggg aagcaatcag cgtcaaaacc gaagtcgtcg gtattagcag cctgatcaac        420
gtccactact gggatatgaa acgcgtccac gattatggcg caggtattcc ggtttctggc        480
gtcaactacc acatgtttgc aattggcggc gaaccgctgg atctgcaagg cctggttctg        540
gattaccaga ccgaataccc gaaaaccacc aacggcggtc cgattaccat tgaaaccgtt        600
ctgggccgca aaatgacccc gaaaaatcag ggtctggatc cgcaagcaaa agcgaaactg        660
gacaaagacg gcaactaccc gatcgaagtt tggtgtccgg atccgagcaa aaacgagaac        720
agccgttatt acggcagcat tcaaaccggt agtcaaaccc cgaccgttct gcagtttagt        780
aacaccctga ccaccgttct gctggacgaa aacggtgttg gtccgctgtg taaaggcgac        840 ggcctgtttta ttagctgcgc ggatattgtc ggcttcctgt tcaaaacctc cggcaaaatg        900
gcactgcacg gtctgccgcg ttattttaac gttaccctgc gcaaacgctg ggttaaaaac        960
ccgtatccgg tcgttaacct gattaacagc ctgttctcca acctgatgcc gaaagtttcc       1020
ggtcaaccga tggaaggcaa agataaccag gtcgaagaag tccgtattta cgaaggcagc       1080
gaacaactgc cgggcgatcc ggatattgta cgtttcctgg acaaattcgg gcaggagaaa       1140
accgtttatc cgaaaccgtc agttgcaccg gcagcagtta cctttcagag caatcagcag       1200
```

```
gacaaaggta aagcaccgct gaaaggtccg cagaaagcaa gccagaaaga aagccagacc     1260
caggaactgt aa                                                         1272
```

```
<210> SEQ ID NO 5
<211> LENGTH: 423
<212> TYPE: PRT
<213> ORGANISM: Artificial Sequence
<220> FEATURE:
<223> OTHER INFORMATION: Synthetic

<400> SEQUENCE: 5

Met Ala Pro Lys Arg Lys Ala Ser Ser Thr Cys Lys Thr Pro Lys Arg
1               5                   10                  15

Gln Cys Ile Pro Lys Pro Gly Cys Cys Pro Asn Val Ala Ser Val Pro
                20                  25                  30

Lys Leu Leu Val Lys Gly Gly Val Glu Val Leu Ser Val Val Thr Gly
            35                  40                  45

Glu Asp Ser Ile Thr Gln Ile Glu Leu Tyr Leu Asn Pro Arg Met Gly
        50                  55                  60

Val Asn Ser Pro Asp Leu Pro Thr Thr Ser Asn Trp Tyr Thr Tyr Thr
65                  70                  75                  80

Tyr Asp Leu Gln Pro Lys Gly Ser Ser Pro Asp Gln Pro Ile Lys Glu
                85                  90                  95

Asn Leu Pro Ala Tyr Ser Val Ala Arg Val Ser Leu Pro Met Leu Asn
                100                 105                 110

Glu Asp Ile Thr Cys Asp Thr Leu Gln Met Trp Glu Ala Ile Ser Val
            115                 120                 125

Lys Thr Glu Val Val Gly Ile Ser Ser Leu Ile Asn Val His Tyr Trp
        130                 135                 140

Asp Met Lys Arg Val His Asp Tyr Gly Ala Gly Ile Pro Val Ser Gly
145                 150                 155                 160

Val Asn Tyr His Met Phe Ala Ile Gly Gly Glu Pro Leu Asp Leu Gln
                165                 170                 175

Gly Leu Val Leu Asp Tyr Gln Thr Glu Tyr Pro Lys Thr Thr Asn Gly
            180                 185                 190

Gly Pro Ile Thr Ile Glu Thr Val Leu Gly Arg Lys Met Thr Pro Lys
            195                 200                 205

Asn Gln Gly Leu Asp Pro Gln Ala Lys Ala Lys Leu Asp Lys Asp Gly
        210                 215                 220

Asn Tyr Pro Ile Glu Val Trp Cys Pro Asp Pro Ser Lys Asn Glu Asn
225                 230                 235                 240

Ser Arg Tyr Tyr Gly Ser Ile Gln Thr Gly Ser Gln Thr Pro Thr Val
                245                 250                 255

Leu Gln Phe Ser Asn Thr Leu Thr Thr Val Leu Leu Asp Glu Asn Gly
            260                 265                 270

Val Gly Pro Leu Cys Lys Gly Asp Gly Leu Phe Ile Ser Cys Ala Asp
            275                 280                 285

Ile Val Gly Phe Leu Phe Lys Thr Ser Gly Lys Met Ala Leu His Gly
        290                 295                 300

Leu Pro Arg Tyr Phe Asn Val Thr Leu Arg Lys Arg Trp Val Lys Asn
305                 310                 315                 320

Pro Tyr Pro Val Val Asn Leu Ile Asn Ser Leu Phe Ser Asn Leu Met
                325                 330                 335

Pro Lys Val Ser Gly Gln Pro Met Glu Gly Lys Asp Asn Gln Val Glu
```

-continued

```
            340               345               350
Glu Val Arg Ile Tyr Glu Gly Ser Glu Gln Leu Pro Gly Asp Pro Asp
        355               360               365
Ile Val Arg Phe Leu Asp Lys Phe Gly Gln Glu Lys Thr Val Tyr Pro
    370               375               380
Lys Pro Ser Val Ala Pro Ala Ala Val Thr Phe Gln Ser Asn Gln Gln
385               390               395               400
Asp Lys Gly Lys Ala Pro Leu Lys Gly Pro Gln Lys Ala Ser Gln Lys
            405               410               415
Glu Ser Gln Thr Gln Glu Leu
        420
```

```
<210> SEQ ID NO 6
<211> LENGTH: 1272
<212> TYPE: DNA
<213> ORGANISM: Artificial Sequence
<220> FEATURE:
<223> OTHER INFORMATION: Synthetic

<400> SEQUENCE: 6
atggcaccaa aaagaaaagc atcatccacc tgtaaaacac ccaaaaggca atgtatacct     60
aagccgggat gctgccctaa tgttgcctca gttccaaaac tgcttgttaa aggaggagtg    120
gaagtattat ctgtggttac tggagaagat agcattaccc aaattgagtt gtatttgaat    180
ccaagaatgg gagttaattc ccctgatctt cctactactt caaactggta tacttatact    240
tatgacctgc agccaaaggg atcatctcca gatcagccca tcaaggaaaa tttgccagct    300
tacagtgtgg caagagtgtc tctgccaatg ctaaatgagg atattacctg tgacacattg    360
cagatgtggg aggcaatatc tgttaaaaca gaagtagttg gaataagttc tttaattaat    420
gttcattatt gggacatgaa aagagttcat gattacggtg ctggtattcc tgtgtcaggg    480
gtaaattacc atatgtttgc cattggggga gaacctctgg atttgcaagg cctagtttta    540
gattaccaga ctgagtatcc aaaaaactaca aatggtgggc ctattacaat tgaaactgta    600
ttgggaagaa aaatgacacc taaaaatcag ggcctagatc cacaagctaa agcaaaatta    660
gataaagatg gaaattatcc tatagaagta tggtgtcctg atccttctaa aaatgaaaac    720
agtagatact atgggtctat tcagacaggc tctcagactc ctacagttct tcaatttagt    780
aatactctaa ctactgtcct tttagatgag aatggagtgg gccctctatg caaaggagat    840
ggcctattta ttagctgtgc agacatagtg gggtttctgt ttaaaaccag tggaaaaatg    900
gctcttcatg ggttgcctag atattttaat gttactttga gaaaaagatg ggtgaaaaac    960
ccctacccag tagttaattt aataaactct ctcttcagca acttaatgcc aaaagtgtca   1020
ggccaaccta tggaaggaaa agataatcag gtagaagagg ttagaatata tgaggggtca   1080
gaacaattac ctggtgatcc tgatattgtc agattttag ataaatttgg gcaggagaaa   1140
actgtttacc caaagccctc tgttgcccca gcagcagtaa cattccaaag taatcagcag   1200
gataagggca aggcgccact gaaaggacct caaaaggcct ctcaaaaaga aagccaaaca   1260
caagaattat ga                                                      1272
```

```
<210> SEQ ID NO 7
<211> LENGTH: 25
<212> TYPE: DNA
<213> ORGANISM: Artificial Sequence
<220> FEATURE:
<223> OTHER INFORMATION: Synthetic
```

-continued

<400> SEQUENCE: 7
ctagagctag cgtttaaact taagc                                           25

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
gcggccgctc tagactcgag tcacagctcc tg                                   32

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gtggaggtgc tgtccgtggt g                                               21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
caggaagccc acgatatcgg c                                               21

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Arg Met Gly Val Asn Ser Pro Asp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Ser Ser Leu Ile Asn Val His Tyr Trp
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Val Ser Gly Val Asn Tyr His Met Phe
1               5

-continued

```
<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Arg Trp Val Lys Asn Pro Tyr Pro Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Leu Ile Asn Ser Leu Phe Ser Asn Leu
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Glu Asn Leu Pro Ala Tyr Ser Val Ala Arg Val Ser Leu Pro Met
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Leu Pro Ala Tyr Ser Val Ala Arg Val Ser Leu Pro Met Leu Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Arg Val His Asp Tyr Gly Ala Gly Ile Pro Val Ser Gly Val Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Lys Thr Val Tyr Pro Lys Pro Ser Val Ala Pro Ala Ala Val Thr
1               5                   10                  15
```

-continued

```
<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Val Tyr Pro Lys Pro Ser Val Ala Pro Ala Ala Val Thr Phe Gln
1               5                  10                  15
```

VACCINE FOR PREVENTING AND TREATING MERKEL CELL CARCINOMA

RELATED APPLICATIONS

The present application is a United States National Phase under 35 U.S.C. § 371 of International Application No. PCT/CN2021/127386, filed on Oct. 29, 2021, which claims the benefit of Chinese National Patent Application No. 202011276594.0, filed Nov. 16, 2020.

SEQUENCE LISTING

The instant application contains a Sequence Listing which has been filed electronically in ASCII format and is hereby incorporated by reference in its entirety. Said ASCII copy, created on May 1, 2023, is named 112147-0018-70001US00_SUBSEQ.txt and is 15,960 bytes in size.

TECHNICAL FIELD

The present invention belongs to the fields of immunology and virology, and particularly relates to a novel vaccine for preventing and treating Merkel cell carcinoma.

BACKGROUND

Merkel cell polyomavirus (MCV) is currently the only polyomavirus that is clearly known to be directly related to human cancer. Merkel cell polyomavirus is a double-stranded non-enveloped DNA virus with an icosahedral globular structure of about 45 nm, has a genome size of 5386 bp, and contains an early coding region, a late coding region, and a non-coding regulatory region (NCRR). The early genes of Merkel cell polyomavirus mainly encode LT, ST, 57kT, and ALTO (alternate Large T open reading frame), while the late genes mainly encode capsid proteins VP1 and VP2. VP1 has the function of initiating viral infection and is usually present as a pentamer. Seventy-two pentamers can self-assemble into virus-like particles in eukaryotic systems.

Merkel cell carcinoma is a rare invasive skin cancer that prevails in sites exposed to sunlight, such as head and neck, and appears as rapidly growing purple-red nodules. Merkel cell polyomavirus incorporated into the tumor cells can be detected in tumors in about 80% of the patients with Merkel cell carcinoma (MCC). Meanwhile, antibodies specific to Merkel cell polyomavirus capsid protein VP1 can be detected in about 60-80% of healthy people. Merkel cell polyomavirus infects human young children mainly in an asymptomatic manner. Ultraviolet irradiation and hypoimmunity caused by diseases or aging both are causes of the onset of Merkel cell carcinoma. Merkel cell carcinoma has a low incidence, but a very poor clinical prognosis, and is one of the most lethal tumors of cutaneous origin. The most commonly used treatment is chemotherapy or surgical resection, although the recurrence rate is as high as 40%. In recent years, with the rise and wide application of immune checkpoint inhibitors (PD-L/PD-L1 inhibitors), some monoclonal antibodies have been applied to the treatment of advanced metastatic Merkel cell carcinoma. However, this treatment method relies heavily on the autoimmunity of patients, and the response rate varies greatly for different individuals. The importance of vaccines, the most successful disease intervention measures in medical history, is self-evident. Recombinant virus-like particle (VLP) vaccines, which do not contain viral genetic materials but have a morphological structure similar to that of natural viruses, combine safety with good immunogenicity. Thus, they are used in various fields as prophylactic vaccines, such as human papilloma virus (HPV) and hepatitis A/B/E virus. Meanwhile, animal experiments have shown that the virus-like particle vaccines can be therapeutic against constructed papillomas without the administration of any adjuvant. Based on this, for Merkel cell polyomavirus VP1 capable of self-assembling into virus-like particles, the development of related vaccines based on this protein has shown great potential in the prevention or treatment of Merkel cell polyomavirus.

In the prior art, development of related vaccines has been carried out for VP1 of different viruses.

For example, Chinese patent No. 200810232479.6 discloses a gene of B19 virus VP1 unique region, constructs a cloning plasmid B19 for prokaryotic expression of a pQE30-VP1 unique region, and obtains a recombinant protein by expression and purification, wherein the recombinant protein can cause an immune cell response in vitro and produce antibodies with high titers.

For example, Chinese patent No. 201010126145.8 discloses a codon-optimized EV71 VP1 gene and a nucleic acid vaccine thereof, wherein the vaccine can be effectively expressed in eukaryotic 293T cells, and can immunize animals to stimulate the production of specific VP1 antibodies. However, the vaccine only adopts nucleic acid as the active ingredient of the vaccine and has poor immune effect.

For the clearance of the Merkel cell polyomavirus-infected cells or the Merkel cell carcinoma cells, the synergistic effect of neutralizing antibodies with $CD4^+/CD8^+$ T cells in vivo is essential. Although higher titers of antibodies specific for Merkel cell polyomavirus VP1 are observed in patients with Merkel cell carcinoma than in healthy humans, relevant clinical data suggest that high levels of anti-VP1 antibodies are predictive of a better clinical prognosis.

Based on the wide infection rate of Merkel cell polyomavirus and the high lethality rate of Merkel cell carcinoma, further intensive research on Merkel cell carcinoma is extremely important and has practical significance.

SUMMARY

Terminology

Unless otherwise defined, all the technical and scientific terms used herein have the same meaning as commonly understood by those of ordinary skill in the art to which the present invention belongs.

The following terms used herein have the following meanings.

Unless otherwise clearly stated in the context, the singular forms "a", "an", and "the" as used herein and in the appended claims all include plural referents. Likewise, the terms "a" (or "an"), "one or more", and "at least one" are used interchangeably herein. The terms "comprising", "including", and "having" are used interchangeably.

The term "vaccine" as used herein refers to a composition that can be administered to a human or animal to induce an immune system response, which may result in the production of antibodies or the activation of only certain cells, particularly antigen-presenting cells, T lymphocytes, and B lymphocytes. The vaccine composition may be a composition for prophylactic purposes or for therapeutic purposes, or a composition for both prophylactic and therapeutic purposes.

The term "administration" as used herein refers to their ordinary and common meaning in the art of treating patients with vaccines or certain compositions. The terms "co-administration" and "concomitant administration" as used herein are synonyms and refer to the administration of two substances or two compositions to a patient in such a way that both substances or both compositions are present in the patient. Meanwhile, co-administration may be simultaneous or sequential, and the substances or compositions for co-administration may be administered to the patient simultaneously, or separately but in close time proximity, or on the same day, or in other ways that result in significant overlap of the residence time of the substances or compositions in the body. The administration, parenteral injection, may include subcutaneous, intramuscular, intradermal, intraperitoneal, intraocular, intranasal, and intravenous administrations.

The vaccine or composition involved in the present invention may be administered to an individual according to methods known in the art. These methods include parenteral administration, for example, by injection through or into the skin by all routes of injection, such as intramuscular, intravenous, intraperitoneal, intradermal, mucosal, submucosal, or subcutaneous injection. In addition, the vaccine may be administered topically as a drop, a spray, a gel, or an ointment to the mucosal epithelium of the eye, nose, mouth, anus or vagina, or to the outer epidermis of any part of the body. Other possible routes of administration are inhalation of a spray, aerosol or powder through the respiratory tract. In the last case, the size of the particles used will determine the depth of entry of the particles into the respiratory tract. Alternatively, it may be administered by the digestive route in the form of a powder, a liquid, or a tablet in combination with food, feed, or drinking water, or directly to the oral cavity in the form of a liquid, gel, tablet, or capsule, or to the anus in the form of a suppository. In one example, the DNA vaccine may be delivered by using an electrical pulser or any electroporation device to facilitate penetration of the DNA vaccine into the host cells and efficient expression.

When the term "about" is used before numerical expression (such as temperature, time, amount, and concentration, inclusive), it means that an approximation of (+) or (−) 10%, 5%, or 1% is possible.

The term "against" as used herein refers to words of "treatment", "prevention", "adjuvant therapy" or equivalent words, and combinations thereof in the field of vaccines.

The term "against Merkel cell carcinoma" as used herein is to be considered without limitation as against Merkel cell polyomavirus.

The terms "treatment" and "prevention" and words derived therefrom as used herein do not necessarily mean 100% or complete treatment or prevention. Rather, varying degrees of treatment or prevention by certain technical means in the art are considered to have potential benefits or therapeutic effects. In one example, the composition or method of the present invention may provide any dose or level of disease treatment or prevention in a mammal. In addition, the treatment or prevention provided by the method of the present invention may include treatment or prevention of one or more disorders or symptoms of a disease or cancer. Also, for purposes herein, "prevention" may include delaying the onset of a disease or a symptom or condition thereof. With respect to the method of the present invention, the cancer may be any cancer, including any cancer related to any tumor antigen described herein.

The term "adjuvant" as used herein refers to an agent that, when used in combination with a particular immunogen in a formulation (e.g. a VLP-based vaccine), will alter or modify the immune response either in an enhanced or reduced tendency. Modification of the immune response includes enhancement or expansion of a specific antibody or cellular immune response, one or both of which are included within the scope. Modification of the immune response may also refer to the reduction or suppression of certain antigen-specific immune responses.

The term "virus-like particle" or "VLP" as used herein refers to a non-replicating virus particle. Expression of viral structural proteins (such as envelope or capsid proteins) under specific conditions can lead to self-assembly of VLPs. VLPs are generally composed of one or more viral proteins, such as, but not limited to, those referred to as capsid, coat, shell, surface and/or envelope proteins, or polypeptides formed from particles derived from these proteins. VLPs may be formed spontaneously upon recombinant expression of the protein in an appropriate expression system. Methods for producing particular VLPs are known in the art and will be discussed more fully below. The presence of VLPs upon recombinant expression of viral proteins can be detected by conventional techniques known in the art, e.g., by electron microscopy, biophysical characterization, and the like. See Baker et al., *Biophys. J.* (1991) 60:1445-1456; Hagensee et al., *J. Virol.* (1994) 68:4503-4505. For example, VLPs may be identified by density gradient centrifugation and/or by characteristic density bands. Alternatively, a vitrified aqueous sample of the VLP formulation discussed may be examined using cryo-electron microscopy and images are recorded under appropriate exposure conditions. Other VLP purification methods include, but are not limited to, chromatographic techniques such as affinity, ion exchange, size exclusion, and reverse phase processes. In addition, any nano-measurement device may be used to measure the size of nanoparticles.

The present invention further relates to variants of a polynucleotide and a polypeptide. The term "variant" as used herein refers to a polynucleotide or polypeptide that differs from the polynucleotide or polypeptide of the present invention but retains its essential properties. In general, variants are very similar overall and, in many regions, identical to the polynucleotide or polypeptide of the present invention.

The variants may contain changes in either or both the coding region and the non-coding region. The variants of a polynucleotide that produce silent substitutions, additions or deletions, but do not alter the properties or activity of the encoded polypeptide are mostly preferred. Among them, nucleotide variants resulting from silent substitutions due to the degeneracy of the genetic code are preferred. In addition, variants in which 5 to 10, 1 to 5, or 1 to 2 amino acids are substituted, deleted or added in any combination are frequently present.

An example of a variant is a truncation, and an example of a truncation is an MCV-VP1 truncation, which may include a C-terminal 55aa (369-423) deletion. The C'-deletion from wild-type MCV-VP1 can result in an MCV-VP1 truncation with an aa1-369 fragment, which can act with other antigens on chimeric VLP fusion proteins.

An example of a variant is a deletion, and an example of a deletion is the C-terminal 17aa (352-368) deletion of MCV-VP1.

An example of a variant is a mutation, and an example of a mutation is the E353 mutation of MCV-VP1, i.e., replacement with L or F.

The present invention further includes allelic variants of the polynucleotide. An allelic variant refers to any one of two or more alternative forms of a gene occupying the same chromosomal locus. Allelic variants arise naturally through mutation and may result in polymorphism within a population. Gene mutations may be silent (no change in the encoded polypeptide) or may encode polypeptides with altered amino acid sequences. An allelic variant of a polypeptide is a polypeptide encoded by an allelic variant.

The present invention further relates to polynucleotide fragments containing or hybridizing to the non-coding region of MCV VP1. The polynucleotide fragments may be polynucleotide fragments of equal length to or shorter length than naturally occurring nucleotides. Such fragments can be used for diagnosis. Polynucleotide fragments containing cleavage sites or hybridizing with polynucleotides containing cleavage sites are often present. Polynucleotide fragments of any length, e.g., 50, 150, 500, 600, 1000, 1100, or about 1260 nucleotides, can be used.

The present invention constructs a VP1-based DNA and/or protein vaccine against Merkel cell polyomavirus by cloning an optimized cDNA sequence of the structural protein VP1 of Merkel cell polyomavirus (MCV) in a eukaryotic system and a prokaryotic system, and expressing the VP1 protein in a prokaryotic system. The DNA vaccine for immunization alone against the Merkel cell carcinoma or the protein vaccine for immunization alone against the Merkel cell carcinoma provided by the present invention can induce a cellular immune response or high levels of anti-VP1 antibodies. This study is the first to use VP1 as a vaccine antigen against Merkel cell polyomavirus, laying the foundation for studies on vaccines against Merkel cell carcinoma.

Unless otherwise indicated, "vehicle" herein refers to "PBS", and "OVA" refers to "ovalbumin".

Unless otherwise indicated, "VP1" or "recombinant protein VP1" herein refers to "recombinant Merkel cell polyomavirus capsid protein", and "rVP1", or "recombinant or self-assembling VP1" refers to "recombinant or self-assembling Merkel cell polyomavirus capsid protein".

In one aspect, the present invention provides a vaccine composition against Merkel cell carcinoma, wherein the vaccine composition comprises: Merkel cell polyomavirus capsid protein VP1 or a plasmid comprising a gene encoding the Merkel cell polyomavirus capsid protein VP1; and a TLR agonist selected from one or more of CpG, R848, and MPL. The composition comprising the Merkel cell polyomavirus capsid protein VP1 is a protein vaccine composition. The composition comprising the plasmid comprising the gene encoding the Merkel cell polyomavirus capsid protein VP1 is a DNA vaccine composition.

In some preferred embodiments of the present invention, the TLR agonist is a combination of CpG and R848.

In some preferred embodiments of the present invention, the composition further comprises an aluminum-based adjuvant. In some preferred embodiments of the present invention, the vaccine composition comprises 5-500 parts by weight of the Merkel cell polyomavirus capsid protein VP1 or the plasmid comprising the gene encoding the Merkel cell polyomavirus capsid protein VP1, 2.5-250 parts by weight of the TLR agonist, and 10-1000 parts by weight of the aluminum-based adjuvant.

In some preferred embodiments of the present invention, the vaccine composition comprises 10-100 parts by weight of the Merkel cell polyomavirus capsid protein VP1 or the plasmid comprising the gene encoding the Merkel cell polyomavirus capsid protein VP1, 5-100 parts by weight of the TLR agonist, and 50-500 parts by weight of the aluminum-based adjuvant.

In some preferred embodiments of the present invention, the VP1 comprises a nucleotide sequence having 71.9%-74.7% homology to SEQ ID No. 6.

In some preferred embodiments of the present invention, the VP1 comprises a nucleotide sequence set forth in SEQ ID No. 1, SEQ ID No. 2, SEQ ID No. 3, or SEQ ID No. 4.

In another aspect, the present invention provides an encoding gene of Merkel cell polyomavirus capsid protein VP1.

Specifically, the encoding gene comprises a nucleotide sequence having 71.9%-74.7% homology to SEQ ID No. 6.

Specifically, the encoding gene comprises a nucleotide sequence set forth in SEQ ID No. 1, SEQ ID No. 2, SEQ ID No. 3, or SEQ ID No. 4.

In another aspect, the present invention further provides use of the encoding gene of Merkel cell polyomavirus capsid protein VP1 in preparing a vaccine against Merkel cell carcinoma.

Specifically, the use is the preparation of a DNA vaccine against Merkel cell carcinoma by using one or more of a nucleotide sequence having 71.9%-74.7% homology to SEQ ID No. 6, or variants thereof.

Specifically, the use is the preparation of a DNA vaccine against Merkel cell carcinoma by using one or more of nucleotide sequences set forth in SEQ ID No. 1, SEQ ID No. 2, SEQ ID No. 3, or SEQ ID No. 4, or variants thereof.

Specifically, the use is the preparation of a protein vaccine against Merkel cell carcinoma by using one or more of proteins and/or mutants thereof encoded by the nucleotide sequence having 71.9%-74.7% homology to SEQ ID No. 6, and/or variants thereof.

Specifically, the use is the preparation of a protein vaccine against Merkel cell carcinoma by using one or more of proteins and/or mutants thereof encoded by the nucleotide sequence set forth in SEQ ID No. 1, SEQ ID No. 2, SEQ ID No. 3, or SEQ ID No. 4, or variants thereof, further specifically, the proteins comprise, but are not limited to, an amino acid sequence of SEQ ID No. 5.

Specifically, the use is the preparation of a vaccine against Merkel cell carcinoma by simultaneously using the nucleotide sequence having 71.9%-74.7% homology to SEQ ID No. 6, and/or variants thereof, and one or more of the proteins and/or mutants thereof encoded by the nucleotide sequences.

Specifically, the use is the preparation of a vaccine against Merkel cell carcinoma by simultaneously using the nucleotide sequence set forth in SEQ ID No. 1, SEQ ID No. 2, SEQ ID No. 3, or SEQ ID No. 4, or variants thereof, and one or more of the proteins and/or mutants thereof encoded by the nucleotide sequences.

Further specifically, the use includes, but is not limited to, the preparation of a vaccine against Merkel cell carcinoma by using the amino acid sequence of SEQ ID No. 5.

In yet another aspect, the present invention provides a vaccine against Merkel cell carcinoma.

Specifically, the vaccine is a DNA vaccine.

Specifically, the DNA vaccine comprises one or more of a nucleotide sequence having 71.9%-74.7% homology to SEQ ID No. 6, and/or variants thereof.

Specifically, the DNA vaccine comprises one or more of a nucleotide sequence of SEQ ID No. 1, SEQ ID No. 2, SEQ ID No. 3, or SEQ ID No. 4, and/or variants thereof.

Specifically, the DNA vaccine is constructed on a vector, wherein the vector includes, but is not limited to a pVAX1 vector, pcDNA3.1, NTC8385, or a viral vector, such as adenovirus Ad vector and adeno-associated virus AAV vector.

Specifically, the protein vaccine comprises one or more of proteins and/or mutants thereof encoded by the nucleotide sequence having 71.9%-74.7% homology to SEQ ID No. 6, and/or variants thereof.

Specifically, the protein vaccine comprises one or more of proteins and/or mutants thereof encoded by SEQ ID No. 1, SEQ ID No. 2, SEQ ID No. 3, or SEQ ID No. 4, and/or variant nucleotide sequences thereof.

Further specifically, the proteins encoded by SEQ ID No. 1, SEQ ID No. 2, SEQ ID No. 3, or SEQ ID No. 4 comprise, but are not limited to, an amino acid sequence of SEQ ID No. 5.

As a recommended and non-limiting administration method, the DNA vaccine is injected in an amount of 1-200 µg/mouse.

As a recommended and non-limiting preparation method, the protein vaccine may be prepared by using an *E. coli* system to generate a VP1 protein to form DNA-free virus-like particles (VLPs) of different sizes, for example, by self-assembly.

As a recommended and non-limiting preparation method, the protein vaccine may be prepared by using protein expression systems from other biological species, including but not limited to, yeast expression systems, baculovirus expression systems, Chinese Hamster Ovary (CHO) expression systems, and the like.

As a recommended and non-limiting preparation method, the virus-like particles in the protein vaccine are purified before forming the protein vaccine.

As a recommended and non-limiting preparation method, the VP1 protein virus-like particles has a size between about 1 nm and about 1 m, about 5 nm and about 800 nm, about 8 nm and about 700 nm, about 10 nm and about 400 nm, about 20 nm and about 200 nm, about 25 nm and about 100 nm, or about 30 nm and about 50 nm; in one embodiment, the VP1 protein virus-like particle has a size more concentrated between about 20 nm and about 200 nm, about 25 nm and about 100 nm, or about 30 nm and about 50 nm.

The vaccine further comprises an adjuvant comprising a TLR agonist and an aluminum-based adjuvant, wherein the TLR agonist is selected from one or more of CpG, R848 and MPL.

Preferably, the vaccine comprises 5-500 parts by weight of the DNA vaccine or the protein vaccine, 2.5-250 parts by weight of the TLR agonist, and 10-1000 parts by weight of the aluminum-based adjuvant.

Further preferably, the vaccine comprises 10-100 parts by weight of the DNA vaccine or the protein vaccine, 5-100 parts by weight of the TLR agonist, and 50-500 parts by weight of the aluminum-based adjuvant.

As a recommended and non-limiting administration method, the protein vaccine is injected in an amount of 1.1-20 µg/mouse.

Specifically, the vaccine is a prophylactic and/or therapeutic vaccine.

Specifically, the vaccine provided by the present invention is suitable for use in any mammal. The mammal is a warm-blooded vertebrate, including but not limited to a human, a rabbit, a cat, a dog, a pig, cattle, and a dog.

Specifically, the vaccine or the product containing the vaccine involved in the present invention may be in dosage forms including but not limited to a drop, a spray, a gel, a powder, an ointment, a tablet, or a granule.

BRIEF DESCRIPTION OF THE DRAWINGS

Figure 15:
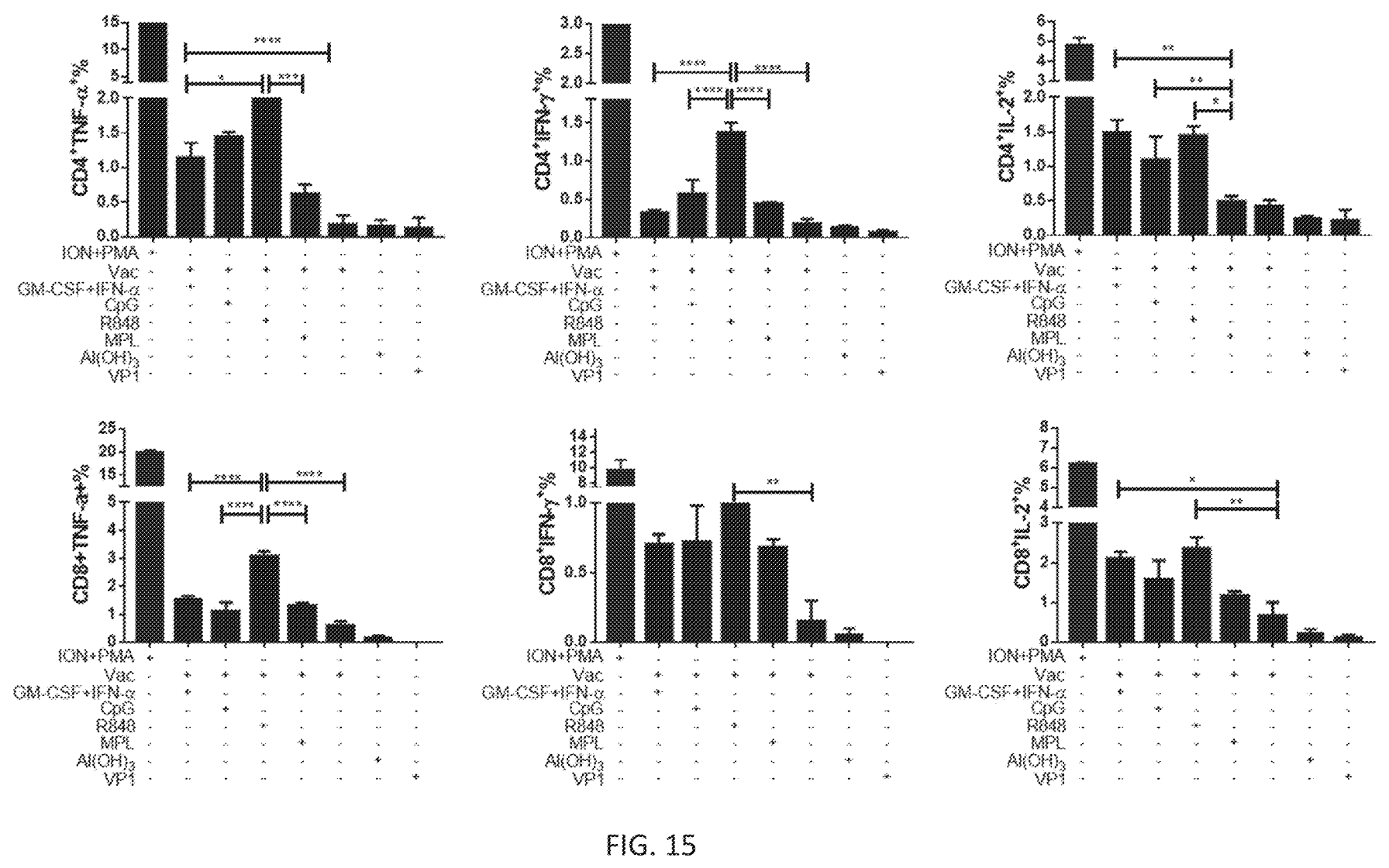

FIG. 15 shows the flow cytometry assay results of the expression levels of TNF-α, IFN-γ, and IL-2 in CD4$^+$ and CD8$^+$ T cells of the mice after immunization with adjuvant-containing therapeutic vaccines in Example 13.

DETAILED DESCRIPTION

Figure 1:
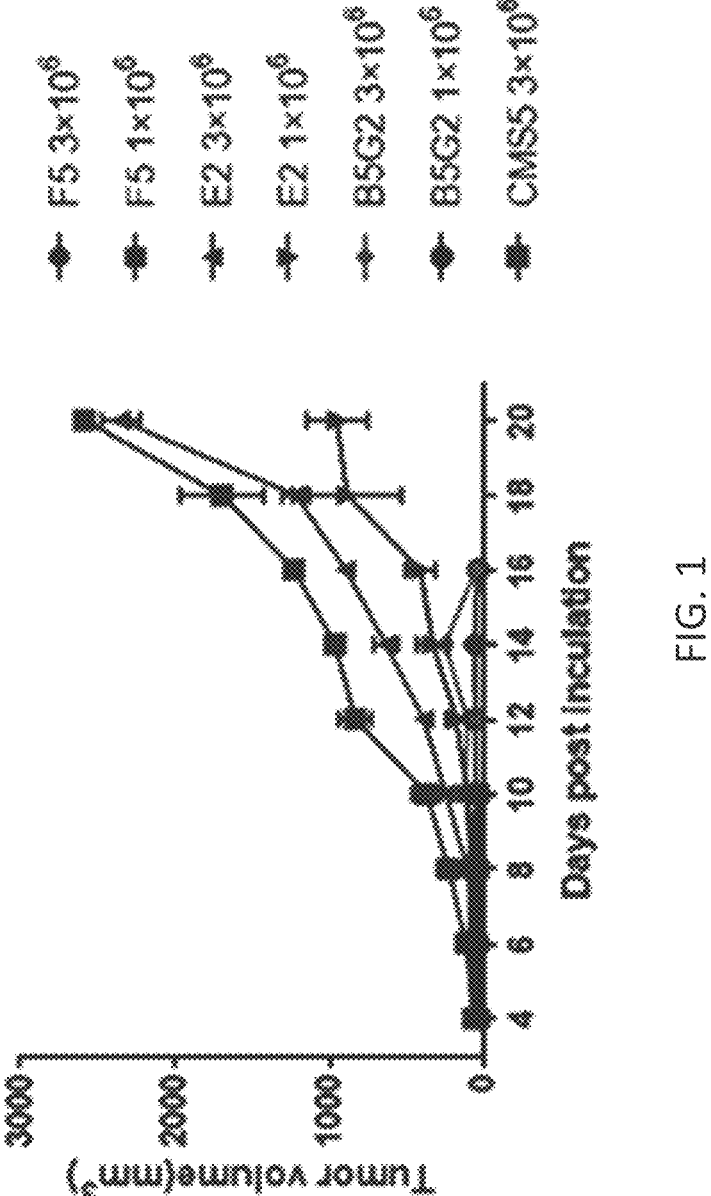
FIG. 1 is a graph showing the tumor growth curves of a CMS5-VP1 cell line in Basic Experimental Example 1.

The present invention will be described in further detail with reference to specific examples, which are not intended to limit the present invention, but to illustrate the present invention. Unless otherwise stated, the experimental methods used in the following examples, and the experimental methods without specific conditions indicated in the examples, are generally performed under conventional conditions. Unless otherwise stated, the materials, reagents, and the like used in the following examples are commercially available.

Basic Experimental Example 1. Construction, Screening, and Verification of CMS5-VP1 Tumor Cell Strain The CMS5-VP1 tumor cell strain is mainly applied to verification of vaccine effect.

1. Construction of pcDH-VP1 Plasmid (1) Primers were First Designed According to the pcDH-GFP Plasmid:

```
MCV-F
                                    (SEQ ID NO: 7)
(5'-CTAGAGCTAGCGTTTAAACTTAAGC-3');
and MCV-R
                                    (SEQ ID NO: 8)
(5'-GCGGCCGCTCTAGACTCGAGTCACAGCTCCTG-3').
```

The 5' end of MCV-F contains an Nhe I restriction enzyme cutting site, and the 3' end of MCV-R contains a Not I restriction enzyme cutting site.

(2) PCR Amplification

Amplification was performed with the plasmid pVAX1-VP1 as a template to obtain a VP1 fragment containing restriction endonuclease sites at both the N terminus and the C terminus. The PCR reaction system is shown in Table 1 below.

TABLE 1

| Reagent dosage for PCR reaction | |
| --- | --- |
| Component | Volume |
| pVAX1-VP1 | 1 μL |
| MCV-F(20 μM) | 2 μL |
| MCV-R(20 μM) | 2 μL |
| Taq(5 u/μL) | 1 μL |
| dNTP(2.5 mM each) | 4 μL |
| 10 × buffer | 5 μL |
| Deionized water | 35 μL |

The PCR reaction program is shown in Table 2 below.

TABLE 2

| PCR reaction program | | |
| --- | --- | --- |
| 98° C. | 3 min | |
| 98° C. | 30 s | |
| 54° C. | 30 s | 28 cycles |
| 72° C. | 90 s | |
| 72° C. | 10 min | |

(3) Enzyme Digestion Reaction

The VP1 fragment obtained by PCR amplification and the vector pCDH were digested with endonuclease Nhe I/Not I in a water bath at 37° C. for 4 h, and the VP1 fragment and the pcDH vector were recovered. The enzyme digestion system is shown in Table 3 below.

TABLE 3

| Double digestion reaction system | |
| --- | --- |
| Reagent | Volume |
| VP1 fragment/pcDH | 30 μL |
| Nhe I | 2 μL |
| Not I | 2 μL |
| 10 × BSA | 5 μL |
| 10 × H buffer | 5 μL |
| Deionized water | 6 μL |

(4) Enzymatic Ligation and Transformation Reactions

The VP1 and pcDH fragment products recovered after enzyme digestion were subjected to a ligation reaction at room temperature for 40 min by using T4 ligase according to a molar mass ratio of 1:3.

The ligation products were transformed into *E. coli* cloning host strain DH5a competent cells by a chemical transformation method. The specific procedures were as follows:

1) The ligation product was uniformly mixed with 50 μL of DH5α competent cells, and left to stand in an ice bath for 30 min.

2) The heat shock was performed for 90 s at 42° C.

3) The mixture was left to stand on ice for 3 min.

4) 500 μL of antibiotic-free LB fluid medium was added.

5) The mixture was cultured with shaking on a shaker at 150 rpm for 45 min at 37° C.

6) The mixture was centrifuged at 13,000 rpm, and the supernatant was discarded.

7) The bacteria were resuspended in 100 μL of antibiotic-free LB liquid medium, and an LB plate containing ampicillin (50 μg/mL Amp) was coated with the bacteria, cultured in an inverted state in an incubator at 37° C. overnight, and labeled pcDH-VP1/DH5α.

(5) Colony PCR Identification and Sequencing

Six monoclonal colonies of pcDH-VP1/DH5α were randomly picked from the plate cultured overnight for PCR identification using 2×PCR Mix. The specific procedures were as follows:

1) 10 μL of 2×PCR Mix was placed in each sterile PCR tube, and 0.2 μL of primers MCV-F and MCV-R were separately added.

2) Monoclonal colonies were picked from the plate with 10 μL of Tip and uniformly pipetted into 11 μL of sterile deionized water with a pipettor.

3) A new LB (50 μg/mL Amp) plate was taken, with grids drawn on the bottom and with clone number labeled and cultured in an inverted state in an incubator at 37° C. for 10 h.

4) The pcDH-VP1/DH5α bacterial solution obtained by uniformly pipetting was spotted on the corresponding positions of the LB plate.

5) The remaining pcDH-VP1/DH5αbacterial solution was added to 2×PCR Mix containing primers, and PCR was performed under the same conditions as in the (2) PCR amplification in the step 1 described above.

6) After the PCR was completed, the PCR product was detected by 1% agarose gel electrophoresis.

(6) Sequencing Identification

Based on the PCR results, PCR-positive clones were picked and cultured in 5 mL of LB liquid medium (50 μg/mL Amp) with shaking at 37° C. overnight.

1 mL of each of pcDH-VP1/DH5α monoclonal bacterial solution cultured overnight was sequenced with the universal primers CMV-F and EF1α-R. The remaining bacterial solution was mixed with 60% sterile glycerol at a ratio of 3:1 and cryopreserved at −20° C. for later use.

Sequence alignment was performed according to the sequencing results to determine the clone number with the correct sequence, and the glycerol stock with the correct sequence was cryopreserved at −80° C.

(7) Preparation of pcDH-VP1 Plasmid

One tube of pcDH-VP1/DH5α cryopreserved at −80° C. was inoculated into 200 mL of LB liquid medium (50 μg/mL Amp) at a ratio of 1:100 and cultured with shaking on a shaker at 220 rpm overnight at 37° C., and pcDH-VP1 plasmids were extracted with an Endofree Plasmid Maxi Kit (QIAGEN, 12362).

Experimental Results:

1 μL of PCR product obtained by PCR amplification with the plasmid pVAX1-VP1 as a template was taken and detected by 1% agarose gel electrophoresis, and the size of a target band obtained by PCR amplification was consistent with the theoretical size. The VP1 fragment was recovered using a PCR Purification Kit (QIAGEN, 28104).

The recovered VP1 fragment and the vector pcDH-GFP were digested with Nhe I/Not I, and the digestion products were subjected to 1% agarose gel electrophoresis.

The gel bands containing VP1 and pcDH were cut under an ultraviolet lamp, and the target fragment was recovered with a Gel Extraction Kit (QIAGEN, 28115). The recovered VP1 and pcDH were subjected to an enzymatic ligation reaction according to the reaction system shown in Table 4 below.

TABLE 4

| Enzymatic ligation reaction system | |
| --- | --- |
| Reagent | Volume |
| VP1 | 12.5 μL |
| pcDH | 2 μL |
| T4 ligase | 1 μL |
| 10 × ligation buffer | 2 μL |
| Deionized water | 2.5 μL |

After the enzymatic ligation reaction, the products were transformed into E. coli DH5α competent cells and labeled pcDH-VP1/DH5α. Ten monoclonal colonies were randomly picked for colony PCR. In order to further determine the constructed pcDH-VP1, positive clones were sequenced to identify clones with the correct sequence.

The pcDH-VP1/DH5α glycerol stock was inoculated into 200 mL of LB (50 μg/mL) liquid medium at a ratio of 1:100, and cultured with shaking at 37° C. overnight, and the extracted plasmids were used to construct a CMS5-VP1 cell line.

2. Construction of CMS5-VP1 Cell Line

CMS5 cells are a fibrosarcoma cell line produced by drug-induced BALB/c mice. CMS5 cells are adherent cells. CMS5 cells are not resistant to puromycin per se, and a puromycin-resistant gene carried by the vector pcDH is integrated into the cell genome to confer puromycin resistance to the cells. Therefore, pcDH-VP1 is transfected into CMS5 cells by a lipofection method, and CMS5 cells which are not transfected with pcDH-VP1 died in large numbers under the drug pressure of puromycin, so that the cell line CMS5-VP1 expressing VP1 is obtained by screening.

(1) Determination of Puromycin Drug Concentration

In order to determine the killing dose of puromycin to CMS5, CMS5 cells were cultured in RPMI1640 (10% FBS, 1% diabody) complete media with different concentrations of puromycin. 24 h later, cells were stained with trypan blue and observed under a microscope for mortality to determine the drug concentration for 100% lethality of CMS5 cells as the drug pressure for CMS5-VP1 cell line screening. The specific procedures were as follows:

1) CMS5 cells cryopreserved in a liquid nitrogen container were thawed in a water bath at 37° C., 10 mL of RPMI1640 serum-free medium was added, and the mixture was centrifuged at 1000 rpm for 5 min.

2) The supernatant was removed, the cells were resuspended in 10 mL of RPMI1640 complete medium and added to a 10 cm cell culture dish, which was cultured in an incubator at 37° C. with 5% $CO_2$.

3) When CMS5 cells grew to cover 80% of the dish, the medium was removed, and 2 mL of sterile 1×PBS was added to immerse the cells in the culture dish.

4) PBS was removed, 1 mL of trypsin was added, and the cells were digested in an incubator at 37° C. with 5% $CO_2$ for 30 s.

5) After the digestion with trypsin was stopped by adding 5 mL of RPMI1640 complete medium, the mixture was centrifuged at 1000 rpm for 5 min.

6) The supernatant was removed, and the cells were resuspended in 5 mL of RPMI1640 complete medium. 2.5 mL of cell suspension was uniformly mixed with 7.5 mL of RPMI1640 complete medium and added to a 10 cm cell culture dish, which was cultured in an incubator at 37° C. with 5% $CO_2$. This is the cell thawing and 1:2 subculture.

7) After 4 subcultures in this way, the CMS5 cells in good condition were digested with trypsin and prepared into a cell suspension with an RPMI1640 complete medium.

8) The CMS5 cell suspension was plated on a 12-well plate at $1×10^6$/well and cultured in an incubator at 37° C. with 5% $CO_2$ overnight.

9) After the cells were adhered to the wall, the media were replaced with RPMI1640 complete media containing 0.25 μg/mL, 0.5 μg/mL, 1 μg/mL, 2 μg/mL, 5 μg/mL, 10 μg/mL, and 20 μg/mL puromycin, respectively. After 24 h of culture, the CMS5 cells digested with trypsin were stained with trypan blue and the lethality of the cells was calculated microscopically to determine the final puromycin drug concentration.

(2) Transfection of pcDH-VP1 by Lipofection Method

The pcDH-VP1 plasmids were transfected into CMS5 cells by the lipofection method. After 48 h of transfection, cells carrying the target plasmid were selected by puromycin drug pressure, and stably expressed cell strains were selected by long-term drug screening. The specific procedures were as follows:

1) CMS5 cells were cultured in an RPMI1640 complete medium in a 150 mm culture dish.

2) When CMS5 cells grew to cover 80% of the culture dish, the cells were digested with trypsin and prepared into a cell suspension with an antibiotic-free RPMI1640 complete medium, and $1×10^7$ CMS5 cells were applied on each of two 10 cm cell culture dishes and cultured in an incubator at 37° C. with 5% $CO_2$ overnight.

3) The CMS5 cells cultured overnight covered approximately 80% of the culture dish.

4) DNA (pcDH-VP1 or pcDH-GFP plasmid) and Lipofectamine2000 were separately diluted in serum-free OPTI-MEM at a ratio of 1:3, and the mixture was left to stand at room temperature for 20 min.

5) The diluted DNA (pcDH-VP1 or pcDH-GFP) was mixed with the diluted Lipofectamine 2000 at a ratio of 1:1, and the mixture was left to stand at room temperature for 5 min.

6) The DNA-Lipofectamine2000 mixture was added to the CMS5 culture dish cultured overnight.

7) After 48 h of transfection, the medium was removed from the plate, an RPMI1640 complete medium containing puromycin was added, and the mixture was cultured in an incubator at 37° C. with 5% $CO_2$. In the early stage of transfection, the cells died in large numbers, and half of the medium was replaced once every 3 days. After the cells had proliferated slowly, all of the medium was replaced once every 3 days.

8) After the cells grew to cover all of the culture dish for the first time, the medium was replaced for subculture.

(3) Gene Identification of CMS5-VP1 Cells

After the cells were subcultured for the first time, RNA was extracted from CMS5-VP1 or CMS5-GFP cells using a kit, and cDNA was obtained by RT-PCR amplification.

PCR amplification was performed using the cDNA obtained by amplification as a template and MCV-F1 and MCV-R1 as primers.

The PCR amplification result was detected by 1% agarose gel electrophoresis.

(4) Screening of CMS5-VP1 Cell Strain

After 6 rounds of drug pressure screening, CMS5-VP1 cells were subjected to monoclonal cell screening. The specific procedures were as follows:

1) CMS5-VP1 cells were digested with trypsin, stained with Trypan blue, and counted under a microscope on a blood counting chamber.

2) According to the cell count results, CMS5-VP1 cells were diluted to a density of 5 cells/mL with an RPMI1640 complete medium containing puromycin.

3) CMS5-VP1 cell dilution was added to a 96-well cell plate at 100 μL/well to ensure a density of 0.5 cells/well. The cells were cultured in an incubator at 37° C. with 5% $CO_2$.

4) The RPMI1640 complete medium (puromycin) in the 96-well plate was replaced once every three days.

5) When the cells grew into one round spot, the cells were digested with trypsin, diluted again to a density of 5 cells/mL, and subjected to a second round of monoclonal cell screening in a 96-well cell culture plate at 100 μL/well (0.5 cells/well).

6) When the cells grew into one round spot, the cells were digested with trypsin and transferred to a 24-well cell culture plate for culture.

7) The medium was replaced once every three days, and half of the medium was replaced for the first time. After all of the culture dish was covered, the cells were digested with trypsin and transferred to a 12-well cell culture plate for expansion culture.

8) The medium was replaced once every three days, and half of the medium was replaced for the first time. When all of the 12-well plate was covered, the cells were transferred to a 6-well plate for culture.

9) After the 6-well cell culture plate was covered, half of the cells were taken and cryopreserved at –80° C. in a cell cryopreservation solution (90% FBS, 10% DMSO). The other half of cells were transferred to a 10 cm cell culture dish for culture (medium replacement once every three days). The cells grew to substantially cover the culture dish on day six.

10) After the 10 cm cell culture dish was covered, the cells were digested with trypsin, and $5×10^6$ cells were taken and cryopreserved at –80° C. in a cell cryopreservation solution (90% FBS, 10% DMSO).

(5) Identification of CMS5-VP1 Cells $5×10^6$ cells were taken from the CMS5-VP1 cell strain obtained by two rounds of screening and collected by centrifugation at 1000 rpm for 5 min, and expression of VP1 was detected by western-blot. The specific procedures were as follows:

1) $5×10^6$ cells collected by centrifugation were washed twice with 1×PBS to remove residual medium and collected by centrifugation at 1000 rpm for 5 min.

2) The cells were resuspended in 50 μL of 1× cell lysis buffer and left to stand at 4° C. for 2 h.

3) The mixture was centrifuged at 1000 rpm for 5 min, and the supernatant was obtained.

4) 10 μL of 6× loading buffer was added, and the mixture was boiled for 10 min.

5) 12% SDS-PAGE gel electrophoresis (80 V for 30 min, 120 V for 60 min) was performed.

6) Transmembrane was performed using a PVDF membrane.

7) The PVDF membrane transferred with the proteins was placed in a 1×TBST blocking solution of 5% skim milk powder. The membrane was blocked at room temperature on a horizontal shaker for 1 h at low speed.

8) The membrane was washed with 1×TBST 3 times, each time for 5 min.

9) Primary antibody incubation: anti-VP1 rabbit polyclonal antibody was diluted in 1×TBST of 5% skim milk powder at a ratio of 1:5000, and the PVDF membrane was placed in the primary antibody dilution and incubated at room temperature for 1 h.

10) The membrane was washed with 1×TBST 3 times, each time for 5 min.

11) Secondary antibody incubation: HRP-labeled goat anti-rabbit IgG was diluted in 1×TBST of 5% skim milk powder at a ratio of 1:10000, and the PVDF membrane was placed in the secondary antibody dilution and incubated at room temperature for 1 h.

12) The membrane was washed with 1×TBST 5 times, each time for 5 min.

13) ECL color development (Tanon, 180-501): the substrate reaction solution 1 was mixed with the substrate reaction solution 2 at a ratio of 1:1, and the PVDF membrane was inverted in the ECL reaction solution for chemiluminescence detection.

Experimental Results:

1. Determination of Puromycin Drug Concentration

CMS5 cells were not resistant to puromycin per se, while CMS5-VP1, which was transferred to pcDH-VP1, was puromycin resistant because the vector pcDH carries a puromycin-resistant gene. In order to determine the drug-resistance concentration of CMS5 cells to puromycin, CMS5 cells were cultured in RMPI1640 complete media containing 0.25 μg/mL, 0.5 μg/mL, 1 μg/mL, 2 μg/mL, 5 μg/mL, 10 μg/mL, and 20 μg/mL puromycin, respectively. After 24 h of culture, the state of the cells was observed under a microscope. When the concentration of puromycin reached 5 μg/mL, the cells died in large numbers.

In order to further determine the killing effect of puromycin on CMS5 cells, dead and viable cells of CMS5 cells were counted by trypan blue staining, and when the concentration of puromycin reached 5 μg/mL, 100% of CMS5 cells were dead. Thus, 5 μg/mL puromycin was determined as the drug concentration for CMS5-VP1 cell screening.

2. Screening and Identification of CMS5-VP1 Cells

According to the Lipofectamine2000 operation manual, 10 μg of plasmid pcDH-VP1 or pcDH-GFP and 30 μL of Lipofectamine2000 were diluted in 500 μL of serum-free OPTI-MEM, and after being left to stand at room temperature for 5 min, the diluted pcDH-VP1 was mixed with Lipofectamine2000 and left to stand at room temperature for 20 min.

The DNA-liposome complex of pcDH-VP1 or pcDH-GFP and Lipofectamine 2000 were added to CMS5 cells cultured overnight and uniformly mixed, and the cells were cultured in an incubator at 37° C. with 5% $CO_2$.

After 48 h of transfection, the medium was replaced with an RMPI1640 complete medium containing 5 μg/mL puromycin, and under drug pressure, CMS5 cells died in large numbers and CMS5-VP1 cells were slowly proliferated.

In order to determine whether the transfection of CMS5 was successful, CMS5 was transfected with pcDH-VP1 carrying the reporter gene GFP as a positive control, along with the construction of the CMS5-VP1 cell line. On day 21 after the transfection, the proliferation of CMS5-VP1 or CMS5-GFP cells was observed under a fluorescence microscope, under white light or GFP fluorescence.

GFP protein expressed by CMS5-GFP cells was observed under a fluorescence microscope under drug pressure of 5 μg/mL puromycin. No green fluorescence was observed from CMS5-VP1 cells under a fluorescence microscope. This indicates that the method is feasible for selecting a cell strain stably expressing the target gene.

Meanwhile, $1\times10^7$ CMS5-VP1 or CMS5-GFP cells were taken, from which RNA was extracted, and cDNA was obtained by RT-PCR. In order to determine whether the VP1 gene was integrated into CMS5 cells, primers MCV-F1 (5'-GTGGAGGTGCTGTCCGTGGTG-3') (SEQ ID NO: 9) and MCV-R1 (5'-CAGGAAGCCCACGATATCGGC-3') (SEQ ID NO: 10) were designed to amplify a partial fragment of VP1 with the size of 760 bp.

PCR amplification was performed using CMS5-VP1 or CMS5-GFP cDNA as a template and MCV-F1 and MCV-R1 as primers, with the plasmid pcDH-VP1 as positive control.

The PCR product obtained by amplification were detected by 1% agarose gel electrophoresis for the target gene VP1, and the size of the band obtained by amplification using CMS5-VP1 cDNA as a template was consistent with that of the positive control. Meanwhile, the band 4 was the negative control with CMS5 cDNA as a template, and the band 5 is the result of non-specific amplification of CMS5-GFP.

After six rounds of drug screening, the digested CMS5-VP1 cells were diluted and subjected to two rounds of cell screening, and 5 CMS5-VP1 cell strains expressing VP1 were identified by western-blot. The western-blot results showed that CMS5-VP1/E2 was expressed in the highest level, followed by E4E5. In order to perform a CMS5-VP1 tumorigenesis experiment, cell strains CMS5-VP1/B5G2, F5 and E2 with low, medium and high expression levels were selected for the next step.

3. Tumorigenesis Experiment on CMS5-VP1 Cells

The expression level of VP1 of the CMS5-VP1 cell strains was determined by western-blot, and 3 of the strains were selected for the tumorigenesis experiment. The specific procedures were as follows:

1) CMS5-VP1 cells cultured in an RPMI1640 complete medium (puromycin) and CMS5 cells cultured in an RPMI1640 complete medium were separately digested with trypsin and prepared into a cell suspension.

2) After trypan blue staining, the cells were counted under a microscope on a blood counting chamber.

3) CMS5-VP1 cells were diluted to $1\times10^7$ cells/mL and $3\times10^7$ cells/mL with 1×PBS, respectively, and CMS5 cells were diluted to $3\times10^7$ cells/mL.

4) Female BALB/c mice aged 6-8 weeks were randomly grouped, with 3 mice in each group. The mice were separately injected subcutaneously at the back with $1\times10^6$ or $3\times10^6$ CMS5-VP1 cells, wherein the control group was injected subcutaneously at the back with $3\times10^6$ CMS5 cells.

5) Tumor size was measured every other day, starting on day 4 after tumor cell inoculation.

6) Part of tumor tissue was ground with a 200-mesh copper screen, and digested with trypsin at 37° C. for 30 min.

7) After digestion with trypsin and filtration through a 40-mesh screen, the cells were washed with an RPMI1640 complete medium 3 times.

8) The cells were collected at 1000 rpm and the expression level of VP1 was determined by western-blot.

All experimental data were analyzed statistically using the statistical software GraphPad Prism 6.0 (GraphPad, La Jolla, CA, USA), and the results were expressed as mean±standard mean error (SEM). Differences in data statistics between groups were compared by t-test. Nc (p>0.05) denotes no significant difference, * denotes a significant difference (p<0.05),  denotes a more significant difference (p<0.01), * denotes a very significant difference (p<0.001), and **** denotes an extremely significant difference (p<0.0001).

Based on the identification results by western-blot, three CMS5-VP1 cell strains, i.e., E2, F5 and B5G2, were selected for the tumorigenesis experiment. The inoculation amount used for the CMS5 tumorigenesis experiment in the early stage was $3\times10^6$ cells/mouse. In order to determine the tumorigenesis of the three candidate CMS5-VP1 cell strains and the inoculation amount of CMS5-VP1 cells, CMS5-VP1 cells were examined for tumorigenesis using CMS5 cell mice as a positive control.

Female BALB/c mice aged 6-8 weeks were randomly grouped, with three mice in each group. The mice were separately inoculated subcutaneously with CMS5-VP1 cells in an amount of $1\times10^6$ cells/mouse or $3\times10^6$ cells/mouse, wherein the positive control was inoculated with CMS5 cells in an amount of $3\times10^6$ cells/mouse. Tumor size was measured every two days, starting on day 4 after tumor inoculation. When the tumor grew to 2000 mm³, the mice were euthanized, and tumor tissues were taken for detecting the expression level of VP1.

The tumor volume was calculated according to the tumor volume calculation formula (Tumor volume=L×W²/2 (where L is length and W is width)), and tumor growth curves were generated using GraphPad Prism.

Growth curves are shown in FIG. 1. It can be seen that the tumor in mice inoculated with CMS5-VP1/F5 cells began to regress at day 8 after the inoculation and were completely regressed after day 10. The tumor in mice inoculated with $1\times10^6$ CMS5-VP1/B5G2 cells grew slowly and was completely regressed on day 16 after inoculation; and the tumor in mice inoculated with $3\times10^6$ CMS5-VP1/B5G2 cells began to regress on day 14 and was barely detectable on day 16. CMS5-VP1/B5G2 mice were euthanized, from which tumor tissues were taken, cut into pieces, digested with trypsin for half an hour, and washed with an RPMI160 complete medium three times to collect the tumor cells. $1\times10^7$ tumor cells were taken, lysed in 1 mL of cell lysis buffer at 4° C. for 2 h and centrifuged at 13,000 rpm, and the cell supernatant was collected and cryopreserved at −20° C.

The tumor in mice inoculated with $3 \times 10^6$ CMS5-VP1/E2 cells showed no significant difference in growth trend with CMS5 of the control group and grew rapidly on day 18 and had a tumor volume of >2000 mm$^3$ at day 20, while the tumor in mice inoculated with $1 \times 10^6$ CMS5-VP1/E2 grew relatively slowly and had a tumor size of 1000 mm$^3$ on day 20 after the inoculation. The tumor-bearing mice were euthanized, part of the tumor tissue was digested with trypsin, and the cells were collected. $1 \times 10^7$ tumor cells were lysed in 1 mL of cell lysis buffer at 4° C. for 2 h and centrifuged at 13,000 rpm, and the cell supernatant was collected and cryopreserved at −20° C.

In order to further determine the stability of CMS5-VP1 cells, the lysates of CMS5-VP1/B5G2 and CMS5-VP1/E2 cells were taken for western-blot. The detection results showed that the VP1 protein was expressed in tumor tissues of CMS5-VP1 tumor-bearing mice.

Basic Experimental Example 2. Construction and Expression Verification of MCV-VP1_VP2 Pseudovirus 1. Plasmid Construction The gene for the plasmid pcDNA3.1-VP2 was synthesized by Nanjing GenScript Biotech, inserted into the polyclonal cloning site of the vector pcDNA3.1 by the endonuclease Kpn I/Xho I, and sequenced to determine the correctness of the insertion site. pVAX1-VP1/DH5α and pcDNA3.1-VP2/DH5α glycerol stocks were taken, plated on an LB plate (containing Amp, Kan, or other corresponding antibiotics) by streaking, and cultured in an incubator at 37° C. overnight. Monoclonal clones of pVAX1-VP1/DH5α and pcDNA3.1-VP2/DH5α were picked and added to 5 mL of LB liquid medium (containing Amp, Kan, or other corresponding antibiotics), and cultured with shaking on a shaker at 37° C. overnight. The plasmids were extracted from pVAX1-VP1/DH5α and pcDNA3.1-VP2/DH5α bacterial solutions cultured overnight using a Plasmid MiniKit.

Double digestion was performed by endonuclease Hind III/Xho I at 37° C. for 4 h with the plasmid pcDNA3.1-VP2 as a vector and pVAX1-VP1 as an insert to obtain a linearized vector pcDNA3.1 and a target gene VP1. The enzyme digestion system is shown in the Table 5 below.

TABLE 5

| Double digestion reaction system | |
|---|---|
| Reagent | Volume (μL) |
| pcDNA3.1-VP2/pVAX1-VP1 | 10 |
| Hind III | 1 |
| Xho I | 1 |
| 10 × M buffer | 3 |
| Deionized water | 15 |
| Total volume | 30 |

After the digestion was completed, the 1% agarose gel electrophoresis was performed. The agarose gel electrophoresis results showed that the band size was correct. The gel containing the target band was cut under the irradiation of an ultraviolet lamp, and DNA was recovered using a TIANGEN Gel Extraction Kit. 1 μL of recovered product was detected by agarose gel electrophoresis, and the band size was consistent with the theoretical size.

According to the detection results, an enzyme ligation system was determined, and the enzymatic ligation reaction was performed. The reaction system is shown in the Table 6 below.

TABLE 6

| Enzymatic ligation reaction system | |
|---|---|
| Reagent | Volume (μL) |
| VP1 | 16 |
| pcDNA3.1 | 1 |
| T4 ligase | 1 |
| 10 × T4 ligase buffer | 2 |
| Total volume | 20 |

After 1 h of ligation reaction at room temperature, the enzymatic ligation product was added to 50 μL of DH5α competent cells, and the mixture was left to stand in an ice bath for 30 min, followed by water bath at 42° C. for 90 s. 500 μL of LB liquid medium was added to the cells, and the mixture was cultured with shaking at 37° C. on a shaker at 100 rpm for 30 min, and centrifuged at 13,000 rpm after the culture was completed. The supernatant was discarded, and the bacteria were resuspended in 200 μL of LB liquid medium. An LB plate (containing Amp) was coated with the bacterial solution and cultured in an incubator at 37° C. overnight.

Seventeen monoclonal colonies were randomly picked and subjected to colony PCR with PCR preMix, and the PCR products were detected by agarose gel electrophoresis. Positive colonies were picked and added to 5 mL of LB liquid medium, and the mixture was cultured with shaking on a shaker at 37° C. overnight.

1 mL of the positive clone bacterial liquid cultured overnight was sent for sequencing, and the sequencing primer was a universal primer T7-F/BGH-R. 15% glycerol was added to the remaining bacterial solution, and the mixture was cryopreserved at −20° C. The sequence alignment results showed that the pcDNA3.1-VP1 sequence was correct.

pcDNA3.1-VP1, pcDNA3.1-VP2, and pcDNA3.1-EGFP glycerol stocks were separately taken and added to 100 mL of LB liquid culture medium, cultured with shaking on a shaker at 37° C. overnight, and centrifuged at 8000×g for 30 min. The bacteria were collected.

Plasmids were extracted using a QIAGEN Plasmid Midi Kit, and the plasmid concentration was determined by UV260/280. The plasmid concentration is shown in the Table 7 below.

TABLE 7

| Plasmid concentration | |
|---|---|
| Plasmid | Concentration (mg/μL) |
| pcDNA3.1-VP1 | 1.07 |
| pcDNA3.1-VP2 | 1.05 |
| pcDNA3.1-EGFP | 1.14 |

The plasmids were identified by Hind III/Xho I double digestion, and the digestion identification results showed that the size of a band obtained by double digestion was correct, which indicates that the plasmid is correct.

2. MCV Pseudovirus Packaging

1) MCV Pseudovirus Packaging Condition Exploration

293FT cells were thawed. After being stably cultured, the cells were digested with trypsin and centrifuged at 1000×g for 5 min. The cells were collected and resuspended in 1 mL of DMEM complete medium. 1 μL of cell suspension was taken, subjected to 100-fold dilution, and stained with trypan blue, and the number of the cells was counted under a microscope.

The cells were diluted to $1\times10^6$ cells/mL in a DMEM complete medium according to the cell count results.

The cell dilution was added to a 6-well plate at 2 mL/well and cultured in an incubator at 37° C. with 5% $CO_2$ overnight.

pcDNA3.1-VP1, pcDNA3.1-VP2, and pcDNA3.1-EGFP plasmids were mixed at the ratio shown in Table 8, and co-transfected according to the Lipofectamine 2000 operation manual.

TABLE 8

| | Co-transfection ratio | | |
|---|---|---|---|
| GROUP | pcDNA3.1-VP1(μg) | pcDNA3.1-VP2(μg) | pcDNA3.1-EGFP(μg) |
| 1 | 1.2 | 1.2 | 0.6 |
| 2 | 1.8 | 0.3 | 0.9 |
| 3 | 1.5 | 0.75 | 0.75 |
| 4 | 2.57 | 0.42 | 0 |
| 5 | 0 | 1.5 | 1.5 |
| 6 | 2 | 0 | 1 |

The cells were observed under a fluorescence microscope after 48 h;

Referring to the pseudovirus operation manual, after being digested with trypsin, the cells were washed with PBS and collected, and resuspended in a cell lysis buffer (Brij58), followed by the addition of 0.1% Benzonase. The cells were digested in a $CO_2$ incubator at 37° C. overnight to promote MCV pseudovirus packaging and maturation.

293FT cells cultured in a $CO_2$ incubator at 37° C. were counted, diluted to $1.5\times10^6$ cells/mL, and added to a 96-well cell culture plate at 100 μL/well.

The cell lysate was centrifuged at 5000×g for 10 min, and the supernatant was collected, which was the pseudovirus solution. The pseudoviruses in each group were serially diluted in a 10-fold gradient with a DMEM complete medium in an initial dilution gradient ratio of 1:1000 to obtain 7 gradients.

The pseudovirus dilution in each gradient was added to the 293FT cell 96-well plate cultured overnight at 100 μL/well, with 2 replicate wells set for each gradient, and cultured in a $CO_2$ incubator at 37° C. for 72 h.

The expression of the green fluorescent protein EGFP in each well was observed under a fluorescence microscope.

The results showed that the pseudovirus prepared did not have the ability to infect 293FT cells. The expression intensity of the fluorescent protein was high in the co-transfection process. In order to determine whether the structural protein was expressed, 20 μL of pseudovirus suspension in each group was taken and subjected to western-blot assay with the anti-VP1 mouse serum as a primary antibody.

As can be seen from the western-blot results, VP1 expression was observed in all groups except group 5. In order to determine whether 293FT infection cannot be detected due to too low efficiency of packaging plasmids due to the overexpression of EGFP, other Ds-Red with relatively weak expression intensity is used as a reporter gene for pseudovirus packaging. The co-transfection ratio is shown in Table 9. The expression of the fluorescent protein was observed under a fluorescence microscope 48 h after the co-transfection.

TABLE 9

| | Ratio of co-transfected plasmids | | |
|---|---|---|---|
| GROUP | pcDNA3.1-VP1(μg) | pcDNA3.1-VP2(μg) | pcDNA3.1-EGFP(μg)/Ds-Red |
| 1 | 1.9 | 1.9 | 0.2 |
| 2 | 3.25 | 0.55 | 0.2 |
| 3 | 2.85 | 0.95 | 0.2 |
| 4 | 3.8 | 0 | 0.2 |
| 5 | 0 | 3.8 | 0.2 |
| 6 | 3 | 1 | 0 |

MCV-EGFP and MCV-Ds-Red pseudovirus solutions were obtained according to the pseudovirus operation manual. 293FT cells cultured in a $CO_2$ incubator at 37° C. were counted, diluted to $1.5\times10^6$ cells/mL, and added to a 96-well cell culture plate at 100 μL/well.

The cell lysate was centrifuged at 5000×g for 10 min, and the supernatant was collected, which was the pseudovirus suspension. The pseudoviruses in each group were subjected to a 10-fold serial gradient dilution with a DMEM complete medium in an initial dilution of 1:1000 to obtain 7 gradients.

The pseudovirus dilution in each gradient was added to the 293FT cell 96-well plate cultured overnight at 100 μL/well, with 2 replicate wells set for each gradient, and cultured in a $CO_2$ incubator at 37° C. for 72 h.

The expression of the green fluorescent protein EGFP or the Red fluorescent protein Ds-Red in each well was observed under a fluorescence microscope. The results showed that even the packaged pseudoviruses with weakly expressed Ds-Red as a reporter gene still did not have the ability to infect 293FT cells. The pseudoviruses packaged in $1\times10^7$ cells with a fluorescent protein plasmid Zs-Green as a reporter gene did not have the ability to infect 293FT. Meanwhile, the pseudoviruses were packaged in $1\times10^7$ cells using pE2-GFP and pRwB as reporter genes.

After the pseudovirus packaging and maturation were completed according to the operation manual, the pseudovirus suspension was taken and subjected to a 10-fold serial dilution at an initial dilution of 1:1000 to obtain 7 gradients. The experiment of infecting 293FT cells was performed in a 96-well plate, and the fluorescence intensity in each well was observed. The pseudoviruses with RwB as a reporter gene had a weak ability to infect 293FT.

Example 1. DNA Vaccine Against Merkel Cell Carcinoma

The nucleotide sequence set forth in SEQ ID NO: 1 was cloned into a pVAX1 vector with XbaI and HindIII as restriction enzyme cutting sites.

The specific cloning steps are conventional in the art and are not described herein. The cloning method includes PCR amplification, enzyme digestion, ligation, and relevant steps thereof.

Upon identification, the recombinant vector obtained by successfully cloning the nucleotide sequence set forth in SEQ ID NO: 1 into the pVAX1 vector was named pVAX1-MCV-VP1 according to the conventional nomenclature in the art.

The identification method is a conventional method in the art and is not described herein. The identification method is, for example, double digestion identification or sequencing identification. After XbaI and HindIII double digestion, a DNA band of approximately 1.3 kb was observed.

pVAX1-MCV-VP1 was amplified using a kit conventional in the art, such as Endofree Plasmid Maxi Kit (cat #DP117) from Tiangen Biotech (Beijing) Co., Ltd.

It will be understood by those skilled in the art that either pVAX1-MCV-VP1 obtained directly by cloning or pVAX-MCV-VP1 amplicon obtained by amplification using a kit is the DNA vaccine against Merkel cell carcinoma prepared in this example.

Example 2. DNA Vaccine Against Merkel Cell Carcinoma

The only difference between this example and Example 1 is that the nucleotide sequence set forth in SEQ ID NO: 1 was replaced with a nucleotide sequence set forth in SEQ ID NO: 2, SEQ ID NO: 3, or SEQ ID NO: 4.

Upon identification, the recombinant vectors obtained by successfully cloning the nucleotide sequences set forth in SEQ ID NO: 2, SEQ ID NO: 3, and SEQ ID NO: 4 into the pVAX vectors were named pVAX-MCV-VP1-1, pVAX-MCV-VP1-2, and pVAX-MCV-VP1-3, respectively, according to the conventional nomenclature in the art.

Example 3. Protein Vaccine Against Merkel Cell Carcinoma

1. Preparation Method:

(1) Cloning: the nucleotide sequence set forth in SEQ ID NO: 3, with a 6×His tag attached to its C-terminus, was cloned into a pET28a vector using the endonucleases XhoI and NcoI to obtain His-tagged pET28a-VP1/Rosetta cells, which were then stored in a refrigerator at −80° C. The restriction enzyme cutting sites used for cloning were NcoI and XhoI. The specific cloning steps are not described herein. The cloning method includes PCR amplification, enzyme digestion, ligation, and relevant steps thereof. Upon identification, the recombinant vector obtained by successfully cloning the nucleotide sequence set forth in SEQ ID NO: 3 into the pET28a vector was named pET28a-VP1 according to the conventional nomenclature in the art.

(2) Protein expression: any expression system capable of realizing the protein expression in a prokaryotic system can be used in the expression. The expression system is, for example, BL21 or Rosetta cell expression, and the specific expression steps were performed by referring to the operation manual of BL21 or Rosetta cell, which are not described herein. pET28a-VP1 was transformed into Rosetta cells to obtain pET28a-VP1/Rosetta cells, and single clones of pET28a-VP1/Rosetta cells were inoculated into an LB medium with corresponding resistance and expanded at 37° C. to $OD_{600}=0.6$-0.8. After IPTG-induced culture (induction conditions: 18° C., 1 mM IPTG), the bacteria were collected by centrifugation, disrupted by ultrasonication, and centrifuged, and the supernatant was collected.

(3) Protein purification: the supernatant obtained finally in the step (2) was purified using an AKTA AVANT purification system and a nickel column (QIAGEN), and the specific purification procedures were performed by referring to the product instructions of the purification system and nickel column. The rinse solution system was PBS+0.5 M NaCl+100 mM imidazole, pH 7, which was used for washing impure proteins nonspecifically bound to the nickel column; and the eluent system was PBS+0.5 M NaCl+500 mM imidazole, pH 7, which was used for eluting the target protein to obtain an eluate containing the target protein.

(4) Buffer exchange and in vitro assembly: the eluate containing the target protein obtained in the step (3) was dialyzed and buffer exchanged using a dialysis bag, wherein the dialysis conditions were as follows:

First-step dialysis conditions: performing at 4° C., with the dialysate changed every 6 h, 2 L each time. The dialysates were sequentially PBS+0.5 M NaCl, PBS+0.4 M NaCl, PBS+0.3 M NaCl, PBS+0.2 M NaCl, PBS+0.1 M NaCl, and PBS. The purpose of the dialysis in this step is to remove the excess salt components from the eluate; and obtain a desalted eluate containing the target protein.

Second-step dialysis conditions: the desalted eluate containing the target protein obtained after the first-step dialysis was concentrated, diluted to a protein concentration of 0.1 mg/mL, and dialyzed at room temperature for 15 h under the conditions of 0.5 M ammonium sulfate, 20 mM Tris-base+5% glycerol, and 1 mM calcium chloride, pH=7, followed by dialysis in PBS (pH=7) at 4° C. for 24 h. The recombinant protein was obtained, and concentrated by a conventional concentration method (e.g., using PEG8000 powder) to obtain the protein vaccine VP1 against Merkel cell carcinoma.

Figure 2:
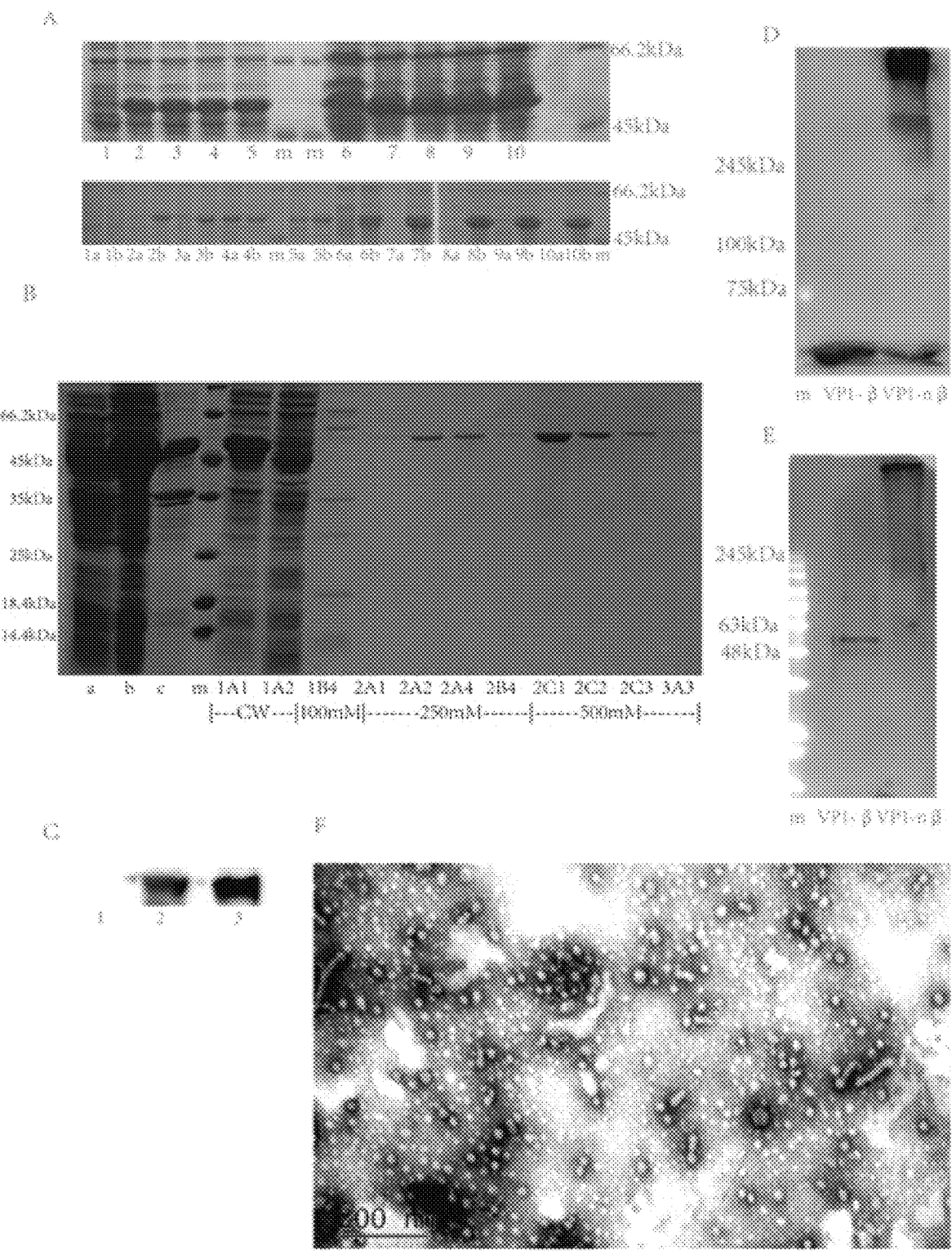
FIG. 2 shows the detection results of the VP1 protein vaccine prepared in Example 3.

2. Verification Experiment:

The performance test was performed on the protein vaccine VP1 prepared in this example. The results are shown in FIG. 2. A shows the soluble expression under different induction conditions: lane 1-18° C., IPTG 0 mM; lane 2-18° C., IPTG 0.1 mM; lane 3-18° C., IPTG 0.5 mM; lane 4-18° C., IPTG 1 mM; lane 5-18° C., IPTG 2 mM; lane 6-30° C., IPTG 0 mM; lane 7-30° C., IPTG 0.1 mM; lane 8-30° C., IPTG 0.5 mM; lane 9-30° C., IPTG 1 mM; lane 10-30° C., IPTG 2 mM; lane a-supernatant protein; lane b-inclusion body protein; lane m-protein marker; B is an electrophoretogram in the nickel column purification process: lane a-mycoprotein; lane b-supernatant protein; lane c-inclusion body protein; lane m-protein marker; lane 100 mM-fractions eluted with 100 mM imidazole; c shows a western-blot analysis, wherein the antibody is anti-His antibody: lane 1-OVA; lane 2-recombinant protein after induction; lane 3-purified recombinant protein; D/E shows a western-blot analysis, wherein the antibody is mouse serum after DNA vaccine immunization; and F is electron microscope observation of the assembled protein vaccine VP1.

In order to determine the optimal conditions for protein expression, different temperatures and IPTG concentrations were used and it was observed that the highest level of soluble VP1 expression could be obtained under the induction condition of 18° C., 1 mM IPTG (A in FIG. 2). After the soluble protein was obtained, it was purified using a nickel column and verified for purity and whether it was the target protein by SDS-PAGE and western-blot (mouse serum after anti-His antibody or DNA vaccine immunization) (B/C/D in FIG. 2).

Although MCV-VP1 can self-assemble into VLPs in eukaryotic systems, and normally the envelope protein VP2 of MCV is involved in this process, it has not been reported that VP1 can self-assemble into VLPs in prokaryotic systems, especially without VP2. Since the assembly of VLPs may be largely influenced by external conditions, mainly including pH, strength of sodium and calcium ions, and the like, different external conditions were used in exploring the in vitro assembly of VLPs in prokaryotic systems. The results of SDS-PAGE showed that the VP1 protein was about 47 kD when the sample was treated with β-mercaptoethanol (β-ME), but exceeded 250 kD in the absence of j-ME treatment (D in FIG. 2), predicting that VLPs consisting of 72 VP1 pentamers may be formed by self-assembly. The assembled protein was subjected to a sucrose density gradient centrifugation and subjected to SDS-PAGE and Western Blot with or without β-ME to further confirm the formation of VLPs (E in FIG. 2). Finally, upon further examination by transmission electron microscopy, VLP particles of different sizes were observed (F in FIG. 2).

In conclusion, the results showed that MCV-VP1 having the nucleotide sequence set forth in SEQ ID NO: 3 could be expressed as a soluble protein in *E. coli* and formed into particles of different sizes by in vitro self-assembly.

Some experimental methods and conditions are exemplified:

Transmission electron microscopy experiment: the recombinant protein (protein vaccine VP1) obtained after final dialysis was subjected to 30%-60% sucrose density gradient centrifugation; samples between the different component layers were then pipetted to verify the position of the target protein after centrifugation. The target protein subjected to the sucrose density gradient centrifugation was stained with a phosphotungstic acid staining solution and observed for the presence of virus-like particles by transmission electron microscopy at a voltage of 80 kV.

SDS-PAGE: the gel concentration was 12%, and the electrophoresis conditions were as follows: for the concentrated gel, 80 V for about 30 min, and for the separation gel, 120 V for about 1 h.

Western-Blot: after the electrophoresis was completed, if the western-blot was not required, the gel was stained with G250 and destained, and then photographed. If the western-blot was required, the protein was transferred to a PVDF membrane; the PVDF membrane was blocked with TBST containing skim milk powder (Tris buffer containing Tween 20) for one hour, incubated in the primary antibody for one hour, and incubated in the secondary antibody for one hour (goat anti-mouse IgG-HRP, dilution 1:4000), both the primary antibody and the secondary antibody were diluted with TBST containing 2% skim milk powder; and the PVDF membrane was treated with a Pro-Light HRP chromogenic solution (Tiangen) for color development.

Example 4. Protein Vaccine Against Merkel Cell Carcinoma

The only difference between this example and Example 3 is that the nucleotide sequence set forth in SEQ ID NO: 3 was replaced with the nucleotide sequence set forth in SEQ ID NO: 1.

Example 5. Establishment of pET28a-VP1/Rosetta Fermentation Process

Nanjing GenScript Biotech was entrusted with gene synthesis and plasmid construction.

In order to obtain a large amount of VP1 recombinant protein, the production was performed in a 10 L fermentation tank. The production specifically comprises the following steps:

1. Seed Culture

1) Glycerol stock streak culture: His-tagged pET28a-VP1/Rosetta glycerol stock prepared in Example 3 were taken out of the refrigerator at −80° C. and thawed at room temperature. In a clean bench, glycerol stock was streaked on an antibiotic LB plate containing 100 μg/mL kanamycin sulfate (Kan) using an inoculating needle and cultured in a constant incubator at 37° C. overnight.

2) Primary seed culture: in a clean bench, one monoclonal colony was taken from the plate, inoculated in 20 mL of LB liquid medium (containing 100 μg/mL Kan), and cultured on a shaker at a rotation speed of 200 rpm for about 16 h at a culture temperature of 37° C.

3) Secondary seed culture: 10 mL of the cultured primary seeds were taken and added to 500 mL of a medium (containing 100 μg/mL Kan) and cultured on a shaker at a rotation speed of 200 rpm for about 3 h at a culture temperature of 37° C. until the $OD_{600}$ was between 1 and 2, for later tank inoculation.

2. Fermentation in a Fermentation Tank

1) After checking the state of components of the fermentation tank, the pH electrode was corrected, and accessories such as a sensor, a pipeline, an adaptor, and a filter were installed.

2) 4 L of tank medium was prepared in the fermentation tank, which was then sterilized at 121° C. for 20 min, with the concentration of dissolved oxygen adjusted to 0 in the sterilization process. After the sterilization, the tank was cooled to 37° C. for tank inoculation.

3. Preparation of the Feeding and Feeding Pipes

A feeding medium with a total volume of 2.5 L was prepared, filled into a feeding flask, and sterilized at 115° C. for 20 min with the feeding pipes and feeding heads. 200 mL of antifoaming agent was prepared and sterilized at 121° C. for 20 min. Ammonia water was poured into a sterile feeding flask for later use.

4. Preparation Before Fermentation Tank Inoculation

1) Kan, trace elements and glucose were added from the inoculation port.

2) The fermentation parameters were tuned and set. The medium was adjusted to pH 7.0 with ammonia water. Value 100 of the dissolved oxygen electrode was corrected, and process parameters were set as follows: 40% DO (concentration of dissolved oxygen); initial rotation speed: 200 rpm; air flow rate: 200 L/h; initial pH: 7.0; and temperature: 37° C.

5. Inoculation 500 mL of cultured secondary seed solution ($OD_{600}$1-2) was inoculated into the fermentation tank, and the inoculation time and $OD_{600}$ value of the strain at the time of inoculation were recorded.

6. Culture Stage 1) pH control: automatically feeding ammonia water to control the pH value to be about 7.0.

2) DO control: greater than or equal to 40%, increasing the rotation speed and gas control when DO was lower than a set value of 40%.

3) Rotation speed control: adjusting the rotation speed according to dissolved oxygen to meet the dissolved oxygen requirement, up to 600 rpm.

4) Foam control: intermittently feeding the antifoaming agent (the feeding principle is to add as little antifoaming agent as possible, as long as the liquid level was controlled to not spray out of the tank).

5) Feeding control: feeding was performed according to dissolved oxygen and pH.

6) Process detection: $OD_{600}$ value was measured hourly and the fermentation situation was recorded.

7. Induction Stage

When $OD_{600}$ reached about 30, 1 mM IPTG was added for induction, which was performed for 4 h with the temperature reduced to 30° C.

8. Tank Fermentation Broth Collection

After 4 h of induction, the tank fermentation broth collected was performed, the fermentation broth was centrifuged for 30 min at 8000 rpm. The supernatant was discarded, and the precipitate was washed twice with sodium phosphate (pH 7.0) buffer and collected for later use. A small amount of bacteria were taken and expression was identified by SDS-PAGE and western-blot.

Experimental Results:

The expression of MCV vaccine antigen VP1 used in the study was induced by IPTG using an *E. coli* prokaryotic expression system. The codon-optimized VP1 was constructed on a prokaryotic expression vector pET28a by molecular cloning technology, the plasmid was named pET28a-VP1, and the correctness of the plasmid was identified by sequencing and enzyme digestion. The pET28a-VP1 plasmid with correct sequence was transformed into *E. coli* expression strain Rosetta competent cells by a chemical method and named pET28a-VP1/Rosetta. The expression strain was inoculated into an LB liquid medium containing 100 g/mL Kan at a ratio of 1:100 and cultured with shaking at 37° C. overnight. The bacterial solution cultured overnight was subpackaged into 1.5 mL sterile centrifuge tubes, with 750 L of bacterial solution and 250 µL of 60% sterile glycerol uniformly mixed in each tube, and cryopreserved at −20° C., which was the MCV-VP1 fermentation seed.

After expansion culture, pET28a-VP1/Rosetta was inoculated into a seed fermentation tank for fermentation culture at 37° C. for 10.5 h, with $OD_{600}$ of 24.9; after the tank was cooled to 30° C., the expression of VP1 protein was induced for 3 h with 0.5 mM IPTG, with $OD_{600}$ of 35.2; the tank was opened, the fermentation broth was collected and centrifuged at 8000 g for 30 min, and the bacteria were collected and weighed to obtain 400 g of wet bacteria.

0.1 g of bacteria were resuspended in 1.5 mL of bacteria disruption buffer and disrupted with a high-pressure homogenizer, and the disruption supernatant and precipitate were separately collected. The precipitate was resuspended in 1.5 mL of lysis buffer for lysis overnight. The lysate was centrifuged, and the supernatant and precipitate were separately collected. After the precipitate was resuspended in 1.5 mL of lysis buffer, 50 µL of disruption supernatant, disruption precipitate, and lysis supernatant were separately taken, 10 µL of 6× loading buffer was added, and the mixture was boiled for 10 min, subjected to 12% SDS-PAGE electrophoresis (100 V for 30 min, 150 V for 60 min), stained with Coomassie brilliant blue for 4 h, and destained with a destaining solution overnight. Meanwhile, the western-blot detection was performed with the anti-His tag mouse polyclonal antibody as a primary antibody, and the HRP-labeled goat anti-mouse IgG as a secondary antibody.

SDS-PAGE electrophoresis results showed that the size of the target protein VP1 was 46 kDa, and lanes 2 and 3 had obvious bands at about 45 kDa. From the SDS-PAGE results, it can be determined that the VP1 expressed after the induction by the fermentation tank at 30° C. mainly forms inclusion bodies. The results of western-blot with an anti-His tag mouse polyclonal antibody as a primary antibody further confirmed that the target protein VP1 mainly forms inclusion bodies.

Example 6. Purification of Recombinant Protein VP1

The VP1 recombinant protein was purified using a nickel ion affinity chromatography column.

1. Bacteria Disruption 10 g of MCV-VP1-expressing bacteria prepared in Example 5 were taken and resuspended in 150 mL of bacteria disruption buffer (0.1 M $NaH_2PO_4$, 20 mM Tris, 0.3 M NaCl, pH 7.0). The bacteria were homogenized for 30 min with a high-pressure homogenizer and centrifuged at 8000×g for 30 min, and the bacteria were collected.

2. Bacterial Lysis

The bacteria were resuspended in 150 mL of lysis buffer (0.1 M $NaH_2PO_4$, 20 mM Tris, 0.3 M NaCl, 8 M urea, pH 7.0), adjusted to pH 7.0, and lysed at 4° C. overnight.

3. Ion Affinity Chromatography Purification

1) The bacteria were centrifuged at 8000×g for 15 min, and the supernatant was collected.

2) 20 mL of Ni-NTA coupled with nickel ions was loaded onto the column and attached to AKATA.

3) After washing with 5 column volumes of deionized water, Ni-NTA was equilibrated with 5 column volumes of equilibration buffer (0.1 M $NaH_2PO_4$, 20 mM Tris, 0.3 M NaCl, 8 M urea, pH 7.0).

4) The lysis supernatant was loaded at a rate of 2 mL/min while the flow-through solution was collected.

5) The column was rinsed with 5 column volumes of washing buffer (0.1 M $NaH_2PO_4$, 20 mM Tris, 0.3 M NaCl, 8 M urea, 20 mM imidazole, pH 7.0) at a flow rate of 5 mL/min while the eluate was collected.

6) The target protein was eluted with eluent (0.1 M $NaH_2PO_4$, 20 mM Tris, 0.3 M NaCl, 8 M urea, 500 mM imidazole, pH 7.0) at a flow rate of 2 mL/min, and the target protein eluted was collected stepwise.

7) The column was rinsed with 0.5 M NaOH at a flow rate of 10 mL/min.

8) The column was washed with deionized water at a flow rate of 10 mL/min.

9) The target protein obtained by elution was detected by SDS-PAGE and western-blot.

Experimental Results:

VP1 expressed by the inclusion body was resuspended in a bacteria disruption buffer and mechanically disrupted with a high-pressure homogenizer, the disruption precipitate was lysed with a lysis buffer containing 8 M urea overnight, and the supernatant obtained by centrifugation was loaded on a nickel ion affinity chromatography column of a GE AKATA prime machine for the purification of VP1.

Figure 3:
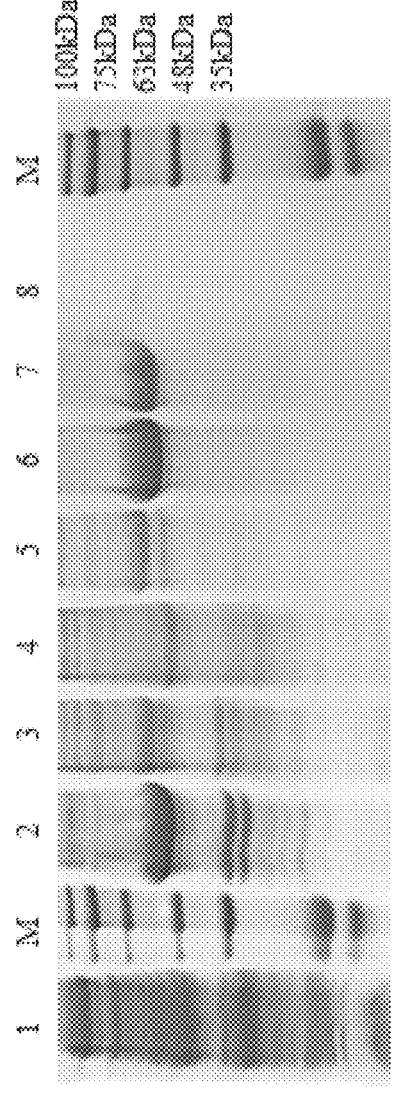
FIG. 3 shows the SDS-PAGE detection results of the purified VP1 protein in Example 6.
Figure 4:
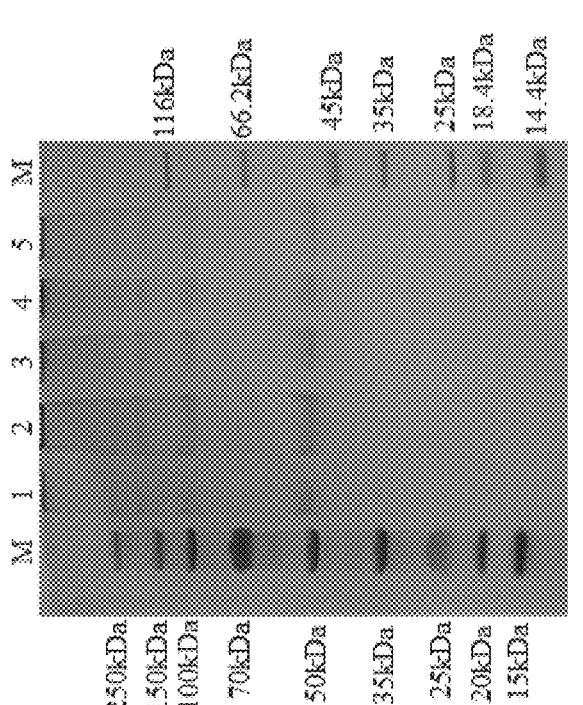
FIG. 4 shows the detection results of VP1 structural proteins formed in different assembly processes by Nu-PAGE in Example 7.

The purified protein was detected by SDS-PAGE. The results are shown in FIG. 3, wherein M represents the protein pre-stained marker (Tiangen Biotech, MP206); 1 is a bacteria disruption supernatant; 2 is a lysis supernatant; 3 is flow-through solution; 4 is 20 mM imidazole washing solution; 5 is 100 mM washing solution; 6 is 250 mM eluent; 7 is 500 mM eluent; 8 is 0.5 M sodium hydroxide washing solution. As can be seen from FIG. 3, the target proteins eluted by 250 mM and 500 mM imidazoles were single bands.

Samples No. 6 and 7 in FIG. 3 were combined and dialyzed with a dialysis bag to gradually remove the urea. After overnight dialysis in a buffer containing 2 M urea, the sample mixture was dialyzed overnight in different dialysis buffers to completely remove urea, so as to renature VP1. The renatured VP1 will spontaneously assemble into protein particles with pentamers as subunits. The following different buffer systems were used for self-assembly by referring to SV40-VP1 or MCV-VP1 assembly conditions reported in the literature.

Buffer 1: 100 mM $NaH_2PO_4$, 20 mM Tris, pH 7.2.

Buffer 2: 100 mM $NaH_2PO_4$, 20 mM Tris, 2 M $(NH_4)_2SO_4$, 2 mM $CaCl_2$), pH 7.2.

Buffer 3: 100 mM $NaH_2PO_4$, 20 mM Tris, 1 M NaCl, pH 7.2.

Buffer 4: 100 mM NaH₂PO₄, 20 mM Tris, 150 mM NaCl, 2 mM CaCl₂), pH 7.2.

Buffer 5: 20 mM MOPS, 0.3 M NaCl, pH 7.0.

Example 7. Study on MCV-VP1 Reassembly Process

This example was intended for further study on the basis of Example 6.

1. Renaturation of the Recombinant Protein VP1

Covalent disulfide bonds play an important role in the formation of higher order structures of proteins. Reducing agents such as DTT and urea in high concentrations can break the false covalent disulfide bonds and ionic bonds, respectively, thereby opening the higher order structure of proteins and allowing the proteins to exist as monomeric molecules. This process is called protein denaturation. When the concentration of reducing agents such as DTT and urea is gradually reduced, disulfide bonds are gradually restored, and the protein can be spontaneously folded to form a high-order structure. This process is called protein renaturation. The VP1 purified under denaturing conditions was renatured by dialysis to gradually remove urea from the protein solution. The specific procedures were as follows:

1) The VP1 solution containing 8 M urea was filled into a dialysis bag and dialyzed in solution 1 (0.1 M NaH₂PO₄, 20 mM Tris, 0.3 M NaCl, 6 M urea, pH 7.0) overnight.

2) The solution was then dialyzed in solution 2 (0.1 M NaH₂PO₄, 20 mM Tris, 0.3 M NaCl, 4 M urea, pH 7.0) overnight.

3) The VP1 protein dialyzed overnight was dialyzed in solution 3 (0.1 M NaH₂PO₄, 20 mM Tris, 0.3 M NaCl, 2 M urea, pH 7.0) overnight.

4) Self-assembly process: the VP1 protein was dialyzed overnight in different assembly buffers to remove urea, at which point VP1 was fully renatured and spontaneously assembled into a VP1 structural protein.

5) The VP1 was detected for pentamer formation by Nu-PAGE. The MCV-VP1 particle size was measured using a nano particle sizer.

2. MCV-VP1 Reassembly

The recombinant protein expressed in the form of inclusion body must be purified under the denaturation condition, and the protein is prone to misfolding in the renaturation process, resulting in the change of protein conformation that affects the protein activity. The disassembly and reassembly processes were as follows:

1) 10 mM DTT and 10 mM EGTA was added to the self-assembled VP1, and the mixture was uniformly mixed on a horizontal shaker for 2 h at low speed. This process is called the disassembly process.

2) The disassembled VP1 protein was filled into a dialysis bag and reassembled under five different reassembly conditions, specifically including:

Buffer 1: 100 mM NaH₂PO₄, 20 mM Tris, pH 7.2.

Buffer 2: 100 mM NaH₂PO₄, 20 mM Tris, 2 M (NH₄)₂SO₄, 2 mM CaCl₂), pH 7.2.

Buffer 3: 100 mM NaH₂PO₄, 20 mM Tris, 1 M NaCl, pH 7.2.

Buffer 4: 100 mM NaH₂PO₄, 20 mM Tris, 150 mM NaCl, 2 mM CaCl₂), pH 7.2.

Buffer 5: 20 mM MOPS, 0.3 M NaCl, pH 7.0.

3) Reassembled (also known as self-assembled) recombinant VP1 was named (rVP1), and rVP1 was filtered through a 0.22 m needle filter for sterilization, detected for the pentamer structure by Nu-PAGE, and measured for the particle size by a nano particle sizer.

Results:

Wild-type MCV is a 72-hedron virus particle composed of VP1 pentamers as the basic unit. It has been reported in the literature that recombinantly expressed polyomavirus capsid protein VP1 also exists in a polymer structure. Whether the VP1 structural protein formed under different assembly processes take pentamers as the basic unit or not was determined by Nu-PAGE. Nu-PAGE electrophoresis detection results are shown in FIG. 4, and 1-5 in FIG. 4 separately represent the assembly of VP1, M and protein non-pre-stained marker under the different reassembly conditions. The results showed that assembled VP1 (rVP1) under different assembly conditions existed in the form of a polymer, in addition to forming a pentamer.

The size of the self-assembled VP1 (rVP1) particles was measured using a Malvern nano particle sizer, and the results showed that self-assembled VP1 (rVP1) structural proteins formed particles of different sizes. In order to obtain stable protein particles, the self-assembled VP1 structural protein was subjected to a disassembly-reassembly process study by using DTT and EGTA, hoping to obtain recombinant protein particles with the particle size closer to that of wild-type MCV by a reassembly process.

3. MCV-VP1 Reassembly (rVP1)

In order to obtain a structural protein with stable particles, after a self-assembled VP1 (rVP1) structural protein was disassembled with 10 mM DTT and 10 mM EGTA, a VP1 reassembly process exploration was performed under different reassembly conditions, and finally the reassembly process under the reductant-oxidant (GSSG-GSH) condition was determined.

VP1 was disassembled, dialyzed in a reassembly buffer (50 mM Tris, 0.8 M (NH₄)₂SO₄, 0.2 M NaCl, 0.5 mM GSH, 4.5 mM GSSG, 2 mM CaCl₂), pH 6.4) for 48 h, and then dialyzed in a buffer (50 mM Tris, 0.2M NaCl, pH 7.0) overnight to remove (NH₄)₂SO₄ and CaCl₂) from the protein solution. Reassembled VP1 (rVP1) was obtained by these processes.

The reassembled VP1(rVP1) was detected by SDS-PAGE and western-blot, and the VP1 pentamer structure was detected by non-reduction electrophoresis. rVP1 showed a unique band under denaturation conditions. The molecular weight of VP1 monomer was 46 kDa and the molecular weight of pentamer was about 250 kDa as detected by Nu-PAGE of ThermoFisher. Therefore, it can be considered that the band at 250 kDa is the VP1 pentamer structure m, and from this result, it is considered that rVP1 obtained by the reassembly process mainly constitutes a protein particle with pentamer as a basic unit.

Meanwhile, the particle size of rVP1 and the soluble VP1 (sVP1) expressed under low-temperature induction was measured by a nano particle sizer, and as a result, the rVP1 particles were more uniform and had the particle size of 115.3 nm compared with VP1 self-assembly particles. However, the particle size of sVP1 was much higher than that of rVP1, which indicates that the presence of reductant-oxidant contributes to the stability of the structure in the reassembly process.

Then, 5 g of wet bacteria were taken to obtain 150 mg of VP1 recombinant protein by the purification process. In this study, 400 g of wet bacteria were obtained by fermentation with 8 L of medium in a 10 L fermentation tank, so that the expression level of VP1 recombinant protein was up to 1.5 g/L.

Example 8. Verification of Immunogenicity of Protein Vaccine

In order to verify the immunogenicity of the protein vaccine VP1 prepared in Example 3, mice were immunized with different doses of the protein vaccine VP1 (1.1 µg/mouse, 3.3 µg/mouse, 10 µg/mouse, and 20 µg/mouse) once every two weeks for a total of two times by aluminum-based adjuvant adsorption and intramuscular injection. The first day of protein vaccine injection was recorded as 0 day.

Figure 5:
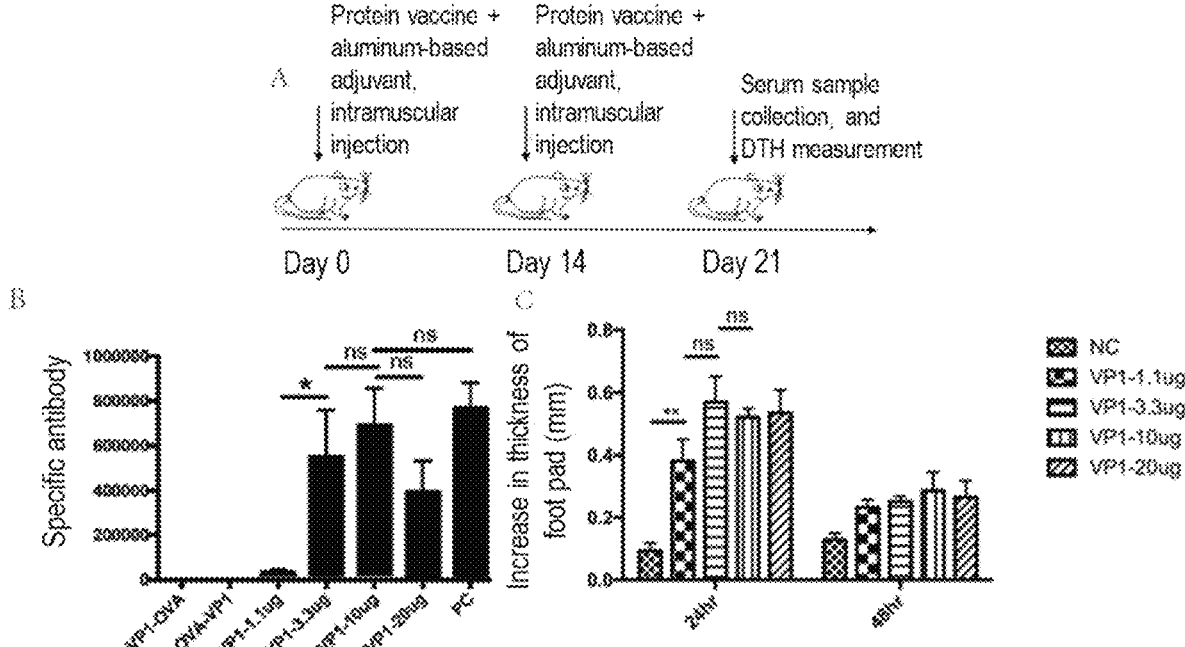
FIG. 5 shows the results of the mouse-specific MCV-VP1 antibody titer, DTH (delayed type hypersensitivity), and cellular immunity in the immunogenicity verification of the protein vaccine VP1 in Example 8.
Figure 5:
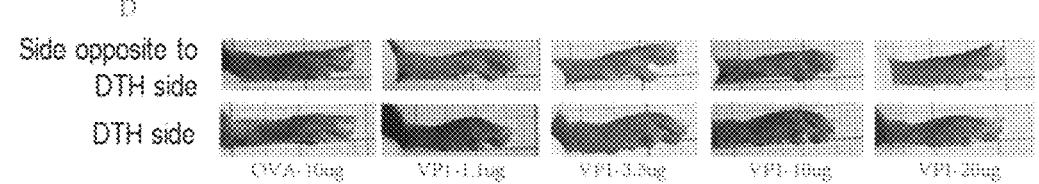
Figure 5:
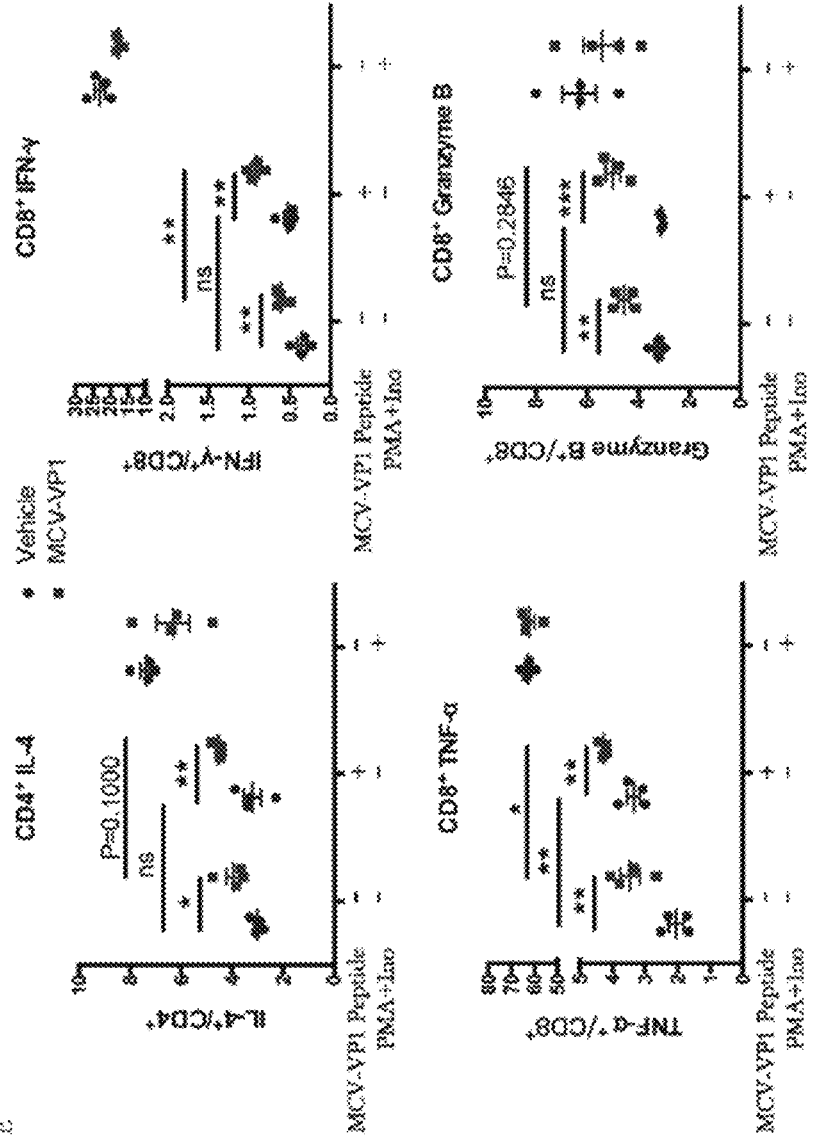

Meanwhile, in order to screen for optimal immunization dose, mouse-specific MCV-VP1 antibody titer was detected and foot pad thickness after DTH (delayed type hypersensitivity) was measured 7 days after the final immunization (B/C/D in FIG. 5). The results showed that: anti-MCV-VP1 specific antibody titer could be detected in the protein vaccine immunization groups at different doses, but the highest antibody titer was observed in the 10 µg group (B in FIG. 5). As can be seen from the DTH results, although the level of DTH was highest in the 3.3 µg group, the level of DTH was relatively high in the 10 µg group (C/D in FIG. 5). Therefore, as can be seen from the combined results of specific antibody levels and DTH, the final dose of 10 µg was selected as the optimal dose of protein vaccine and used in the following experiments (VP1 in the figure refers to the protein vaccine immunization group).

In order to further evaluate the antigen-specific cell responses elicited by the protein vaccine, a VP1-specific peptide pool, MHC-I/MHC-II epitope peptide (MCV-VP1 peptide), was predicted and synthesized, and splenocytes isolated from mice immunized with the protein vaccine were stimulated with this peptide pool. The results showed that the levels of IFN-7 and TNF-α in CD8$^+$ T cells were significantly higher in the protein vaccine immunization group (MCV-VP1) than in the PBS immunization group (Vehicle), and the levels of IL-4 in CD4$^+$ T cells and Granzyme B in CD8$^+$ T cells also showed the same trend of change (E in FIG. 5).

The mice used in this experimental example were BALB/c and C57BL/6 mice aged 6-8 weeks, both purchased from Shanghai Jiesijie Laboratory Animal Co., Ltd. The DNA vaccine was used for immunization by intramuscular injection in combination with electropulsing, and the protein vaccine was used for immunization by intramuscular injection with protein and aluminum-based adjuvant. Some experimental methods or conditions are exemplified below:

Delayed Type Hypersensitivity (DTH): the mice were immunized with the vaccine, and 7 days after the final immunization, 10 µL of antigen protein (10 µg) was injected into the hindfoot pad on the immunized side (right side) of the mice, and 10 µL of phosphate buffer was injected into the hindfoot pad on the side opposite to the immunized side (left side). The thickness of both hindfoot pads of the mice was measured 24 h and 48 h after DTH with a vernier caliper, and the measurement was performed three times at the same site to take the average. DTH value (mm)=right foot pad thickness–left foot pad thickness.

Enzyme-linked immunosorbent assay: on day 21, blood samples were collected from the mice, and the serum was determined for specific antibody titer by ELISA. When the antibody concentration in the mouse serum needs to be semi-quantitatively determined, a standard curve is added on the basis of the conventional ELISA, and the concentration of the antibody in the mouse serum is determined according to the concentration of the standard curve.

Method for Determining sVP1-Specific Antibody Titer by ELISA:

Blood was taken from the fundus of BALB/c mice who have completed the immunization program on day 28 after the initial immunization and left to stand at 4° C. overnight. The blood was centrifuged at 6000 rpm for 10 min to obtain serum. The level of anti-VP1 antibody in serum was determined by ELISA. The specific procedures were as follows:

Coating: rVP1 was diluted to 2 µg/mL with an antigen coating solution, and a 96-well ELISA plate was coated with the antigen dilution at 100 µL/well and incubated at 4° C. overnight.

Blocking: the coating solution was spun off from the 96-well plate coated overnight, which was then washed once with 1×PBST. 1×PBST containing 5% skim milk powder was added at 150 µL/well, and the plate was incubated at 37° C. for 1 h.

Primary antibody dilution: mouse serum was diluted at a dilution of 1:800 with 1× PBST containing 2% skim milk powder and subjected to a serial two-fold dilution to obtain 8 gradients. VP1 rabbit polyclonal antibody was diluted at a dilution of 1:800 with 1×PBST containing 2% skim milk powder and subjected to a serial two-fold dilution to obtain 8 gradients, which were used as positive controls. Serum dilution of 1:800 in Al(OH)$_3$ group was used as a negative control.

Primary antibody incubation: after blocking was completed, the blocking solution was spun off, and the plate was washed 3 times with 1×PBST. After the spin-drying, the diluted mouse serum was added to the 96-well plate at 100 µL/well, with two replicate wells set for each sample. The plate was incubated at 37° C. for 1 h.

Secondary antibody incubation: HRP-labeled goat anti-mouse IgG and HRP-labeled goat anti-rabbit IgG were separately subjected to a 1000-fold dilution with 1×PBST containing 2% skim milk powder. After the primary antibody incubation was completed, the primary antibody was spun off, and the plate was washed 5 times with 1×PBST and spun to dryness. The diluted HRP-labeled goat anti-mouse IgG was added at 100 µL/well, with HRP-labeled goat anti-rabbit IgG added as the positive control. The plate was incubated at 37° C. for 1 h.

Color development: after the secondary antibody incubation was completed, the secondary antibody was spun off. The plate was washed 5 times with 1×PBST and spun to dryness. TMB chromogenic solution was added at 100 µL/well, and the plate was incubated at 37° C. for 5 min.

Stopping: after the color development was completed, 50 µL of 2 M H$_2$SO$_4$ was added.

Reading: the optical absorbance values were read at a wavelength of 450 nm/620 nm with a microplate reader.

Data analysis: a value of 2.1 times the OD value of the negative control group was taken as a cut off value. It was considered positive when the OD value of the sample group was greater than the cut off value, and the dilution of the last positive well of each sample was the antibody titer of that sample.

Spleen cell-specific stimulation: The stimulation was performed in a sterile environment. The mice were euthanized by cervical dislocation 7 days after the final immunization, the spleen was taken and ground to prepare a single cell suspension; the cells were harvested by centrifugation, resuspended in a red blood cell lysis buffer, and lysed, and PBS containing FBS was added to stop the lysis; the lysate was filtered, and the cells were washed with PBS and resuspended in a 1640 complete medium containing anti-CD28 (1:5000 dilution); the cells in the prepared single cell suspension were counted and plated at 1×10$^6$ cells/well; three replicates were set for the sample of each mouse, including a non-stimulation group, a VP1-specific polypeptide stimulation group (MCV-VP1 Peptide), a phorbol ester/ionomycin positive stimulation group (PMA+Ino). The VP1-specific polypeptide pool is shown in Table 10, with a working concentration of 10 μg/mL for the polypeptide, a working concentration of 0.1 μg/mL for PMA, and a working concentration of 1 μg/mL for Ino. Meanwhile, the mixture should contain BFA (Brefeldin A) at a ratio of 1:1000 to inhibit the secretion of cytokines into the extracellular space; the cells were cultured at 37° C. with 5% $CO_2$ for 6 h; the stimulated cells were collected by centrifugation. Detection was performed by flow cytometry.

Figure 6:
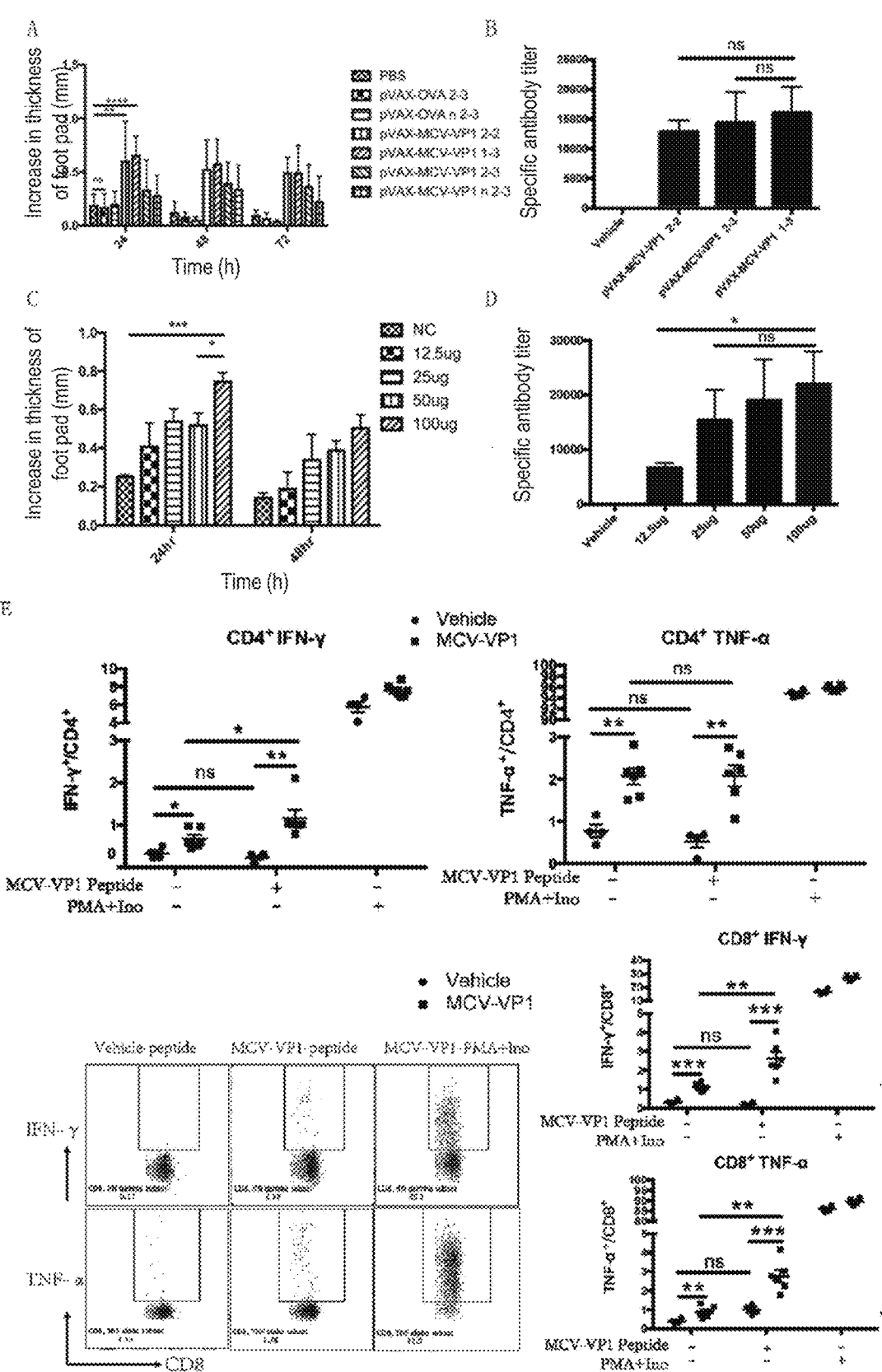
FIG. 6 shows the detection results of immune responses of the DNA vaccine in Example 9.

IFN-7 in CD8$^+$ T cells by about 5-fold (E and F in FIG. 6). The above results showed that the pVAX1-MCV-VP1 DNA vaccine could induce the body to generate a strong VP1-specific cellular immune response.

The verification results of the immune response of the DNA vaccine are shown in FIG. 6. A/B is the optimal immunization strategy study: pVAX1-OVA-2-3 represents the immunization of mice by intramuscular injection of

TABLE 10

| VP1-specific polypeptide pool | | | | |
|---|---|---|---|---|
| Polypeptide site | Allele | Length | Polypeptide sequence | SEQ ID NO |
| MHCI CD8 | | | | |
| 62-70 | H-2-Db | 9 | RMGVNSPDL | 11 |
| 136-144 | H-2-Db | 9 | SSLINVHYW | 12 |
| 158-166 | H-2-Kb | 9 | VSGVNYHMF | 13 |
| 316-324 | H-2-Db | 9 | RWVKNPYPV | 14 |
| 327-335 | H-2-Kb | 9 | LINSLFSNL | 15 |
| MHCII CD4 | | | | |
| 96-110 | H2-IAb | 15 | ENLPAYSVARVSLPM | 16 |
| 98-112 | H2-IAb | 15 | LPAYSVARVSLPmLN | 17 |
| 148-162 | H2-IAb | 15 | RVHDYGAGIPVSGVN | 18 |
| 380-394 | H2-IAb | 15 | KTVYPKPSVAPAAVT | 19 |
| 382-396 | H2-IAb | 15 | VYPKPSVAPAAVTFQ | 20 |

Flow cytometry: live/dead staining: staining on a shaker at room temperature in the dark, using an EF780-APC-Cy7 antibody; cell surface staining: staining procedures were consistent with cell live/dead staining, using a surface antibody staining solution (CD3-FITC/CD4-BV421/CD8-Percp-Cy5.5); intracellular staining: using an Foxp3/transcription factor staining kit (eBioscience); detection was performed by flow cytometer LSRFortssa (Becton).

Example 9. Immune Response of DNA Vaccine

The protein vaccine mainly activates the humoral immune response in the body, and the cellular immune response is relatively weak. Therefore, the DNA vaccine against Merkel cell carcinoma prepared in Example 1 was further verified.

The pVAX1-MCV-VP1 (i.e., DNA vaccine) obtained in Example 1 was used to immunize mice 3 times with a fixed dose of DNA vaccine by intramuscular injection at different time intervals in combination with electropulsing, and it was found that the mice immunized on days 0, 7, and 14 were able to obtain the highest DTH and specific antibody responses (A and B in FIG. 6). In order to determine the optimal immunization dose, various doses from 12.5 μg/mouse to 100 μg/mouse of DNA vaccine were selected, and mice were immunized with a strategy of intramuscular immunization at one-week intervals for a total of three times. The optimal immunization dose was determined to be 100 μg. In addition, after being stimulated by a specific peptide pool, spleen cells of mice immunized with the pVAX1-MCV-VP1 DNA vaccine showed significantly increased levels of IFN-7 in CD4$^+$ T cells and TNF-α in CD4$^+$ T cells, and even more significantly increased level of pVAX1-OVA in combination with electropulsing on days 0, 14, and 28; pVAX1-OVA n 2-3 represents the immunization of mice by intramuscular injection of pVAX1-OVA on days 0, 14, and 28, without electropulsing; pVAX1-MCV-VP1 2-2 represents the immunization of mice by intramuscular injection of pVAX1-MCV-VP in combination with electropulsing on days 0 and 14; pVAX1-MCV-VP1 1-3 represents the immunization of mice by intramuscular injection of pVAX1-MCV-VP1 in combination with electropulsing on days 0, 7, and 14; pVAX1-MCV-VP1 2-3 represents the immunization of mice by intramuscular injection of pVAX1-MCV-VP1 in combination with electropulsing on days 0, 14, and 28; and pVAX1-MCV-VP1 n 2-3 represents the immunization of mice by intramuscular injection of pVAX1-MCV-VP1 on days 0, 14, and 28, without electropulsing during immunization. C/D is the optimal immunization dose exploration. E/F is specific in vitro stimulation of spleen cells.

Example 10. Combined Immune Response

Since the protein vaccine against Merkel cell carcinoma can induce a higher level of specific antibody response and the DNA vaccine can induce a higher level of cellular immune response, whether the combination of the DNA vaccine prepared in Example 1 and the protein vaccine prepared in Example 3 can induce higher levels of both cellular and humoral immune responses is verified in this example.

In order to achieve this purpose, mice were immunized on days 0, 14, and 28, with both the DNA vaccine and the protein vaccine at the corresponding optimal immunization doses obtained by exploration in Examples 8 and 9.

Figures 7, 8:
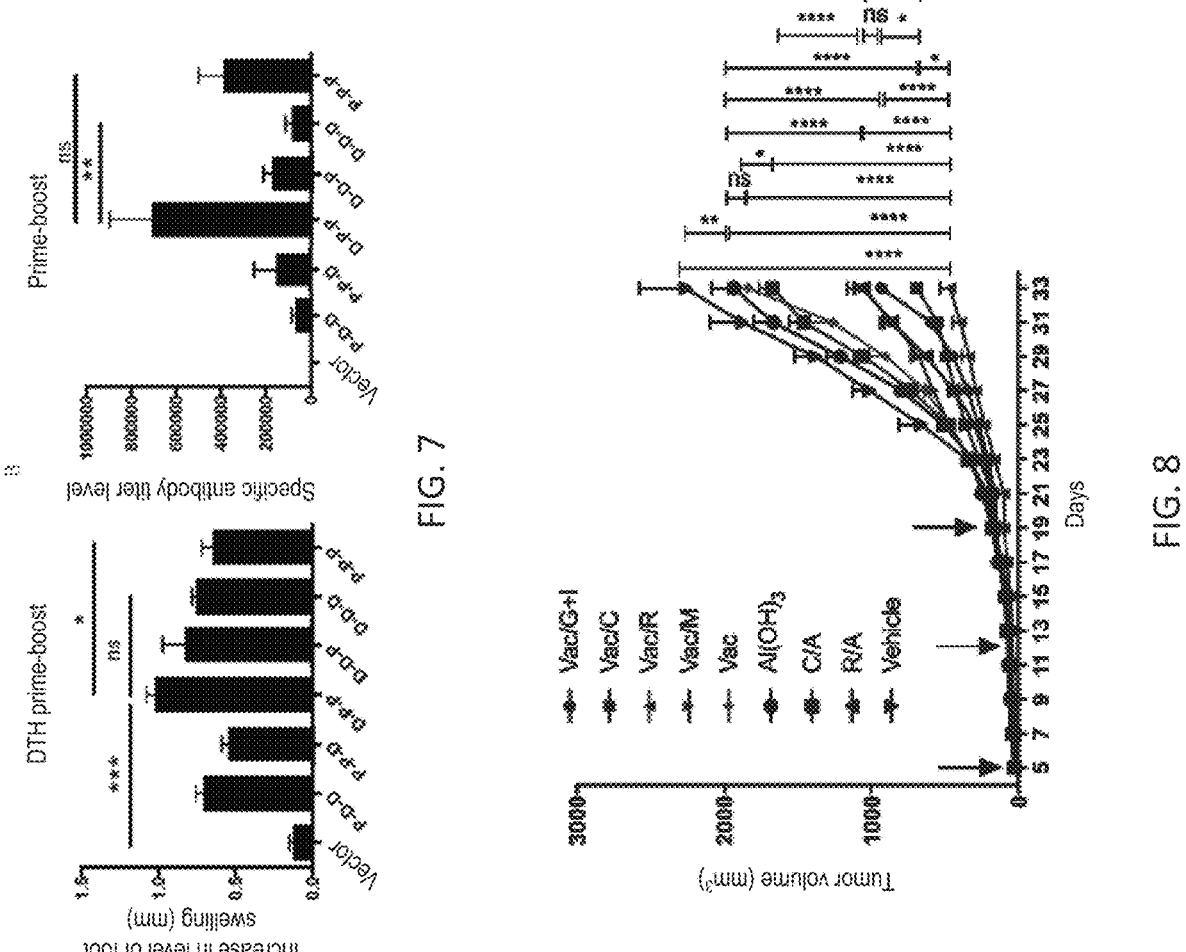
FIG. 7 shows the results of DTH and specific antibody titer 7 days after the final immunization of co-immunization in Example 10.
FIG. 8 shows the tumor growth curves of tumor mice after tumor inoculation in Example 11, wherein the arrow positions are the vaccine immunization time points.

DTH results 7 days after the final immunization are shown in A in FIG. 7, wherein D represents one injection of DNA vaccine and P represents one injection of protein vaccine.

The results showed that the immunization strategy of one injection of DNA vaccine plus two injections of protein vaccine (D-P-P) could induce the highest level of DTH response, followed by D-D-P, D-D-D, and P-P-P. In another aspect, for the VP1-specific antibody titer level, the optimal immunization strategy was D-P-P, followed by P-P-P, D-D-P, and D-D-D (B in FIG. 7). As can be seen from a comparison between different immunization strategies, the immunization strategy of one injection of DNA vaccine plus two injections of protein vaccine (DPP) could achieve higher levels of anti-VP1 antibody and DTH response, which indicates that this immunization strategy is able to elicit both humoral and cellular immune responses.

Example 11. Study on Therapeutic Effect of MCV-VP1 Therapeutic Vaccines

The cytokine rhGM-CSF was purchased from NCPC Genetech Biotechnology Co., Ltd. Recombinant murine IFN-α2b (rmIFN-α2b) was purchased from Sino Biological Inc. (50525-MNAY). CpG1826 was synthesized by Shanghai Generay Biotech Co., Ltd.

In this study, the MCV therapeutic vaccines were prepared with rhGM-CSF and IFN-α2b (rmIFN-α2b) or CpG, R848 or MPL in combination with Al(OH)$_3$ as adjuvants, and the anti-tumor effect of the MCV therapeutic vaccines were studied.

R848 was purchased from InvivoGen (tlrl-r848). The fluorescently labeled antibody used in the flow cytometry assay in the experiment was purchased from BioLegend or BD. Puromycin was purchased from Yeasen Biotechnology (Shanghai) Co., Ltd. RPMI1640, fetal bovine serum (FBS), trypsin, and penicillin/streptomycin diabody for cell culture were purchased from BI. Blood counting chamber and trypan blue were purchased from Thermo Fisher Scientific.

Female BALB/c mice aged 6-8 weeks used in the experiment were purchased from Shanghai Slac Laboratory Animal Co., Ltd., and were bred in an SPF clean-grade mouse house of Department of Laboratory Animal Science of Fudan University. All animal experimental operations were performed under the guidance of animal protection regulations.

1. Efficacy Evaluation of MCV Therapeutic Vaccines
1) Culturing of CMS5-VP1 Cells In previous experiments, the lentiviral plasmid pcDH-VP1 was transfected into tumor cells CMS5 in BALB/c background by a lipofection method, and a cell strain CMS5-VP1/E2 stably expressing VP1 was selected under the drug pressure of 5 μg/mL puromycin. The tumorigenesis experiment performed in BALB/c mice confirmed that the tumor model was constructed by subcutaneous injection of 1×10$^6$ cells. (see Basic Example 1)

In order to evaluate the efficacy of MCV therapeutic vaccines, CMS5-VP1/E2 cells cryopreserved at −80° C. were thawed. The specific procedures were as follows: CMS5-VP1/E2 cell cryopreservation tube was thawed in a water bath at 37° C., washed twice with an RPMI1640 complete medium, and centrifuged at 1500 rpm for 5 min, and the cells were collected. The cells were resuspended in an RPMI1640 complete medium containing 5 g/mL puromycin, added to a 10 cm cell culture dish, and cultured in an incubator at 37° C. with 5% CO$_2$ overnight.

When the thawed cells grew to cover 80% of the culture dish, they were digested with trypsin and subcultured in two 10 cm cell culture dishes at a ratio of 1:2. When the cells grew to cover 80% of the culture dish, they were digested with trypsin and subcultured in a T75 Flask at a ratio of 1:2. The cells were subsequently subcultured in four T175 Flasks to the 6th generation.

The cells were digested with trypsin, washed twice with PBS, and centrifuged at 1500 rpm for 5 min, and the cells were collected. The cells were resuspended in PBS and filtered through a mesh with a pore size of 40 m to obtain a single cell suspension. A part of the cells were diluted, stained with trypan blue, and counted on a cell counting plate under a microscope. The single cell suspension was diluted to 1×10$^7$ cells/mL with PBS and placed in an ice box at 4° C. for later use.

2) Establishment of Tumor Model

Female BALB/c mice aged 6-8 weeks were randomly grouped, with 5 mice in each group. The mice were subcutaneously inoculated with the CMS5-VP1 cell suspension at 1×10$^6$ cells/100 μL at the back.

3) Preparation and Inoculation of MCV Therapeutic Vaccines

The reassembled protein rVP1 (1.8 mg/mL) prepared in Example 7 was diluted with a buffer, uniformly mixed with 10 mg/mL Al(OH)$_3$ at a ratio of 1:1, and shaken at a low speed in a shaker at 4° C. overnight (to facilitate the uniform adsorption of antigen to the Al(OH)$_3$ adjuvant) to obtain a semi-finished MCV recombinant protein vaccine.

On day 5 after the inoculation of CMS5-VP1 cells, the semi-finished MCV recombinant protein vaccine was uniformly mixed with the adjuvant GM-CSF/IFN-α, CpG, R848, or MPL at a certain ratio to obtain the MCV therapeutic vaccine, which was shaken at a low speed in a shaker at 4° C. for 2 h. The mice were intramuscularly injected with the MCV therapeutic vaccine separately at the hind limb.

The MCV therapeutic vaccine groups and the rest groups were intramuscularly injected 5, 12 and 19 days after the tumor inoculation, wherein the groups were:
Vac/G+I (10 μg of rVP1/10 μg of GM-CSF/1 μg of IFN-α/500 μg of Al(OH)$_3$);
Vac/C (10 μg of rVP1/10 μg of CpG/500 μg of Al(OH)$_3$);
Vac/R (10 μg of rVP1/10 μg of R848/500 μg of Al(OH)$_3$);
Vac/M (10 μg of rVP1/25 μg of MPL/500 μg of Al(OH)$_3$);
Vac (10 μg of rVP1/500 μg of Al(OH)$_3$);
C/A (10 μg of CpG/500 μg of Al(OH)$_3$);
R/A (10 μg of R848/500 μg of Al(OH)$_3$);
Al(OH)$_3$ (500 μg of Al(OH)$_3$); and
Vehicle (100 μL of PBS).

4) Monitoring of Tumor Growth Curves

Tumor size was measured starting on day 5 after the inoculation of CMS5-VP1 cells, once every two days, and tumor volume was calculated. Tumor growth curves were plotted with GraphPad Prism software. The tumor volume was calculated according to the formula: Tumor volume (mm$^3$)=L×W$^2$/2.

Experimental Results:

1. Efficacy Evaluation of MCV Therapeutic Vaccines

In order to evaluate the therapeutic effect of the MCV therapeutic vaccines, in this study, a tumor model was established by constructing a tumor cell line CMS5-VP1 stably expressing VP1 to evaluate the inhibition effect of the MCV therapeutic vaccines on tumor growth. The tumor volume was calculated according to the formula. A graph showing the tumor growth curves was plotted using GraphPad Prism, as shown in FIG. 8. The results of statistical analysis showed that there was a certain difference in the tumor growth curve between the Al(OH)$_3$ control group and the PBS placebo group. The tumor growth curves of the MCV therapeutic vaccine groups were significantly different from that of the Vac vaccine group and the Al(OH)$_3$ control group. Notably, the tumor growth of the control group R848/Al(OH)$_3$ was inhibited, and the tumor growth curve of the CpG/Al(OH)$_3$ group was significantly different from that of the Al(OH)$_3$ control group, with certain inhibition effect, which was not significantly different from that of the Vac vaccine group.

These results indicate that the MCV therapeutic vaccine groups prepared in this study have varying degrees of anti-tumor effect, and adjuvants play a key role in the anti-tumor effect.

Example 12. Study on Anti-Tumor Effect of MCV Therapeutic Vaccines

In this study, the MCV therapeutic vaccines were prepared with R848, CpG, and the like in combination with Al(OH)$_3$ as adjuvants, and the anti-tumor effect of the MCV therapeutic vaccines was studied.

1. Experimental materials: CpG1826 was synthesized by Shanghai Generay Biotech Co., Ltd.; R848 was purchased from InvivoGen (tlrl-r848); and aluminum hydroxide [Al (OH)$_3$] was purchased from Brenntag. Antibodies related to the flow cytometry assay were purchased from BioLegend or eBioscience.

2. Experimental animals: female BALB/c mice aged 6-8 weeks used in the experiment were purchased from Shanghai Sippe-Bk Lab Animal Co., Ltd., and were bred in an SPF clean-grade mice house of Shanghai Sippe-Bk Lab Animal Co., Ltd. All animal experimental operations were performed under the guidance of animal protection regulations.

3. Experimental Procedures:

3.1 Construction of MCV Tumor Model

In previous experimental results, the lentiviral plasmid pcDH-VP1 was transfected into tumor cells CMS5 in BALB/c background by a lipofection method, and a cell strain CMS5-VP1/E2 stably expressing VP1 was selected under the drug pressure of 5 μg/mL puromycin. Female BALB/c mice aged 6-8 weeks were randomly grouped, with 6 mice in each group. An MCV tumor model was constructed by subcutaneously inoculating the mice with a CMS5-VP1 cell suspension at 1×10$^6$ cells/100 μL at the back. (see Basic Example 1)

3.2 Preparation of MCV Therapeutic Vaccines

The reassembled protein rVP1 was diluted with a buffer, uniformly mixed with an aluminum-based adjuvant Al(OH)$_3$ at a ratio of 1:1, and shaken at a low speed in a shaker at 4° C. overnight (to facilitate the uniform adsorption of antigen to the Al(OH)$_3$ adjuvant) to obtain a semi-finished MCV recombinant protein vaccine. The semi-finished MCV recombinant protein vaccine was uniformly mixed with the adjuvant CpG or R848 at a certain ratio, and shaken at a low speed in a shaker at 4° C. for 2 h to obtain the MCV therapeutic vaccines. Regardless of the combination of antigen and adjuvants, the final vaccine (per mouse dose) contained 10 μg of rVP1, 500 μg of Al(OH)$_3$, 10 μg of CpG, and 10 μg of R848 per unit.

3.3 Mouse Immunization

On days 5, 12, and 19 after the mice were inoculated with the CMS5-VP1 cell line, various groups of vaccines were prepared for intramuscular injection of mice at the hind limb. In this example, the mice were divided into 6 groups in total, including:

PBS: 0.1 mL;

VP1/Al: 10 μg of rVP1, 500 μg of Al(OH)$_3$; 0.1 mL;

VP1/CpG/Al: 10 μg of rVP1, 10 μg of CpG, 500 μg of Al(OH)$_3$; 0.1 mL;

VP1/R848/Al: 10 μg of rVP1, 10 μg of R848, 500 μg of Al(OH)$_3$; 0.1 mL;

VP1/CpG/R848/Al: 10 μg of rVP1, 10 μg of CpG, 10 μg of R848, 500 μg of Al(OH)$_3$; 0.1 mL;

CpG/R848/Al: 10 μg of CpG, 10 μg of R848, 500 μg of Al(OH)$_3$; 0.1 mL;

3.4 Monitoring of Tumor Growth Curves

Tumor size was measured starting on day 5 after the inoculation of CMS5 cells, once every two days, and tumor volume was calculated. Tumor growth curves were plotted with GraphPad Prism software. The tumor volume was calculated according to the formula: Tumor volume (mm$^3$) $=L×W^2/2$.

3.5. Cellular Immune Detection

On day 33 after tumor inoculation, the mice were euthanized, spleens were taken and prepared into single cell suspensions, and the level of antigen-specific cellular immune response was detected after in vitro stimulation with a VP1 antigen. Statistical analysis was performed with GraphPad Prism software.

4. Experimental Results 4.1 Photographs of Tumor-Bearing Mice in all Vaccine Groups on Day 33 after Tumor Inoculation are Shown in FIG. 9.

Figures 9, 10:
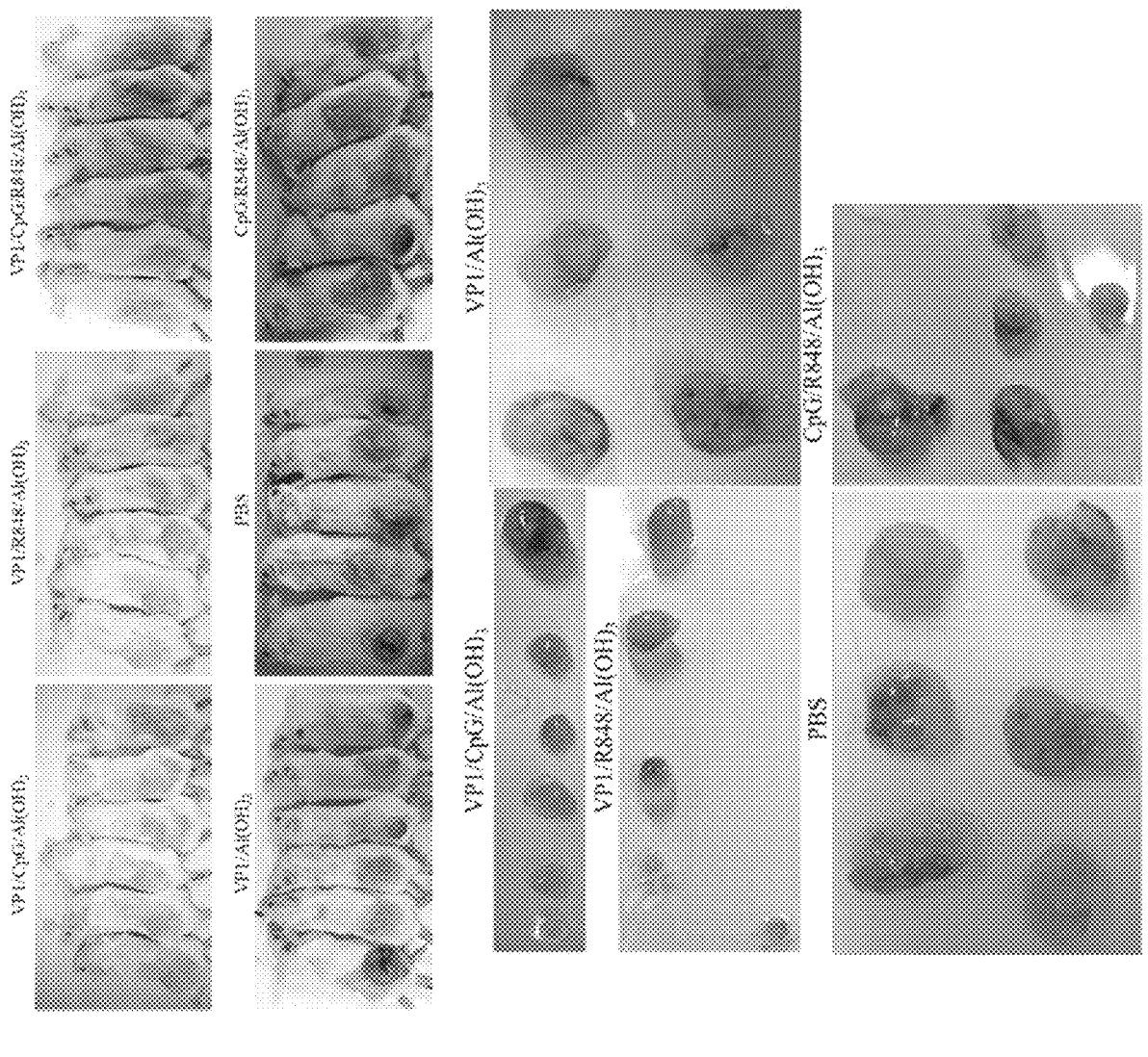
FIG. 9 shows photographs of tumor-bearing mice in all groups on day 33 after tumor inoculation in Example 12.
FIG. 10 shows the tumor tissues of tumor-bearing mice in all groups on day 33 after tumor inoculation in Example 12.

4.2 Tumor Tissues of Tumor-Bearing Mice in all Vaccine Groups on Day 33 after Tumor Inoculation are Shown in FIG. 10.

Figures 11, 12:
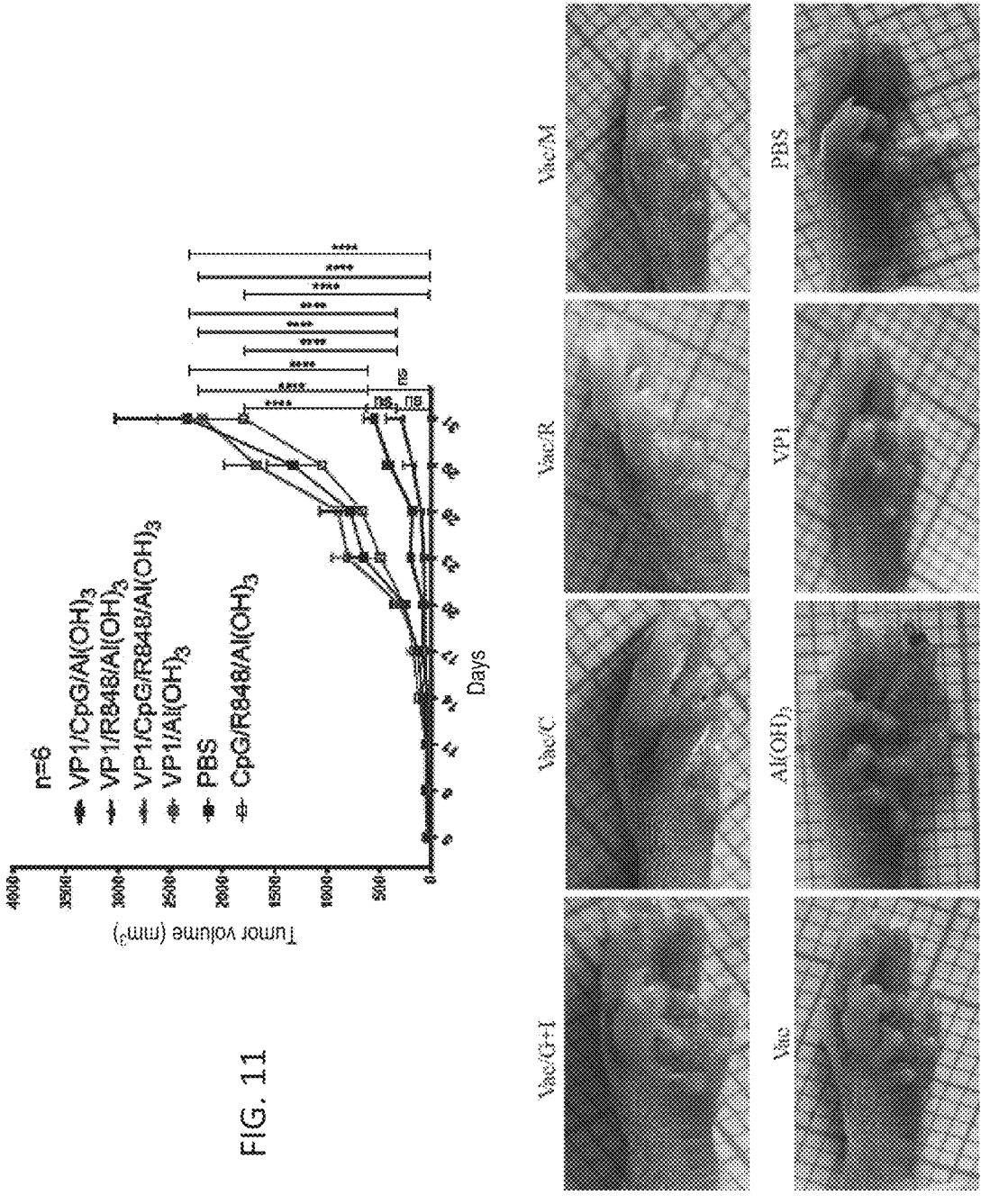
FIG. 11 shows the tumor growth curves of tumor-bearing mice in all groups after tumor inoculation in Example 12.
FIG. 12 shows the degree of paw swelling 24 h after injection of rVP1 or PBS in Example 13.

4.3 Tumor Growth Curves are Shown in FIG. 11.

As can be seen from experimental results, the vaccines of the VP1/CpG/Al group and the VP1/R848/Al group were able to significantly delay the tumor growth of CMS5-VP1 tumor-bearing mice. The VP1/CpG/R848/Al group had the most significant difference in growth curve compared with the PBS non-treatment group, and after treatment with the vaccine of this group, the tumors of the mice were basically controlled, and the tumors were basically not growing in size and tended to be cleared. The experimental results showed that the CpG adjuvant and the R848 adjuvant, either alone or in combination, could improve the treatment level of the VP1/Al vaccine against MCV tumors, wherein the combination of the two had the most significant anti-tumor effect.

4.4 Vaccine-Induced Antigen-Specific Cellular Immune Response 33 days after tumor inoculation, MCV vaccine-induced antigen-specific cellular immune responses in the spleens of the mice were detected by flow cytometry. Both the secretion level of IL-2, TNF-α, IFN-γ, and Granzyme B by CD4$^+$ T cells and the secretion level of IL-2, TNF-α, and IFN-7 by CD8$^+$ T cells induced by the VP1/CpG/R848/Al vaccine group were significantly higher than those of the other vaccine groups, that is to say, the killing effect on tumor cells was achieved by activating the antigen-specific cellular immune response in the body by VP1/CpG/R848/Al vaccine, and secreting effector factors such as IL-2, TNF-α, IFN-γ, and Granzyme B by T cells.

Example 13. Study on Adjuvant Screening for MCV-VP1 Therapeutic Tumor Vaccines 1. Immunological Study on MCV Therapeutic Vaccines A prophylactic vaccine is generally administered prior to the occurrence of a pathogen infection. The vaccine induces the host immune system to produce an antigen-specific antibody and immunological memory, so that the immune system can effectively block the invasion or amplification of the pathogen when the pathogen infection occurs.

If the host is unable to clear the pathogen through the innate immune system or the antibody-mediated adaptive immune response, the activated T cells defend against further infection by the pathogen by their killing effect on the cells already infected with the pathogen.

In the previous studies, the prepared MCV therapeutic vaccines can significantly inhibit the tumor growth. Therefore, animal experiments were performed to determine whether the MCV therapeutic vaccines achieve tumor killing effect by enhancing T cell immune response effect. The immunization procedures were as follows: injections were given on days 0 and 14, and blood was collected on day 28. MCV therapeutic vaccines containing GM-CSF+IFN-α, a TLR9 agonist CpG1826, a TLR7/8 agonist R848, and a TLR4 agonist MPL as adjuvants were injected.

2. Type IV Hypersensitivity Reaction (DTH)

Therapeutic vaccines Vac/G+I, Vac/C, Vac/R, and Vac/M and MCV recombinant protein vaccine Vac and Al(OH)$_3$ adjuvant control group were subjected to two immunization programs (14 days), and the groups were as follows:

Vac/G+I group: 10 μg of rVP1/10 μg of GM-CSF/1 μg of IFN-α/500 μg of Al(OH)$_3$;

Vac/C group: 10 μg of rVP1/10 μg of CpG/500 μg of Al(OH)$_3$;

Vac/R group: 10 μg of rVP1/10 μg of R848/500 μg of Al(OH)$_3$;

Vac/M group: 10 μg of rVP1/25 μg of MPL/500 μg of Al(OH)$_3$;

Vac group: 10 μg of rVP1/500 μg of Al(OH)$_3$;

Al(OH)$_3$ group: 500 μg of Al(OH)$_3$;

VP1 group: 10 μg of rVP1; and

PBS group: 10 μL of PBS.

On day 7 after the immunization program, mice were injected with 10 μL of PBS or 10 μg of rVP1 (10 μL) at the left and right hind limb paws.

The degree of paw swelling 24 h after injection of rVP1 or PBS is shown in FIG. 12. As can be seen from the figure, mice inoculated with the MCV therapeutic vaccines had significant paw swelling.

Figure 13:
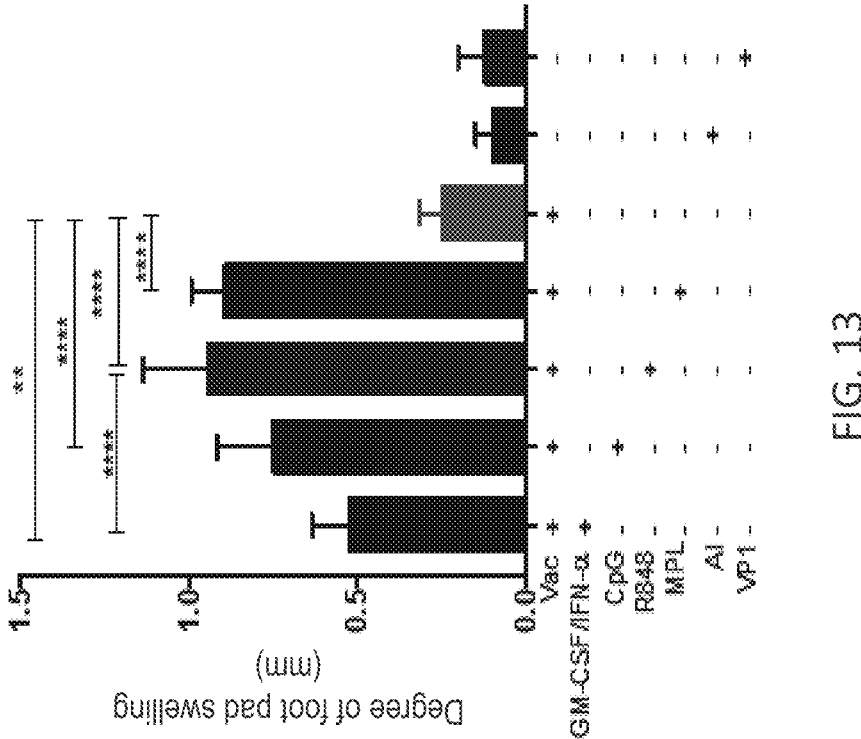
FIG. 13 shows the experimental results of mouse DTH after immunization with adjuvant-containing MCV-VP1 therapeutic tumor vaccines in Example 13.

The paw swelling thickness was calculated for each experimental group according to the formula, and the differences between all vaccine groups were analyzed with GraphPad Prism statistical software. The results after 24 h of DTH are shown in FIG. 13.

As can be seen from the statistical results, the DTH reaction was not significant in the Al(OH)$_3$ or reassembled protein rVP1 group; and the DTH reaction was relatively strong in all of the MCV therapeutic vaccine groups, especially the Vac/R vaccine group, which had an extremely significant difference with Vac. Meanwhile, the differences between the Vac/G+I, Vac/C, and Vac/M vaccine groups and the Vac/R vaccine group were compared. The differences between the Vac/C and Vac/M vaccine groups and the Vac/R vaccine group were not significant, and the differences between the Vac/R group and the Vac/G+I group were extremely significant. Compared with the Vac group, the DTH reaction was the strongest in the Vac/R group with R848 as an adjuvant among the therapeutic vaccine groups, followed by the Vac/C group with CpG as an adjuvant and the Vac/M group with MPL as an adjuvant, all of which showed extremely significant differences (****, $p<0.0001$), while the differences were more significant in Vac/G+I with GM-CSF and IFN-α as adjuvants. This result is in good consistency with the results of the inhibition effect of MCV therapeutic vaccines on tumor growth.

DTH is an immune response of the host to pathogens or exogenous proteins mediated by CD4$^+$ or CD8$^+$ T cells. Therefore, it is speculated that MCV therapeutic vaccines may achieve anti-tumor efficacy by inducing antigen-specific T cell immune responses.

In order to determine the cellular immunity induced by MCV therapeutic vaccines, serological and cellular immunological assays were performed on day 14 after the secondary immunization (i.e., day 28 after the primary immunization).

3. Serological Assay

Blood was collected through the fundus on day 14 after the secondary immunization and mouse serum was isolated. A 96-well ELISA assay plate was coated with rVP1 at 200 ng/well, and ELISA assay was performed with the isolated mouse serum as a primary antibody, the prepared anti-VP1 rabbit polyclonal antibody as a positive control, and the serum of the Al(OH)$_3$ group as a negative control.

A 96-well ELISA assay plate was coated with sVP1 at 200 ng/well as an antigen. Each sample serum was subjected to a serial two-fold dilution at a 1:800 initial dilution to obtain 8 gradients, and the diluted serum was used as a primary antibody at 100 μL/well, with two replicate wells for each dilution. HRP-labeled goat anti-mouse antibody was used as a secondary antibody.

The optical absorbance values were read at $OD_{450}/OD_{620}$ nm, and a value of 2.1 times the OD value of the negative control group was taken as a cutoff value. It is considered positive if the OD value of the experimental group>cut off. If one of the two adjacent dilutions is positive and the other is negative, the former is the antibody titer of the sample.

Figure 14:
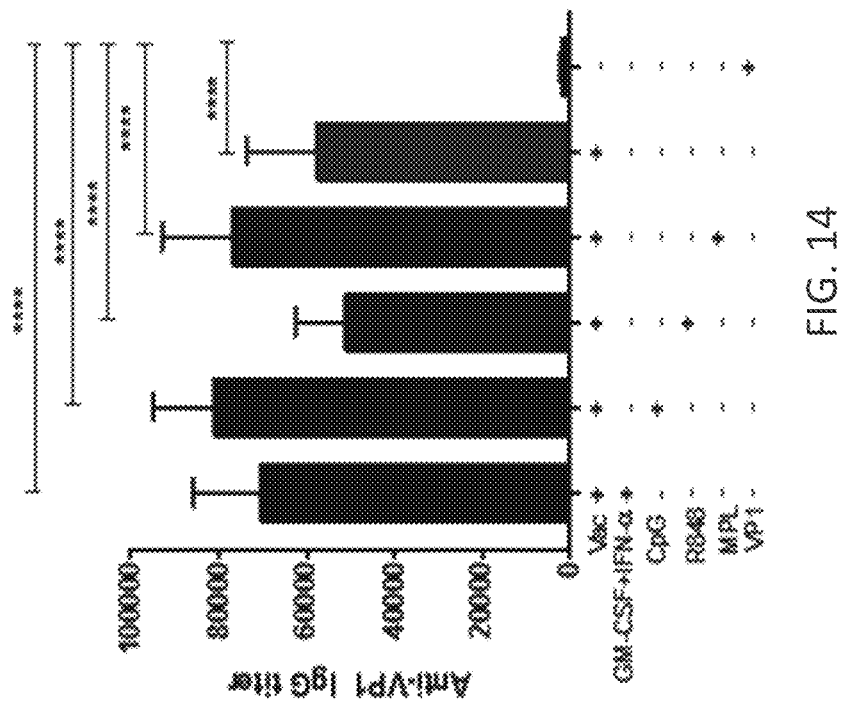
FIG. 14 shows the results of mouse VP1 antibody titer after immunization with adjuvant-containing therapeutic vaccines in Example 13.

The serological assay results are shown in FIG. 14. Compared with the VP1 group, which was immunized against the antigen alone, the VP1-specific antibody titers of the vaccine groups showed significant differences. In addition, the VP1-specific antibody titers of the MCV therapeutic vaccine groups showed a certain difference with that of the MCV recombinant protein vaccine Vac, especially the Vac/C and Vac/M groups, which had a VP1-specific antibody titer significantly higher than the Vac group. This indicates that Al(OH)$_3$ can enhance the antigen-specific humoral response of the host.

4. Cellular Immunological Assay

T cell depletion is a major problem in clinical treatment due to immunosuppression or immunotolerance effect of the tumor microenvironment during tumorigenesis. Therefore, the design of therapeutic vaccines needs to take into account the ability to enhance the cellular immunity of the host. This also becomes an important index for the evaluation of therapeutic vaccines in preclinical studies. GM-CSF+IFN-α, CpG, R848, or MPL was selected based on these hypotheses as an adjuvant for MCV therapeutic vaccines. Therefore, after the serological assay was completed, the cellular immunological assay was performed to determine the stimulatory effect of these novel adjuvants on the cellular response.

The spleen cells of the mice were taken 14 days after the secondary immunization. $1\times10^6$ spleen cells were stimulated with 2 μg of recombinant protein in vitro for 12 h and then blocked with 1×BFA for 4 h. The expression levels of TNF-α, IFN-γ, and IL-2 of T cells were determined by flow cytometry to verify whether the MCV therapeutic vaccines achieve the anti-tumor effect by enhancing the T cell immune response. After framing single cells of lymphocytes and a live cell population negative for Fixable Viability Dye eFluor™ 780, CD3$^+$ T cells were framed, and the expression levels of TNF-$\alpha$, IFN-$\gamma$, and IL-2 of CD4$^+$ and CD8$^+$ T cells were determined.

The method for detecting cytokines by the flow cytometry:

Mice were euthanized, spleen cells were taken, and cytokines were detected by flow cytometry.

(1) Preparation of Spleen Cells

After euthanasia, the mice were soaked in 75% ethanol for 10 min. The spleen was taken and soaked in an RPMI1640 complete medium. The spleen was ground with a 200-mesh copper screen and filtered through a cell sieve with a pore size of 40 m. The filtrate was centrifuged at 1500 rpm for 4 min at 4° C. The supernatant was discarded and the cells were resuspended in 1 mL of red blood cell lysis buffer. The filtrate was centrifuged at 1500 rpm for 4 min at 4° C. The supernatant was discarded and the cells were washed twice with an RPMI1640 complete medium. The filtrate was centrifuged at 1500 rpm for 4 min at 4° C. The supernatant was discarded and the cells were resuspended in an RPMI1640 complete medium. After trypan blue staining, the cells were counted under a microscope.

(2) In Vitro Stimulation of Spleen Cells

According to the cell counting results, the spleen cell suspension was added to a 96-well U-bottom cell culture plate at 1×10$^6$ cells/well. 2 µg of rVP1 or 1 µg/mL Ion+0.1 µg/mL PMA was added as a positive control, and the cells were cultured in an incubator at 37° C. with 5% CO$_2$ for 12 h and blocked with 1×BFA for 4 h. After the blocking was completed, 150 µL of 1×PBS was added to stop the in vitro stimulation reaction. The cells were placed at 4° C. for later use.

(3) Cytokine Staining and Flow Cytometry Assay

The spleen cells stimulated overnight were taken and centrifuged at 1500 rpm for 5 min, and the supernatant was discarded. The cells were resuspended in 1×PBS containing 2% fetal bovine serum (FBS) and blocked for 15 min at room temperature in the dark.

Surface staining: the fluorescently labeled antibody was diluted in 1×PBS containing 2% FBS. After the blocking was completed, the cells were centrifuged at 1500 rpm for 5 min, and the supernatant was discarded. The cells were resuspended in the diluted antibody and stained for 15 min at room temperature in the dark.

Immobilization: after the surface staining was completed, 150 µL of 1×PBS was added to stop the reaction. The cells were centrifuged at 1500 rpm for 5 min, and the supernatant was discarded. 200 µL of paraformaldehyde was added, and the cells were immobilized for 7 min at room temperature in the dark.

Intracellular staining: the fluorescently labeled antibody was diluted in 1×PBS containing 2% FBS. After immobilization with paraformaldehyde, the cells were centrifuged at 1500 rpm for 5 min, and the supernatant was discarded. The cells were washed twice with 1×PBS. The cells were resuspended in the diluted antibody and stained for 15 min at room temperature in the dark.

Flow cytometry assay: after the staining was completed, 150 µL of 1×PBS was added to stop the reaction. The cells were centrifuged at 1500 rpm for 5 min, and the supernatant was discarded. The cells were resuspended in 150 µL of 1×PBS. The expression levels of cytokines were determined by flow cytometry.

(4) Statistical Analysis

All experimental data were analyzed statistically using the statistical software GraphPad Prism 6.0 (GraphPad, La Jolla, CA, USA), and the results were expressed as mean±standard mean error (SEM). Differences in data statistics between groups were compared by t-test. Nc (p>0.05) denotes no significant difference, * denotes a significant difference (p<0.05),  denotes a more significant difference (p<0.01), * denotes a very significant difference (p<0.001), and **** denotes an extremely significant difference (p<0.0001).

Flow Cytometry Assay Results:

(FIG. 15) showed that compared with the Vac, Al(OH)$_3$ or VP1 group, the MCV therapeutic vaccine groups could induce T cells to secrete TNF-$\alpha$, IFN-$\gamma$, and IL-2, and the levels of TNF-$\alpha$, IFN-$\gamma$, and IL-2 in the Vac/R vaccine group were significantly higher than those in other vaccine groups. This was positively correlated with the anti-tumor effect of the MCV therapeutic vaccines. The results of this study indicate that the T cell immune response induced by the MCV therapeutic vaccines achieves the killing effect on tumor cells by CTL. Therefore, it is believed that MCV therapeutic vaccines achieve the anti-tumor effect by inducing antigen-specific T cell immune response.

5. Mechanism Discussion of MCV Therapeutic Vaccine

In the previous studies, it was found that tumor was in a slow growth phase after three inoculations of MCV therapeutic vaccines (days 19-21 after tumor inoculation).

After inoculation of CMS5-VP1 tumor cells, BALB/c mice aged 6-8 weeks were intramuscularly injected with MCV therapeutic vaccines Vac/G+I, Vac/C, Vac/R, and Vac/M, and Vac, as well as control groups, respectively. After the three vaccine inoculations, T cell immune responses were detected on days 20 and 34 after tumor inoculation.

CMS5-VP1/E2 cells were digested with trypsin and prepared into a single cell suspension. The cells were counted, with the cell viability of 95%. The cells were diluted to 1×10$^7$ cells/mL.

Figure 16:
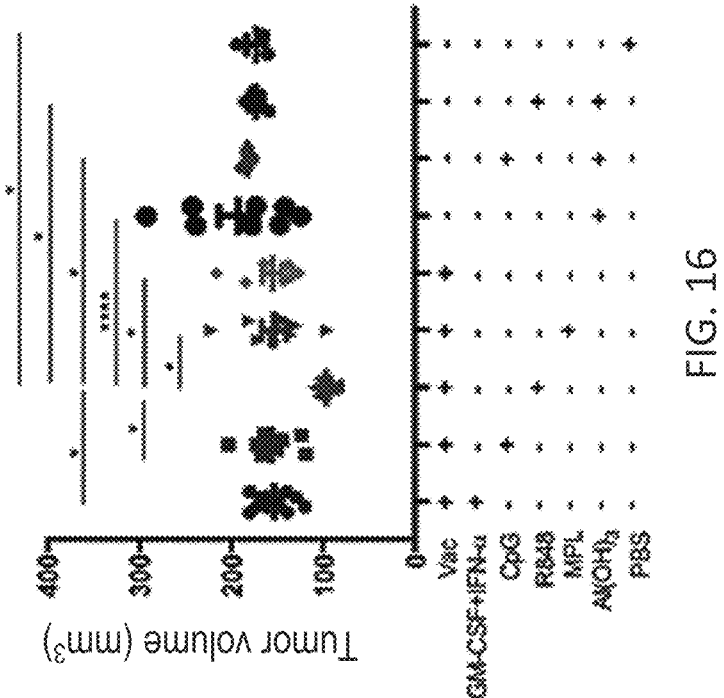
FIG. 16 shows the tumor volume of mice in all groups 19 and 34 days after tumor inoculation in Example 13.
Figure 17:
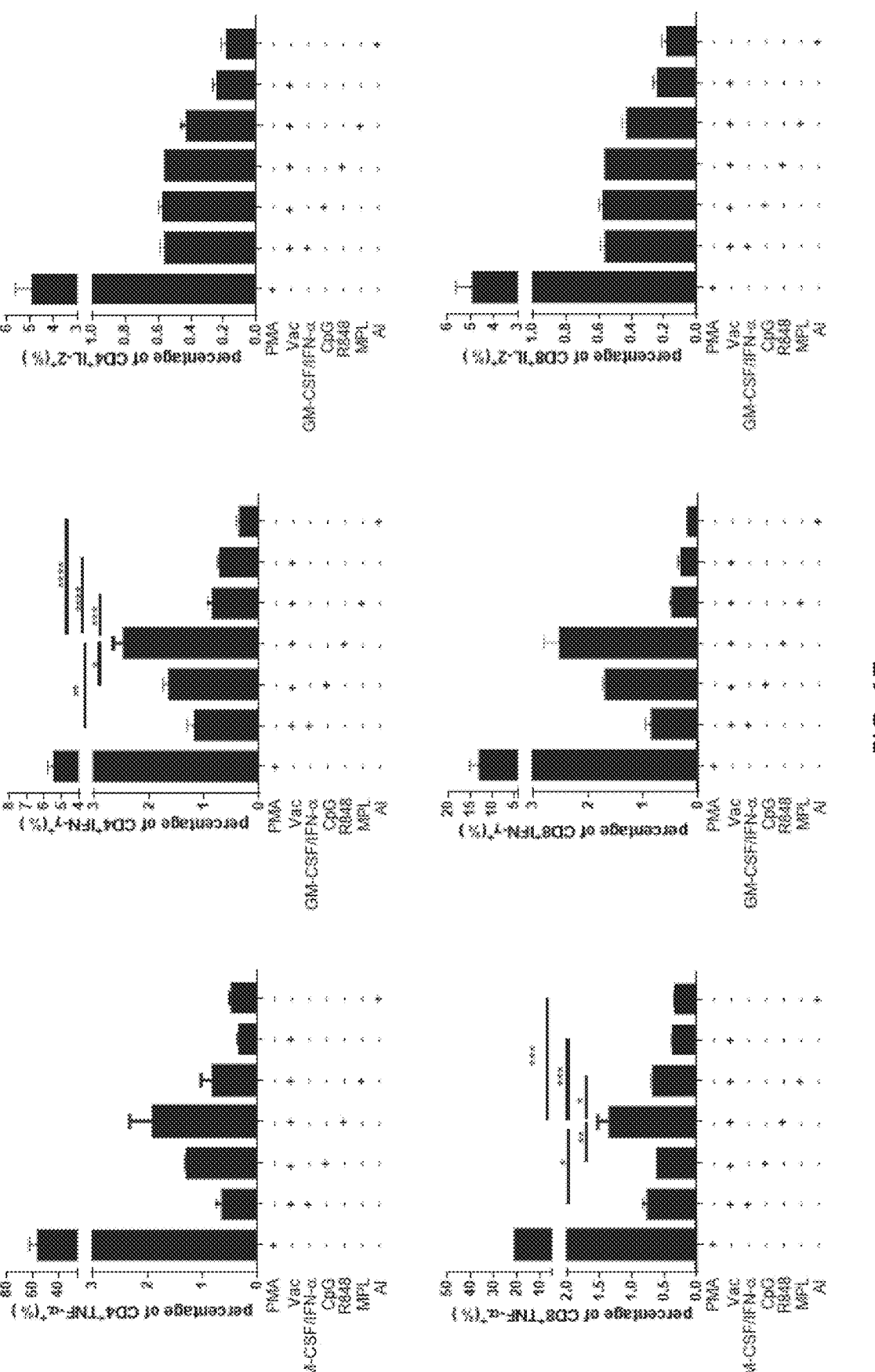
FIG. 17 shows the flow cytometry assay results of the secretion levels of TNF-α, IFN-γ, and IL-2 in CD4$^+$ and CD8$^+$ T cells of mouse spleen cells stimulated with VP1 19 days after tumor inoculation in Example 13.

As shown in FIG. 16, the tumor volume of the Vac/R group was significantly different from that of the other vaccine groups on day 19 after tumor inoculation. Three mice were taken from each of the groups and were euthanized, from which spleens were taken to prepare spleen cell suspensions. 1×10$^6$ spleen cells were stimulated with 2 µg of rVP1 for 20 h, and the stimulation with 1 µg/mL ionomycin+ 0.1 µg/mL phorbol ester (PMA) was taken as a positive control. The antigen-specific cellular immune response was detected by flow cytometry, and the levels of TNF-$\alpha$, IFN-$\gamma$, and IL-2 secreted by CD4$^+$ and CD8$^+$ T cells were determined, as shown in FIG. 17. The levels of TNF-$\alpha$ and IFN-$\gamma$ secreted by CD4$^+$ and CD8$^+$ T cells in the Vac/R vaccine group were higher than those in other vaccine groups, although there was no statistical difference in TNF-$\alpha$ secreted by CD4$^+$ T cells and IFN-$\gamma$ secreted by CD8$^+$ T cells, which may be due to insignificant differences between groups caused by the small number of samples.

On day 34 after tumor inoculation, there were significant differences in tumor volume among all vaccine groups, and the Vac/R vaccine had a particularly significant inhibition effect on tumors. The mice in all vaccine groups were euthanized, from which spleens were taken to prepare spleen cell suspensions. 1×10$^6$ spleen cells were stimulated with 2 µg of rVP1, and the stimulation with 1 µg/mL ionomycin+ 0.1 µg/mL phorbol ester (PMA) was taken as a positive control. The levels of TNF-$\alpha$, IFN-$\gamma$, and IL-2 secreted by CD4$^+$ and CD8$^+$ T cells were determined by flow cytometry.

Figure 18:
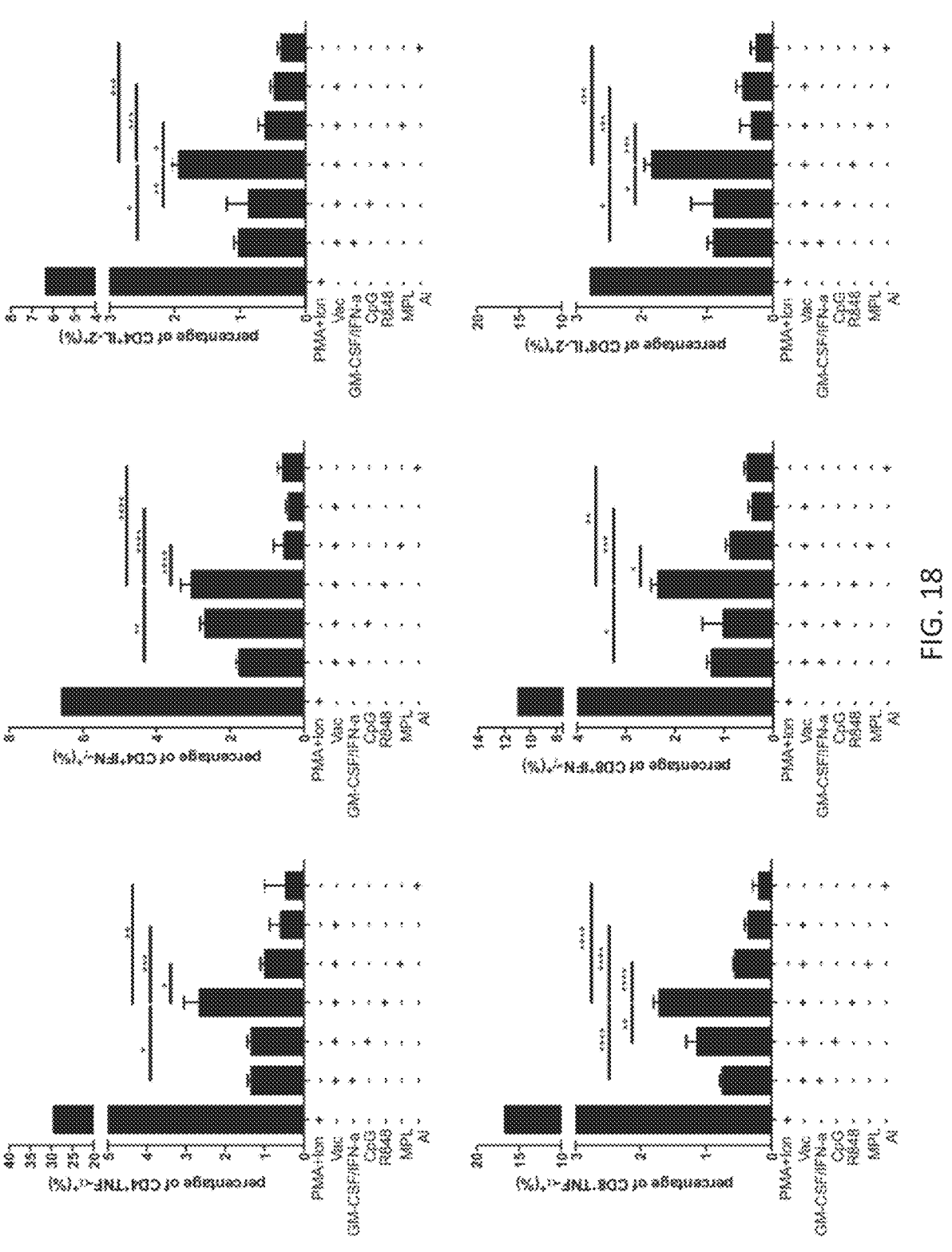
FIG. 18 shows the flow cytometry assay results of the secretion levels of TNF-α, IFN-γ, and IL-2 in CD4$^+$ and CD8$^+$ T cells of mouse spleen cells stimulated with VP1 34 days after tumor inoculation in Example 13.

As shown in FIG. 18, compared with the Vac vaccine, MCV therapeutic vaccines Vac/G+I, Vac/R, Vac/C, and Vac/M could induce an antigen-specific cellular immune response, especially the Vac/R vaccine induced the most significant antigen-specific cellular immune response, and the Vac/R vaccine had the most significant inhibition effect on tumors. These results suggest that MCV therapeutic vaccines may achieve the killing effect on tumor cells by inducing a cellular immune response.

6. Summary

MCV therapeutic vaccines prepared by taking GM-CSF+ IFN-α, CpG1826, R848, or MPL as an adjuvant can have certain anti-tumor effect. Meanwhile, the mechanisms of action of the MCV therapeutic vaccines are preliminarily discussed. It is found that MCV therapeutic vaccines can induce an antigen-specific T cell immune response. These results showed that the feasibility of the MCV therapeutic vaccines developed by this study was proved, and meanwhile, certain data support was provided for the clinical research of the MCV therapeutic vaccines.

Example 14. Study on Immunogenicity of MCV Therapeutic Vaccines

In the previous studies, vaccines prepared from soluble VP1 (sVP1) that were expressed under low-temperature induction were used for immunogenicity studies.

In order to obtain a large amount of VP1, VP1 expressed under high-temperature induction in a fermentation tank mainly formed inclusion bodies. In order to determine whether reassembled VP1 (rVP1) had immunogenicity comparable to sVP1, sVP1 and rVP1 were adsorbed to an $Al(OH)_3$ adjuvant and named sVac and rVac, respectively. BALB/c mice were intramuscularly injected on days 0 and 14, and blood was taken from the orbit on day 28 and centrifuged at 6000 rpm for 10 min to isolate serum. The antigen-specific antibody titer was determined by enzyme-linked immunosorbent assay (ELISA), and the specific procedures were as follows:

Coating: the sVP1 protein was diluted to 2 µg/mL with an antigen coating solution, and a 96-well ELISA plate was coated with the diluted sVP1 at 100 µL/well and incubated at 4° C. overnight.

Blocking: the antigen coating solution in the 96-well plate with antigens incubated overnight was discarded. The plate was washed 3 times with 1×PBST, and 1×PBST blocking solution containing 5% skim milk powder was added at 150 µL/well at 37° C. for blocking for 1 h.

Primary antibody incubation: the blocking solution was discarded. The plate was washed 5 times with 1×PBST. Mouse serum was subjected to a serial two-fold dilution with 1×PBST containing 2% skim milk powder at an initial dilution of 1:200 to obtain 8 gradients, with mouse serum containing an $Al(OH)_3$ adjuvant as a negative control, at 100 µL/well, with two replicate wells set for each sample. The plate was incubated at 37° C. for 1 h.

Secondary antibody incubation: the primary antibody incubation solution was discarded. The plate was washed 5 times with 1×PBST. HRP-labeled goat anti-mouse IgG was subjected to a 10000-fold dilution with 1×PBST containing 2% skim milk powder, added to a 96-well plate at 100 µL/well, and incubated at 37° C. for 1 h.

Color development: the secondary antibody incubation solution was discarded. The plate was washed 5 times with 1×PBST. A TMB substrate chromogenic solution was added at 100 µL/well, and the plate was incubated at 37° C. for 5 min in the dark.

Stopping: 2 M sulfuric acid ($H_2SO_4$) was added at 50 µL/well to stop the color developing reaction.

Reading: optical absorbance values were read at $OD_{450}/OD_{620}$. It is considered positive if the OD value of the experimental group>cut off, cutoff=$2.1×OD_{control\ group}$.

Figure 19:
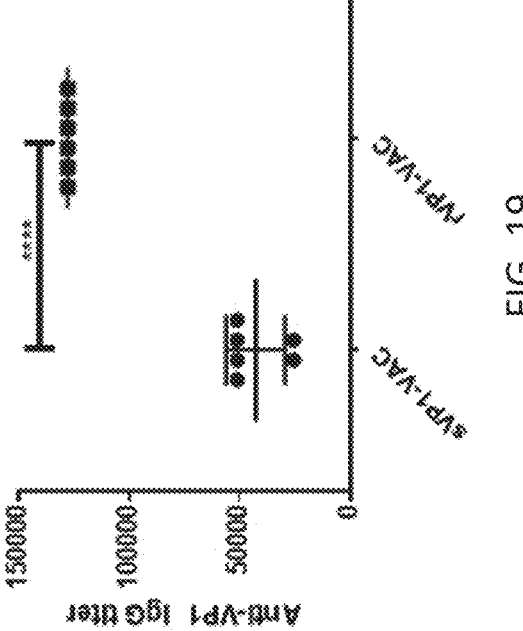
FIG. 19 shows the antigen-specific antibody titer induced by the vaccine sVP1-VAC or rVP1-VAC prepared with sVP1 or rVP1 antigen in Example 14.

Experimental Results:

The antigen-specific antibody titers induced by sVP1-VAC and rVP1-VAC vaccines, prepared with sVP1 and rVP1 as antigens, respectively, are shown in FIG. 19.

As can be seen from the results of the comparison of antibody levels in FIG. 19, rVP1 induced antibody titers that were twice those of sVP1. Therefore, rVP1 prepared by the reassembly process is used as an antigen for MCV vaccine studies.

Example 15. Antigen-Specific Anti-Tumor Effect of MCV Therapeutic Vaccines

The application of MCV therapeutic vaccines on a CMS5-VP1 mouse tumor model can achieve the effect of complete tumor regression. In order to determine that the anti-tumor effect is antigen-specific, in this study, a 4T1 mouse tumor model was established by inoculating BALB/c mice with breast cancer cells 4T1, and the MCV therapeutic vaccines were applied on the mouse model to detect whether the mouse model has antigen specificity.

Experimental materials: CpG1826 was synthesized by Shanghai Generay Biotech Co., Ltd.; R848 was purchased from InvivoGen (tlrl-r848); and aluminum hydroxide [$Al(OH)_3$] was purchased from Brenntag.

Experimental animals: female BALB/c mice aged 6-8 weeks used in the experiment were purchased from Shanghai Sippe-Bk Lab Animal Co., Ltd., and were bred in an SPF clean-grade mice house of Shanghai Sippe-Bk Lab Animal Co., Ltd. All animal experimental operations were performed under the guidance of animal protection regulations.

Experimental Procedures:

1. Establishment of Tumor Model

BALB/c mice were subcutaneously injected with CMS5-VP1 at $1×10^6$ cells/100 µL on the left side, and breast cancer cells 4T1 or fibrosarcoma cells CMS5 at $1×10^6$ cells/100 L on the right side.

2. Mouse Immunization

On day 5 after tumor inoculation, tumor-bearing mice were randomly grouped, with 5 mice in each group, and on days 5, 12, and 19 after tumor inoculation, the mice were intramuscularly injected with MCV therapeutic vaccines (VP1/CpG/R848/$Al(OH)_3$) or vaccines without VP1 (CpG/R848/$Al(OH)_3$) or PBS on the left side.

Figure 20:
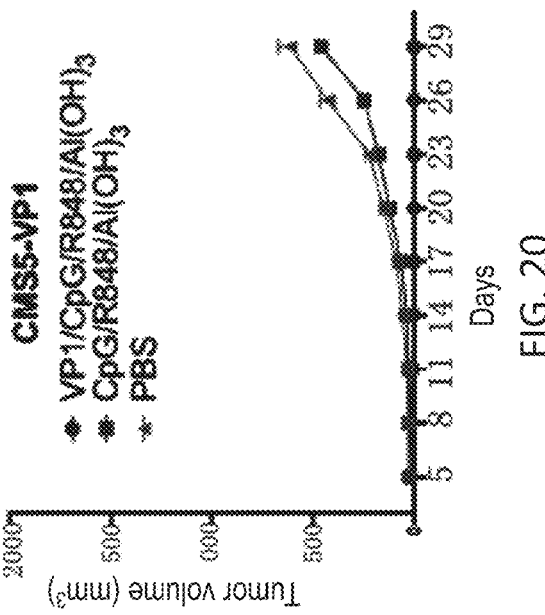
FIG. 20 shows the CMS5-VP1 tumor growth curves of the tumor-bearing mice in Example 15.
Figure 22:
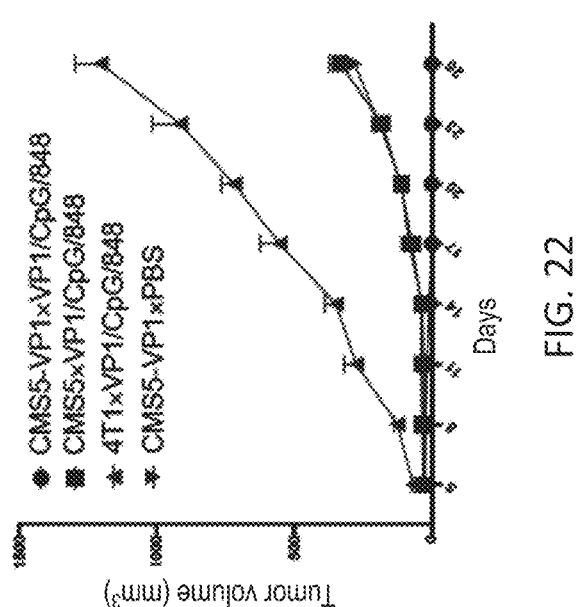
FIG. 22 shows the anti-tumor effect of the MCV therapeutic vaccines on three tumor models CMS5-VP1, CMS5, and 4T1 in Example 15.
Figure 21:
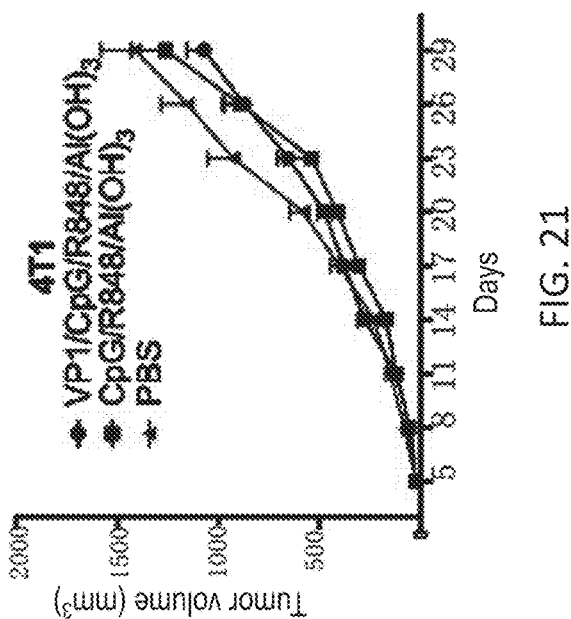
FIG. 21 shows the 4T1 tumor growth curves of the tumor-bearing mice in Example 15.

Experimental Results:

The CMS5-VP1 tumor growth curves of tumor-bearing mice are shown in FIG. 20. The 4T1 tumor growth curves of tumor-bearing mice are shown in FIG. 21. The anti-tumor effect of MCV therapeutic vaccines on three tumor models CMS5-VP1, CMS5, and 4T1 is shown in FIG. 22.

As can be seen from the results, after the CMS5-VP1/4T1 tumor-bearing mice were inoculated with the MCV therapeutic vaccines, the CMS5-VP1 tumor on the left side was completely regressed, the CMS5-VP1 tumors were evident in the CpG/R848/aluminum-based adjuvant group and the PBS control group, and the 4T1 tumor on the right side of the tumor-bearing mice of each vaccine group was evident, that is to say, the MCV therapeutic vaccine could not completely inhibit the growth of the 4T1 tumor. The results also showed that the MCV therapeutic vaccines could only make the CMS5-VP1 tumors regress and had no therapeutic effect on CMS5 and 4T1 tumors, that is to say, the anti-tumor effect of the MCV therapeutic vaccines was specific for targeting the CMS5-VP1 tumor cells expressing VP1.

Example 16. Study on Immune Persistence Induced by 2 or 3 Injections of Therapeutic Vaccines In the previous experimental process, it is found that two injections of MCV therapeutic vaccines have been able to achieve complete regression of CMS5-VP1 tumors, and therefore immune persistence explorations of 2 and 3 injections of therapeutic vaccines were performed in subsequent experiments. That is, BALB/c tumor mice inoculated with CMS5-VP1 were immunized with 2 or 3 injections of therapeutic vaccines and were re-challenged with CMS5-VP1 after the last immunization, and tumor growth was monitored. The specific procedures were as follows:

1. Experimental materials: CpG1826 was synthesized by Shanghai Generay Biotech Co., Ltd.; R848 was purchased from InvivoGen (tlrl-r848); and aluminum hydroxide [Al(OH)$_3$] was purchased from Brenntag.

2. Experimental animals: female BALB/c mice aged 6-8 weeks used in the experiment were purchased from Shanghai Sippe-Bk Lab Animal Co., Ltd., and were bred in an SPF clean-grade mice house of Shanghai Sippe-Bk Lab Animal Co., Ltd. All animal experimental operations were performed under the guidance of animal protection regulations.

3. Establishment of tumor model: BALB/c mice were subcutaneously injected with CMS5-VP1 at $1\times10^6$ cells/100 µL.

4. Two injections of immunization: on day 5 after tumor inoculation, tumor-bearing mice were randomly grouped, with 8 mice in each group, and on days 5 and 12 after tumor inoculation, the mice were intramuscularly injected with vaccines. The mice were divided into 5 groups in total, including:

PBS: 0.1 mL;

VP1/CpG/Al(OH)$_3$: 10 µg of rVP1; 10 µg of CpG; 500 µg of Al(OH)$_3$; 0.1 mL;

VP1/R848/Al(OH)$_3$: 10 µg of rVP1; 10 µg of R848; 500 µg of Al(OH)$_3$; 0.1 mL;

VP1/CpG/R848/Al(OH)$_3$: 10 µg of rVP1; 10 µg of CpG; 10 µg of R848; 500 µg of Al(OH)$_3$; 0.1 mL; and VP1/Al(OH)$_3$: 10 µg of rVP1; 500 µg of Al(OH)$_3$; 0.1 mL.

Three injections of immunization: on day 5 after tumor inoculation, tumor-bearing mice were randomly grouped, with 8 mice in each group, and on days 5, 12 and 19 after tumor inoculation, the mice were intramuscularly injected with vaccines. The mice were divided into 4 groups in total, including:

PBS: 0.1 mL;

CpG/R848/Al(OH)$_3$: 10 µg of CpG; 10 µg of R848; 500 µg of Al(OH)$_3$; 0.1 mL;

VP1/CpG/R848/Al(OH)$_3$: 10 µg of rVP1; 10 µg of CpG; 10 µg of R848; 500 µg of Al(OH)$_3$; 0.1 mL; and VP1/Al(OH)$_3$: 10 µg of rVP1; 500 µg of Al(OH)$_3$; 0.1 mL.

5. Re-challenge of CMS5-VP1 tumor cells: 30 days after the last immunization (2 injections: day 42; three injections: day 49), mice in the MCV therapeutic vaccine immunization group were subcutaneously injected again with CMS5-VP1 cells at $1\times10^6$ cells/100 µL at the back.

6. The experimental results were as follows: the tumor growth curves of CMS5-VP1 tumor-bearing mice in vaccine groups after inoculation with 2 and 3 injections of vaccines (two injections on the left side and three injections on the right side).

The results showed that either two or three injections of the MCV therapeutic vaccines resulted in complete tumor regression in MCV-VP1 tumor-bearing mice. The tumor growth curves for the CMS5-VP1 tumor re-challenge experiment after the last immunization (two injections on the left side and three injections on the right side). The results showed that although both the two and three injections of therapeutic vaccines could achieve complete regression of the tumors, the three injections of vaccines had better immune persistence.

Example 17. Study on Mechanisms of Action of MCV Therapeutic Vaccines Against Tumors The previous studies have shown that the MCV therapeutic vaccines could induce an antigen-specific cellular immune response in the body to achieve an anti-tumor effect. In order to further determine a relevant mechanism, in this study, the T cells were blocked with the anti-CD3, anti-CD4, or anti-CD8 antibody, and the tumor growth curves after vaccine immunization were assayed simultaneously.

1. Experimental materials: CpG1826 was synthesized by Shanghai Generay Biotech Co., Ltd.; R848 was purchased from InvivoGen (tlrl-r848); and aluminum hydroxide [Al(OH)$_3$] was purchased from Brenntag. Mouse antibodies anti-CD3, anti-CD4, and anti-CD8 were purchased from BioxCell.

2. Experimental animals: female BALB/c mice aged 6-8 weeks used in the experiment were purchased from Shanghai Sippe-Bk Lab Animal Co., Ltd., and were bred in an SPF clean-grade mice house of Shanghai Sippe-Bk Lab Animal Co., Ltd. All animal experimental operations were performed under the guidance of animal protection regulations.

3. Establishment of tumor model: BALB/c mice were subcutaneously injected with CMS5-VP1 at $1\times10^6$ cells/100 µL.

4. Mouse immunization: tumor-bearing mice were randomly grouped on day 4 after tumor inoculation, with 5 groups in total, and 5 mice in each group, wherein three groups of tumor-bearing mice were intraperitoneally injected with 200 µg of anti-CD3, anti-CD4, and anti-CD8 monoclonal antibodies on days 4, 11, and 18 after tumor inoculation, respectively, to block CD3, CD4, or CD8 T cells, and intramuscularly injected with MCV therapeutic vaccines (VP1/CpG/R848/Al(OH)$_3$) or PBS 24 h after antibody injection (5 days, 12 days, and 19 days after tumor inoculation).

Figure 23:
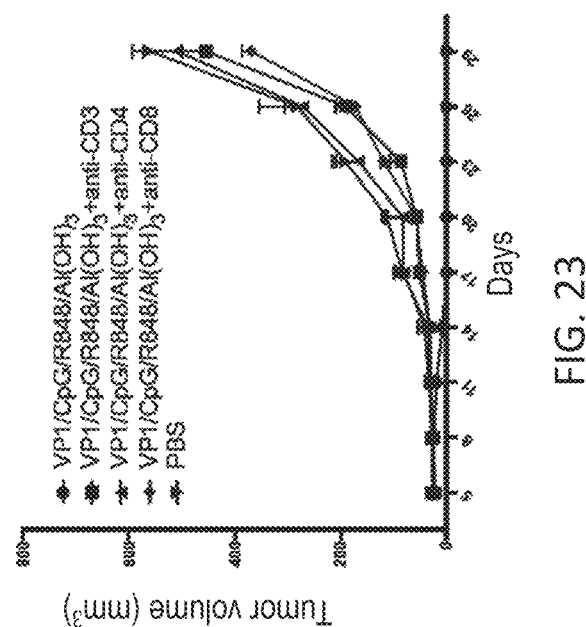
FIG. 23 shows the tumor growth curves of mice after immunization with the MCV therapeutic vaccines in Experimental Example 17

5. Experimental results: the tumor growth curves are shown in FIG. 23.

As can be seen from the results, the anti-tumor effect of MCV therapeutic vaccines was attenuated after blocking the corresponding T cells with CD3, CD4, and CD8 monoclonal antibodies, that is to say, T cells are critical for the achievement of the anti-tumor effect of MCV therapeutic vaccines.

Example 18. Correlation Between Anti-Tumor Effect of MCV Therapeutic Vaccines and Tregs 1. Experimental materials: CpG1826 was synthesized by Shanghai Generay Biotech Co., Ltd.; R848 was purchased from InvivoGen (tlrl-r848); and aluminum hydroxide [Al(OH)$_3$] was purchased from Brenntag.

2. Experimental animals: female BALB/c mice aged 6-8 weeks used in the experiment were purchased from Shanghai Sippe-Bk Lab Animal Co., Ltd., and were bred in an SPF clean-grade mice house of Shanghai Sippe-Bk Lab Animal Co., Ltd. All animal experimental operations were performed under the guidance of animal protection regulations.

3. Tumor model establishment was performed by referring to Experimental Example 1.

4. Mouse immunization: on day 5 after tumor inoculation, mice were randomly divided into three groups, with five mice in each group, and intramuscularly immunized on days 5, 12, and 19. The three groups include:

PBS: 0.1 mL;

VP1/CpG/R848/Al(OH)₃: 10 μg of rVP1; 10 μg of CpG; 10 μg of R848; 500 μg of Al(OH)₃; 0.1 mL; and VP1/Al(OH)₃: 10 μg of rVP1; 500 μg of Al(OH)₃; 0.1 mL.

5. Flow cytometry assay: on day 33 after tumor inoculation, the mice were sacrificed, the spleens were taken and prepared into a single cell suspension, and the expression of the Treg-related cytokines of all vaccine immunization groups was detected by flow cytometry.

Figure 24:
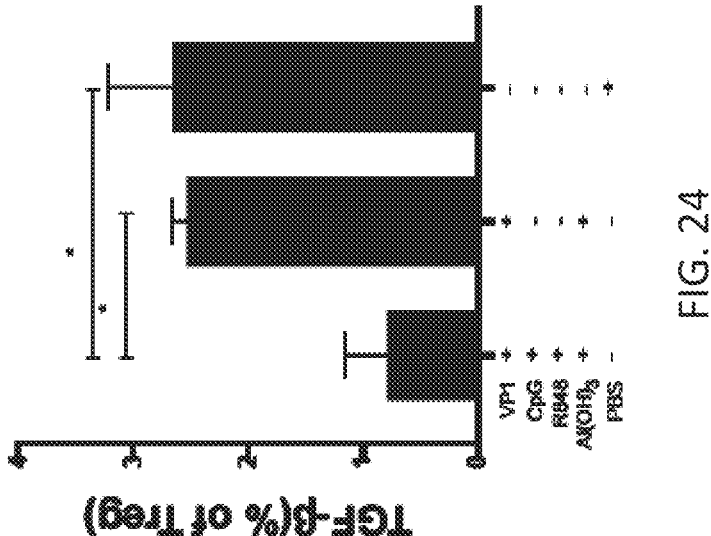
FIG. 24 shows the expression levels of TGF-β of Tregs in lymph nodes of tumor-bearing mice in all vaccine groups in Example 18.

6. Experimental Results:

The expression levels of TGF-β of Tregs in lymph nodes of tumor-bearing mice in all vaccine groups are shown in FIG. 24.

As can be seen from the experimental results, the expression level of TGF-β of Treg cells in mice of MCV therapeutic vaccine immunization groups (VP1/CpG/R848/Al (OH)₃) was significantly lower than that of other experimental groups, predicting that after MCV therapeutic vaccine immunization, Treg cell response can be inhibited, and T cell immune response can be enhanced, so that the anti-tumor effect is achieved.

The above examples only illustrate several embodiments of the present invention for the purpose of specific and detailed description but should not be construed as limiting the scope of the present invention. It should be noted that various changes and modifications can be made by those skilled in the art without departing from the spirit of the present disclosure, and these changes and modifications are all within the scope of the present disclosure. Therefore, the protection scope of the present disclosure should be determined with reference to the appended claims.

What is claimed is:

1. A vaccine composition against Merkel cell carcinoma comprising: (a) Merkel cell polyomavirus capsid protein VP1 or a nucleic acid comprising a nucleotide sequence encoding the Merkel cell polyomavirus capsid protein VP1; and (b) a TLR agonist comprising one or more of CpG, R848, and MPL;

wherein the nucleotide sequence encoding the Merkel cell polyomavirus capsid protein VP1 is 71.9%-74.7% identical to SEQ ID No. 6.

2. The vaccine composition according to claim 1, wherein the TLR agonist is a combination of CpG and R848.

3. The vaccine composition according to claim 1, wherein the vaccine composition further comprises an aluminum-based adjuvant.

4. The vaccine composition according to claim 3, wherein the vaccine composition comprises 5-500 parts by weight of the Merkel cell polyomavirus capsid protein VP1 or the nucleic acid encoding the Merkel cell polyomavirus capsid protein VP1, 2.5-250 parts by weight of the TLR agonist, and 10-1000 parts by weight of the aluminum-based adjuvant.

5. The vaccine composition according to claim 4, wherein the vaccine composition comprises 10-100 parts by weight of the Merkel cell polyomavirus capsid protein VP1 or the nucleic acid encoding the Merkel cell polyomavirus capsid protein VP1, 5-100 parts by weight of the TLR agonist, and 50-500 parts by weight of the aluminum-based adjuvant.

6. The vaccine composition according to claim 1, wherein the nucleotide sequence encoding the Merkel cell polyomavirus capsid protein VP1 is set forth in SEQ ID No. 1, SEQ ID No. 2, SEQ ID No. 3, or SEQ ID No. 4.

7. A nucleic acid encoding Merkel cell polyomavirus capsid protein VP1, wherein the nucleic acid comprising a nucleotide sequence 71.9%-74.7% identical to SEQ ID No. 6; and wherein the nucleotide sequence encodes the VP1.

8. The nucleic acid according to claim 7, wherein the nucleic acid comprises the nucleotide sequence set forth in SEQ ID No. 1, SEQ ID No. 2, SEQ ID No. 3, or SEQ ID No. 4.

9. A method for preparing a vaccine composition against Merkel cell carcinoma, the method comprising mixing the nucleic acid according to claim 7 or the VP1 protein encoded thereby with an adjuvant to form the vaccine composition.

10. The method according to claim 9, wherein the nucleic acid comprises the nucleotide sequence set forth in SEQ ID No. 1, SEQ ID No. 2, SEQ ID No. 3, or SEQ ID No. 4.

11. A vaccine composition against Merkel cell carcinoma, wherein the vaccine composition comprises the nucleic acid according to claim 7, or the VP1 protein encoded thereby.

12. The vaccine composition according to claim 11, wherein the vaccine composition comprises the nucleic acid comprising the nucleotide sequence set forth in SEQ ID No. 1, SEQ ID No. 2, SEQ ID No. 3, or SEQ ID No. 4, or the VP1 protein encoded thereby.

13. The vaccine according to claim 12, wherein the vaccine composition further comprises an adjuvant comprising a TLR agonist and an aluminum-based adjuvant, the TLR agonist being one or more of CpG, R848, and MPL.

14. A method for treating or reducing the risk for Merkel cell carcinoma in a subject, the method comprising administering to a subject in need thereof the vaccine composition according to claim 11.

15. The method according to claim 14, wherein the vaccine composition comprises the nucleic acid comprising the nucleotide sequence set forth in SEQ ID No. 1, SEQ ID No. 2, SEQ ID No. 3, or SEQ ID No. 4, or the VP1 protein encoded thereby.

16. The method according to claim 14, wherein the vaccine composition further comprises an adjuvant comprising a TLR agonist and an aluminum-based adjuvant, and wherein the TLR agonist comprises one or more of CpG, R848, and MPL.

17. The method according to claim 14, wherein the subject has Merkel cell carcinoma or is at risk for developing Merkel cell carcinoma.

18. The vaccine composition of claim 1, wherein the nucleic acid is a DNA plasmid.

19. The nucleic acid of claim 7, which is a DNA plasmid.

20. The vaccine composition of claim 11, wherein the nucleic acid is a DNA plasmid.

* * * * *